(12) United States Patent
Dalessandro et al.

(10) Patent No.: US 12,012,678 B2
(45) Date of Patent: Jun. 18, 2024

(54) CARTRIDGES WITH FIRST AND SECOND CHANNELS FOR GUIDING BARBED SUTURES HAVING END EFFECTORS INTO BRAIDING MACHINES

(71) Applicant: Ethicon, Inc., Somerville, NJ (US)

(72) Inventors: Victoria Dalessandro, Scotch Plains, NJ (US); Jason T. Perkins, Easton, PA (US); Glenn R. Cook, Clinton, NJ (US); Sean Biddulph, South Plainfield, NJ (US); Robert C. Scogna, Rocky Hill, NJ (US)

(73) Assignee: Ethicon, Inc., Raritan, NJ (US)

( * ) Notice: Subject to any disclaimer, the term of this patent is extended or adjusted under 35 U.S.C. 154(b) by 470 days.

(21) Appl. No.: 17/336,680

(22) Filed: Jun. 2, 2021

(65) Prior Publication Data
US 2021/0386421 A1 Dec. 16, 2021

Related U.S. Application Data

(60) Provisional application No. 63/039,649, filed on Jun. 16, 2020.

(51) Int. Cl.
*D04C 3/12* (2006.01)
*A61B 17/04* (2006.01)
(Continued)

(52) U.S. Cl.
CPC ............ *D04C 3/12* (2013.01); *A61B 17/0482* (2013.01); *A61B 17/06128* (2013.01);
(Continued)

(58) Field of Classification Search
CPC ........ D04C 3/12; D04C 3/48; A61B 17/0482; A61B 17/06128; A61B 2017/00526; A61B 2017/06176
(Continued)

(56) References Cited

U.S. PATENT DOCUMENTS

| 4,546,769 A | 10/1985 | Planck et al. |
| 4,946,467 A | 8/1990 | Ohi et al. |

(Continued)

FOREIGN PATENT DOCUMENTS

| CA | 3066064 A1 * | 12/2018 | ......... A61B 17/0401 |
| EP | 3533399 | 9/2019 | |
| EP | 3180040 | 5/2020 | |

OTHER PUBLICATIONS

International Search Report issued in corresponding International Application No. PCT/IB2021/055169, dated Sep. 9, 2021, 5 pages.
(Continued)

*Primary Examiner* — Shaun R Hurley

(57) ABSTRACT

A device for guiding a barbed suture into a braider preferably includes an elongated body having a proximal end, a distal end, and a longitudinal axis that extends from the proximal end to the distal end of the elongated body. The elongated body includes a first channel extending along the longitudinal axis of the elongated body and having a first distal opening at the distal end of the elongated body, whereby the said first channel has a first cross-sectional area, and a second channel extending along the longitudinal axis of the elongated body and having a second distal opening at the distal end of the elongated body, whereby the second channel has a second cross-sectional area that is different than the first cross-sectional area of the first channel. The device has an elongated slot extending along the longitudinal axis of the elongated body that interconnects the first and second channels. A barbed suture is loaded into the elongated body. The barbed suture includes an elongated core having a proximal end, a distal end, a barbed section including barbs extending outwardly from the elongated core, an end effector secured to the proximal end of the elongated core, and an interconnecting segment of the elongated core that is distal to the end effector and proximal
(Continued)

to the barbed section. The barbed section of the barbed suture is disposed within the first channel, the end effector of the barbed suture is disposed within the second channel, and the interconnecting segment of said barbed suture extends through the elongated slot.

20 Claims, 44 Drawing Sheets

(51) Int. Cl.
  *A61B 17/06* (2006.01)
  *D04C 1/12* (2006.01)
  *D04C 3/48* (2006.01)
(52) U.S. Cl.
  CPC .......... *A61B 17/06166* (2013.01); *D04C 1/12* (2013.01); *D04C 3/48* (2013.01); *A61B 2017/06176* (2013.01)
(58) Field of Classification Search
  USPC .............................................. 87/34
  See application file for complete search history.

(56) References Cited

U.S. PATENT DOCUMENTS

| | | |
|---|---|---|
| 5,931,855 A | 8/1999 | Buncke |
| 8,210,085 B2 | 7/2012 | Lindh, Sr. et al. |
| 8,216,497 B2 | 7/2012 | Lindh, Sr. et al. |
| 8,353,931 B2 | 1/2013 | Stopek et al. |
| 8,663,277 B2 | 3/2014 | Collier et al. |
| 8,733,223 B2 | 5/2014 | Lindh, Sr. et al. |
| 9,044,225 B1 | 6/2015 | Goraltchouk et al. |
| 9,206,535 B2 | 12/2015 | Lindh, Sr. et al. |
| 2004/0199208 A1 | 10/2004 | Foerster |
| 2011/0048216 A1 | 3/2011 | Lindh et al. |
| 2011/0251640 A1* | 10/2011 | Lauria .............. A61B 17/06166 606/228 |
| 2013/0226233 A1 | 8/2013 | D'Agostino et al. |
| 2013/0226234 A1 | 8/2013 | Avelar et al. |
| 2015/0032155 A1 | 1/2015 | Dreyfuss et al. |
| 2019/0336123 A1* | 11/2019 | Kumar .............. A61B 17/06066 |

OTHER PUBLICATIONS

Written Opinion of the International Searching Authority issued in corresponding International Application No. PCT/IB2021/055169, dated Sep. 9, 2021, 8 pages.

\* cited by examiner

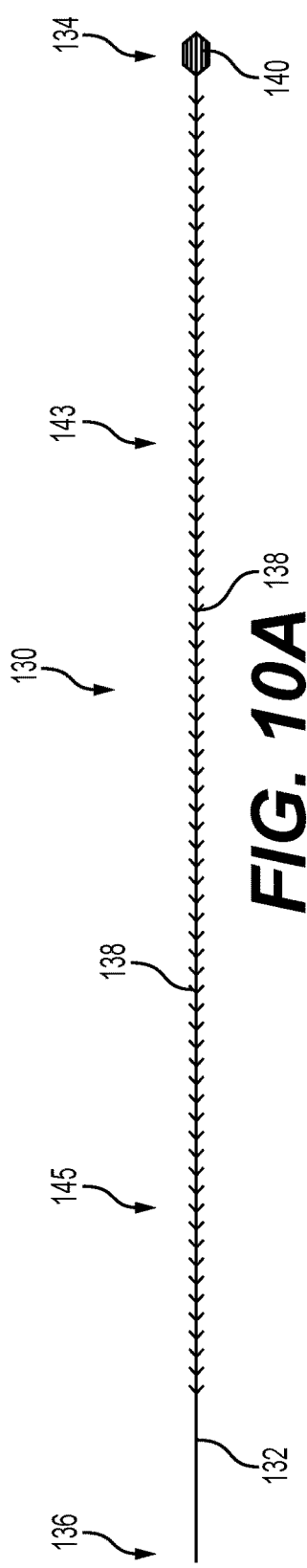
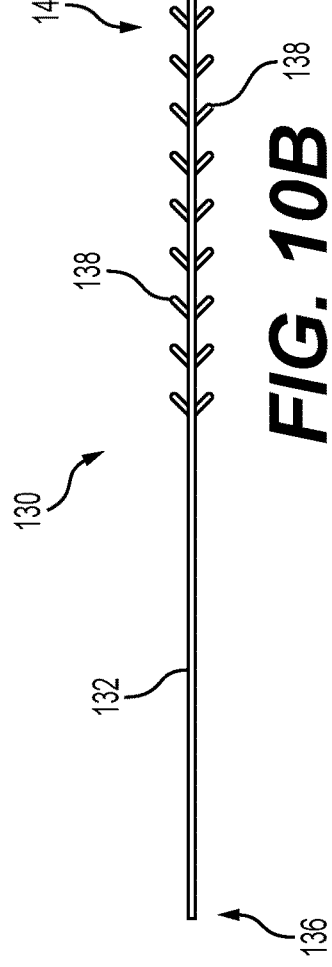
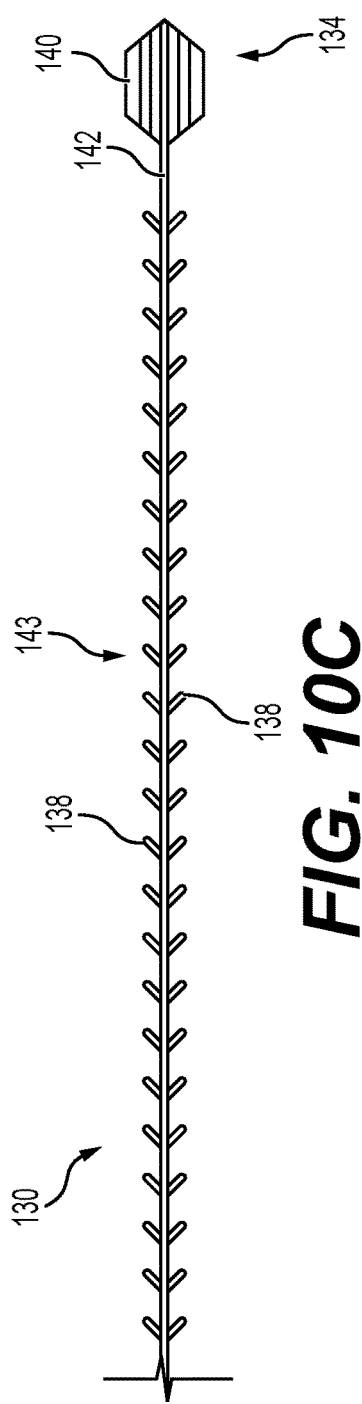
FIG. 10A
FIG. 10B
FIG. 10C

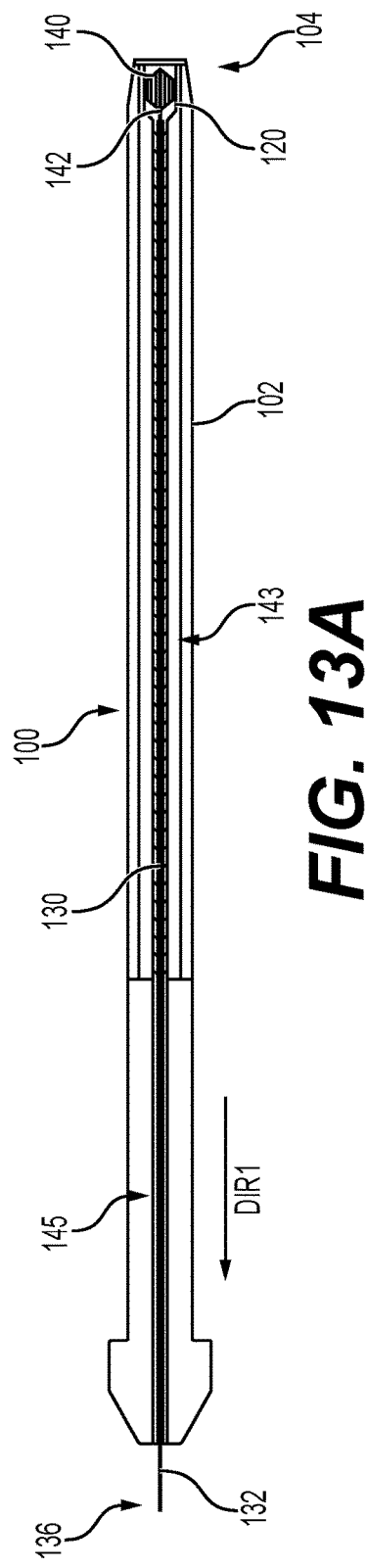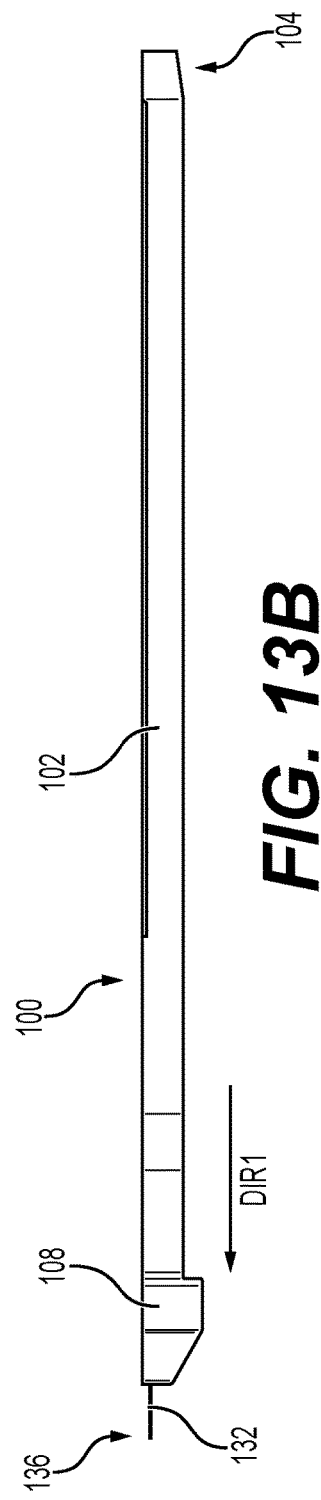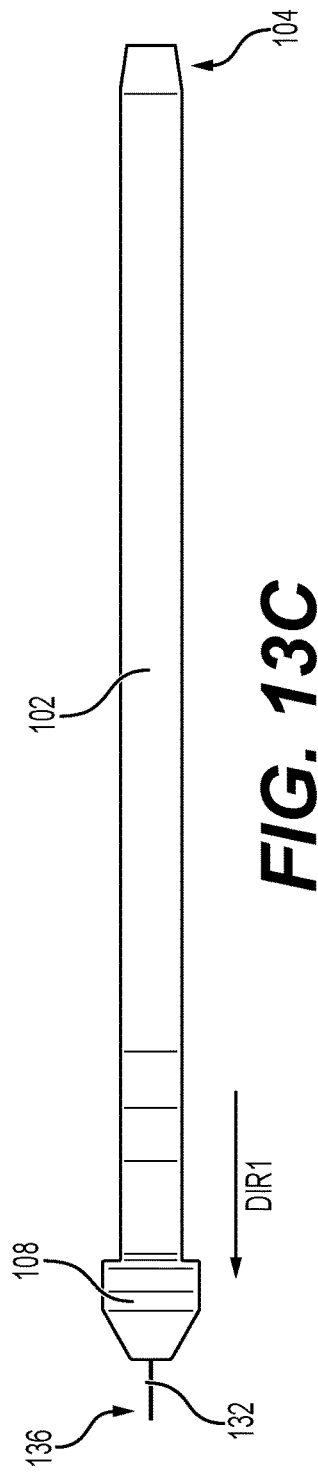

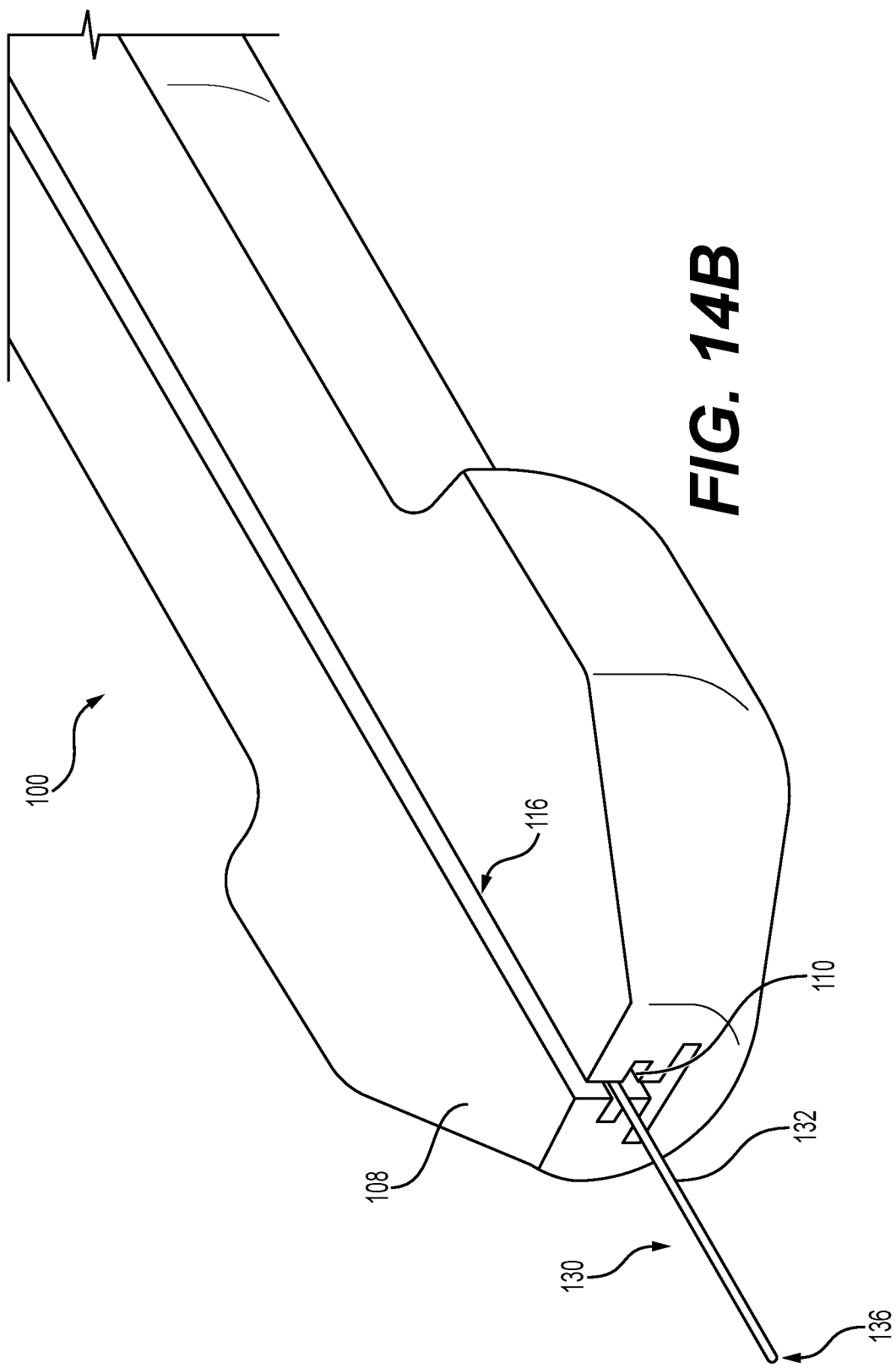

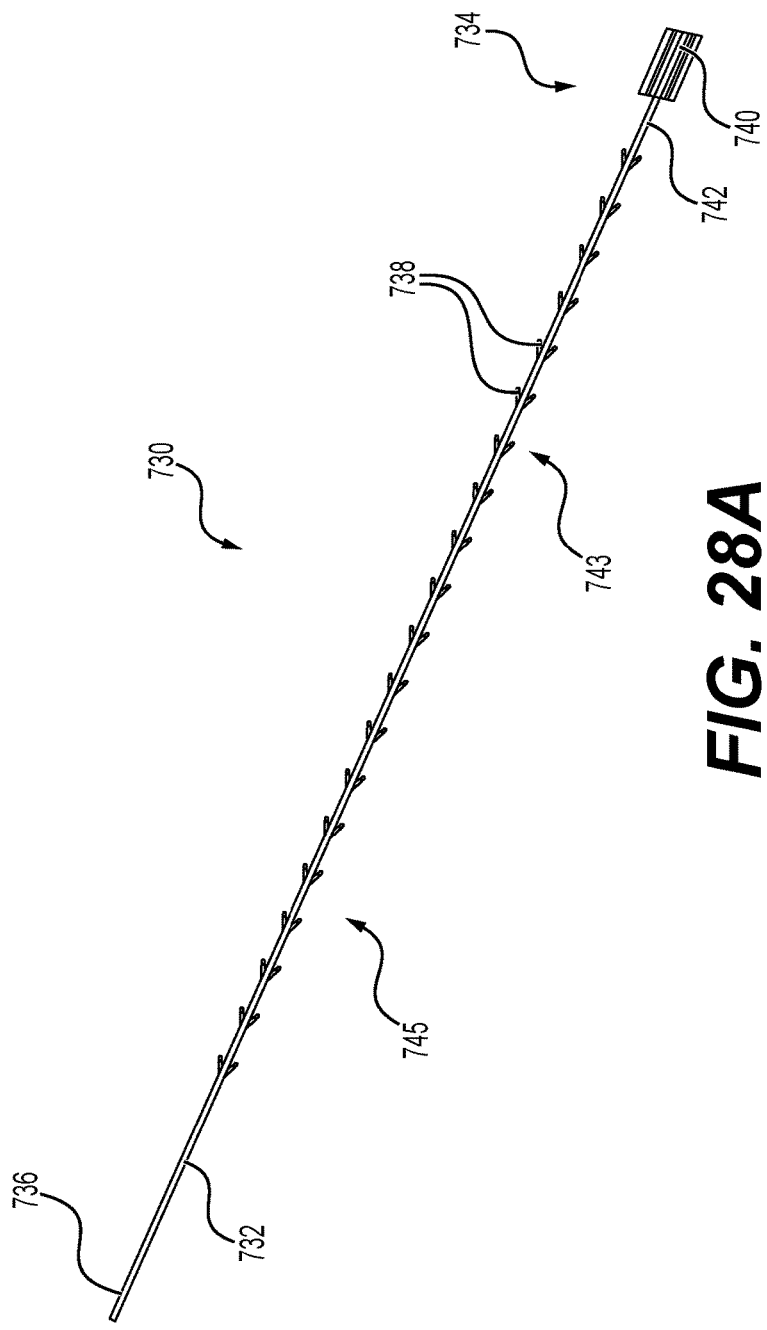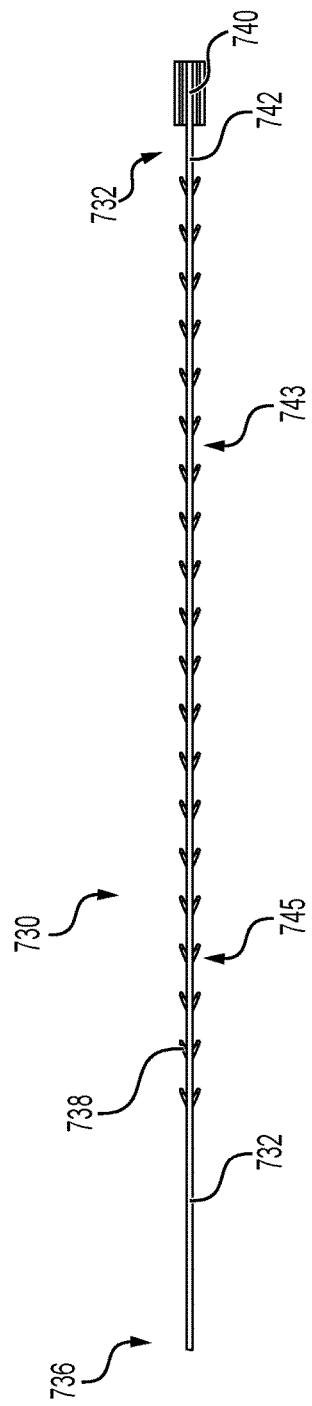
FIG. 28A
FIG. 28B

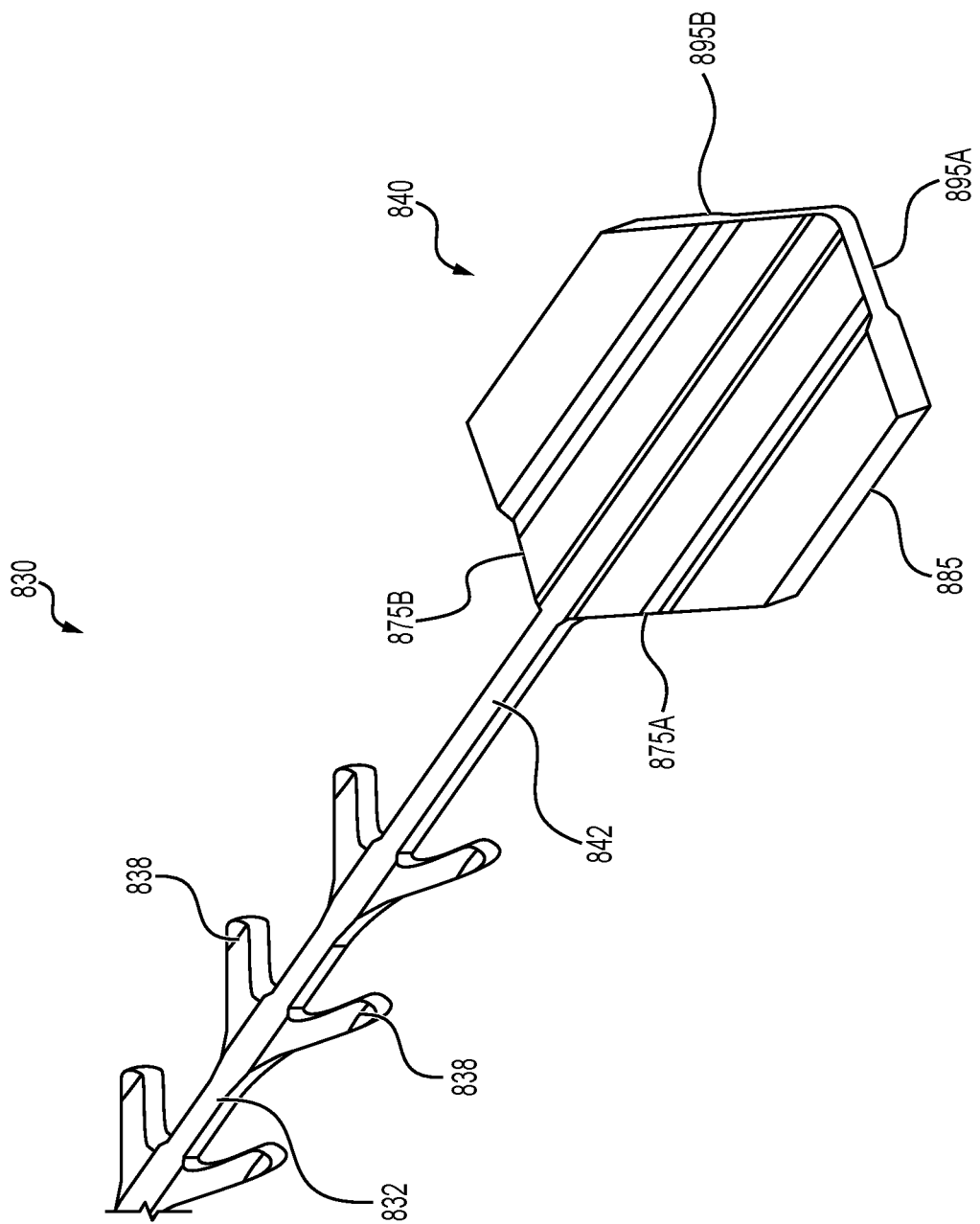

CARTRIDGES WITH FIRST AND SECOND CHANNELS FOR GUIDING BARBED SUTURES HAVING END EFFECTORS INTO BRAIDING MACHINES

CROSS-REFERENCE TO RELATED APPLICATIONS

The present patent application claims benefit of U.S. Provisional Application Ser. No. 63/039,649, filed on Jun. 16, 2020, the disclosure of which is hereby incorporated by reference herein. The present patent application is related to commonly assigned, U.S. patent application Ser. No. 17/336,692, filed on even date herewith, which claims benefit of U.S. Provisional Application Ser. No. 63/039,656, filed on Jun. 16, 2020, the disclosures of which are hereby incorporated by reference herein.

BACKGROUND OF THE INVENTION

Field of the Invention

The present patent application generally relates to sutures used for surgical procedures, and more specifically relates to systems, devices and methods for making braided barbed sutures.

Description of the Related Art

Surgical sutures are used to close wounds and surgical incisions, and to repair damaged muscles, vessels, and tissue. Typically, a needle is attached to one end of a surgical suture, and the needle is drawn through tissue to form one or more loops holding the tissue together. For conventional sutures, the suture is subsequently tied off in one or more knots so that the tissue will remain drawn together.

There have been a number of attempts directed to improving sutures. For example, U.S. Pat. No. 4,546,769 to Planck et al. discloses a suture including a jacket made of a tubular braided structure, such as non-crimped yarns, and a core located within the jacket containing crimped fibers. The jacket is formed by braiding the non-crimped yarns around the core, which provides a suture that is easier to bend and handle, and that makes better knots.

Although sutures are very effective for closing wounds, there are a number of challenges associated with using conventional sutures. Many of these challenges are directly related to the knots used to secure sutures in place. If the knots are not tied properly, defects may arise including slippage, knot breakage, and re-opening of the wound. In addition, using knots to secure sutures may distort tissue, restrict blood flow, increase the formation of scars, impede wound healing, and result in infection.

In response to the above-noted deficiencies associated with conventional sutures, sutures having barbs have been developed. Unlike conventional sutures, barbed sutures have projecting barbs that allow the suture to be used to close wounds, approximate tissue, tighten tissue, and attach prosthetic devices without using knots. For example, U.S. Pat. No. 5,931,855 discloses barbed sutures that are used for cosmetic procedures such as brow-lifts and face-lifts.

One problem associated with barbed sutures is that the barbs may delaminate or separate from the core of the suture, which may lead to device failure. In response to problems encountered with barbed sutures, braided barbed sutures having more durable barbs have been developed. For example, U.S. Pat. No. 8,663,277 to Collier et al., assigned to Ethicon, Inc., discloses a braided barbed suture that provides a 96% improvement in holding strength compared to a barbed monofilament.

Efforts directed to making braided, barbed sutures include manually delivering a barbed filament into a braiding filament assembly. Traditional braiding procedures require an operator to adhere to a complex series of steps including running a braider to form a first length of unbarbed suture, turning the braider off, positioning a barbed filament at the braider eyelet where the filaments converge at the braid point, then turning the braider back on and allowing the filaments to draw the barbed filament into the braid. In addition, the barbed insert material being braided is greatly affected by the filaments themselves or by the vibration created as a result of braiding. The vibration generated by the braiding equipment can result in the barbed material whipping, twisting, getting caught in the filaments, and/or accumulating undesirable rotation.

In order to improve the quality of braided, barbed sutures, there have been some efforts directed to maintaining control of the barbed filament during a braiding procedure. For example, U.S. Pat. Nos. 8,210,085, 8,733,223, and 9,206,535, assigned to Ethicon, Inc., the disclosures of which are hereby incorporated by reference herein, disclose an automated system for making braided barbed sutures including a braiding filament assembly, and a guide assembly including at least one barbed insert dispenser opening defining a passageway for orienting a barbed insert. The guide assembly is adapted to dispense at least one barbed insert from the dispenser opening into the braiding filament assembly for braiding a plurality of filaments around the at least one barbed insert for making a braided barbed suture. The passageway of the dispenser opening is adapted to allow longitudinal movement of the barbed insert relative to the passageway while simultaneously preventing twisting movement of the barbed insert relative to the passageway. The passageway includes an elongated slit having a greater width than height.

Introducing a barbed suture unaided into a braiding apparatus, the barbed suture having an elongated core and barbs projecting outwardly from the elongated core, results in an uneven braid structure around the elongated core due to vibration imparted from the braiding apparatus to the elongated core. The vibration generated by the braiding equipment can result in the barbed material whipping, twisting, getting caught in the filaments, or accumulating undesired rotation. Moreover, attempting to braid barbed sutures having an end effector at a proximal end of the elongated core poses a challenge because the width of the end effector is greater than the width of the barbed portion of the elongated core. Because of this, if a delivery cartridge for a barbed suture has only a single pathway therethrough, the delivery cartridge cannot frictionally engage both the barbed section of the barbed suture and the end effector of the barbed suture at the same time.

Thus, in spite of the above advances, there remains a need for improved systems, devices and methods for making braided, barbed sutures. There also remains a need for a cartridge that is able to accommodate a barbed monofilament core with an end effector secured to an end of the monofilament core. In addition, there is a need for a cartridge that holds a barbed suture for introducing the barbed suture into a braider, whereby the cartridge has two different channels, tracks and/or pathways to separately accommodate the barbed portion of the barbed suture and the end effector portion of the barbed suture.

In addition, there remains a need for a cartridge that provides for frictional engagement of the barbed section of a barbed suture and, separately, the end effector section of the barbed suture. Moreover, there is a need for a cartridge having a distal end with a larger diameter head that holds the cartridge so that it extends from a distal end of a guide tube by a predetermined distance. Furthermore, there remains a need for a cartridge that solves the problem of an end effector of a barbed suture being laterally displaced when the braiding is applied to the barbed suture.

SUMMARY OF THE INVENTION

In one embodiment, a device, such as a cartridge, is used to deliver a barbed suture into a braider. In one embodiment, the device preferably includes an elongated body having a first channel having a proximal end, a distal end, a first width, and a first opening at a distal end of the cartridge, and a second channel having a proximal end, a distal end, a second width, and a second opening at the distal end of the cartridge, whereby the first channel is dimensioned to frictionally engage a barbed section of the barbed suture, and the second channel is larger than the first channel and is dimensioned to frictionally engage an end effector secured to the proximal end of an elongated core of the barbed suture. In one embodiment, the end effector may include a loop, a button, a tab, a t-tag, and/or an end effector located at the proximal end of the elongated core of the barbed suture.

In one embodiment, the device for guiding a suture into a braider preferably includes a body having a proximal end, a distal end, and an axis that extends from the proximal end to the distal end. In one embodiment, the device preferably includes a first channel extending along the axis of the body and having a first distal opening at the distal end of the body, whereby the first channel has a first cross-sectional area, and a second channel extending along the axis of the body and having a second distal opening at the distal end of the body, whereby the second channel has a second cross-sectional area that is larger than the first cross-sectional area of the first channel. In one embodiment, the device preferably includes a slot extending along the axis of the body and having a distal slot opening at the distal end of the body, whereby the slot interconnects the first and second channels.

In one embodiment, the body is preferably an elongated body, and the axis is a longitudinal axis that extends from the proximal end to the distal end of the elongated body.

In one embodiment, the first channel desirably extends along the longitudinal axis of the elongated body. In one embodiment, the first channel has a width and a height defining the first cross-sectional area of the first channel.

In one embodiment, the second channel desirably extends along the longitudinal axis of the elongated body. In one embodiment, the second channel has a width and a height defining the second cross-sectional area of the second channel.

In one embodiment, the first and second channels are parallel to one another. In one embodiment, the first and second channels are spaced from one another.

In one embodiment, the elongated slot has a first end (e.g., an upper end) in communication with the first channel and a second end (e.g., a lower end) in communication with the second channel.

In one embodiment, the width of the second channel differs from the width of the first channel. In one embodiment, the height of the second channel differs from the height of the first channel. In one embodiment, the second channel has a length that is longer than or equal to the length of the first channel In one embodiment, a proximal section of the elongated body has a first outer dimension (e.g., a first outer diameter), and the distal end of the elongated body has a head having a second outer dimension (e.g., a second outer diameter) that is larger than the first outer dimension of the proximal section of the elongated body.

In one embodiment, the first channel, the second channel and the elongated slot extend through the head to the distal end of the elongated body for defining the first distal opening, the second distal opening, and the distal slot opening, respectively.

In one embodiment, the device (e.g., a cartridge) preferably includes the elongated body having a major surface that extends to the distal end of the elongated body and that overlies the first channel, and a laterally extending slot that extends from the major surface to the first channel for providing lateral access to the first channel of the elongated body.

In one embodiment, the barbed suture preferably includes an elongated core having a proximal end and a distal end, a barbed section including barbs extending outwardly from the elongated core, and an end effector (e.g., a stopper) secured to the proximal end of the elongated core. In one embodiment, the elongated core preferably includes an interconnecting segment that is distal to the end effector and proximal to the barbed section.

In one embodiment, the barbed suture may be loaded into the device (e.g., a cartridge, an elongated body, a guide) with the barbed section of the barbed suture disposed within the first channel, the end effector of the barbed suture disposed within the second channel, and the interconnecting segment of the barbed suture extending through the elongated slot.

In one embodiment, the barbed section of the barbed suture preferably defines a first cross-sectional dimension and the end effector of the barbed suture defines a second cross-sectional dimension that is larger than the first cross-sectional dimension of the barbed section of the barbed suture.

In one embodiment, the first cross-sectional dimension of the barbed section of the barbed suture desirably closely matches the first cross-sectional area of the first channel and the second cross-sectional dimension of the end effector desirably closely matches the second cross-sectional area of the second channel.

In one embodiment, a device (e.g., a cartridge) for guiding a barbed suture into a braider preferably includes an elongated body having a proximal end, a distal end, and a longitudinal axis that extends from the proximal end to the distal end of the elongated body.

In one embodiment, the device desirably includes a first channel extending along the longitudinal axis of the elongated cartridge body and having a first distal opening at the distal end of the elongated body, the first channel having a first cross-sectional area, and a second channel extending along the longitudinal axis of the elongated body and having a second distal opening at the distal end of the elongated body, the second channel having a second cross-sectional area that is larger than the first cross-sectional area of the first channel.

In one embodiment, the device desirably includes an elongated slot extending along the longitudinal axis of the elongated body that interconnects the first and second channels.

In one embodiment, a barbed suture is preferably loaded into the elongated body. In one embodiment, the barbed suture desirably includes an elongated core having a proximal end, a distal end, a barbed section including barbs extending outwardly from the elongated core, an end effector secured to the proximal end of the elongated core, and an interconnecting segment of the elongated core that is distal to the end effector and proximal to the barbed section.

In one embodiment, the barbed section of the barbed suture is preferably disposed within the first channel, the end effector of the barbed suture is preferably disposed within the second channel, and the interconnecting segment of the barbed suture preferably extends through the elongated slot.

In one embodiment, the first and second channels are parallel to one another and are spaced from one another for defining two separate paths through the elongated body of the device. In one embodiment, the second channel has a length that is longer than or equal to the length of the first channel In one embodiment, a proximal section of the elongated body of the device preferably has a first outer dimension (e.g., a first outer diameter), and the distal end of the elongated body preferably includes a head having a second outer dimension (e.g., a second outer diameter) that is larger than the first outer dimension of the proximal section of the elongated body.

In one embodiment, the first channel, the second channel and the elongated slot extend through the head to the distal end of the elongated body.

In one embodiment, the elongated body of the device preferably has a major surface that extends to the distal end of the elongated body and that overlies the first channel. In one embodiment, the device preferably has a laterally extending slot that extends from the major surface to the first channel for providing lateral access to the first channel of the elongated body.

In one embodiment, a method of making a braided barbed suture using a device (e.g., a cartridge) and a barbed suture as disclosed herein preferably includes loading the barbed suture into the device so that a distal-most tip of the elongated core extends distally beyond the distal end of the elongated body, aligning the distal end of the elongated body of the cartridge with a braiding zone of a braider for braiding around the distal-most tip of the barbed suture that extends distally beyond the distal end of the elongated body, and maintaining the distal end of the elongated body of the device in alignment with the braiding zone of the braider until the barbed suture is fully drawn into the braider.

In one embodiment, the orientation of the barbed suture relative to the cartridge may be reversed so that the end effector is the leading end of the barbed suture that is first drawn into the braiding zone of a braider followed by the barbed section of the barbed suture. In one embodiment, the end effector preferably has a lead extending from a leading end of the end effector, which is drawn first into the braiding zone of the braider, followed by the end effector, and then followed by the barbed section of the barbed suture.

In one embodiment, the aligning step of the method preferably includes disposing the elongated body in a guide tube so that the distal end of the elongated body projects beyond a distal end of the guide tube. In one embodiment, the method preferably includes after the barbed suture is fully drawn into the braider, retracting the guide tube and the elongated body disposed in the guide tube away from the braiding zone of the braider.

In one embodiment, a method of making a braided barbed suture desirably includes loading a barbed suture into the above-described device so that a small length of the elongated core extends from the distal end of the elongated body, using a guide tube to receive a proximal end of the elongated body, positioning the elongated body and the barbed suture in the device adjacent to the center of a braider, braiding around the small length that extends beyond the distal end of the elongated body, holding the guide tube in position until the barbed suture is fully drawn into the braider, and retracting the guide tube.

In one embodiment, the elongated body has a dimension (e.g., a width) at its distal end (e.g., a larger diameter head) that is greater than the dimension of a lumen of a guide tube.

In one embodiment, as the barbed suture is pulled into the braider, frictional engagement between the barbed section of the barbed suture with one of the channels and frictional engagement of the end effector with the other one of the channels is sufficient to maintain alignment of the barbed suture in a single plane, however, the frictional engagement is preferably less than the "take-up" force of the braider.

In one embodiment, the barbed suture may have an additional leader extending proximally beyond the end effector for maintaining alignment of the components of the barbed suture. In one embodiment, the additional leader may include a proximal end effector, such as a stopper.

In one embodiment, an automated braiding system preferably includes a rotatable spool having wound thereon a continuous length of barbed suture inserts, whereby each barbed suture insert has an elongated core having a proximal end and a distal end, outwardly projecting barbs and an end effector connected with the proximal end of the elongated core. In one embodiment, the barbed suture inserts preferably form a continuous length of material that may be fed into the automated braiding system to make a series of distinct, braided barbed sutures.

In one embodiment, the automated braiding system preferably includes an elongated body through which the barbed suture inserts are continuously fed. The elongated body has a first channel for the barbed sections of the barbed suture inserts and a second channel for end effectors connected with proximal ends of the respective barbed suture inserts. An end effector opening is preferably located at the proximal end of the second channel. The automated braiding system preferably includes filaments that are braided around the barbed suture inserts at a braider eyelet.

The automated braiding system may desirably include an end effector deflecting assembly that is located adjacent the proximal end of the elongated body and that is configured to deflect the end effectors into the end effector opening and the second channel of the elongated body as the continuous length of barbed suture inserts are pulled into the braider eyelet.

These and other preferred embodiments of the present invention will be described in more detail below.

BRIEF DESCRIPTION OF THE DRAWINGS

FIG. 10A is a top plan view of a barbed suture having a monofilament, barbs projecting outwardly from the monofilament, and an end effector secured to a proximal end of the monofilament, in accordance with one embodiment of the present patent application.

FIG. 10B is a magnified view of a distal end of the barbed suture shown in FIG. 10A.

FIG. 10C is a magnified view of a proximal end of the barbed suture shown in FIG. 10A.

FIG. 13A is a top plan view of the cartridge and the barbed suture shown in FIG. 12.

FIG. 13B is a side elevation view of the cartridge and the barbed suture shown in FIG. 12.

FIG. 13C is a bottom view of the cartridge and the barbed suture shown in FIG. 12.

FIG. 14B is a magnified view of the distal end of the cartridge and the barbed suture shown in FIG. 14A.

FIG. 28A is a perspective view of a barbed suture having an elongated core, barbs projecting outwardly from the elongated core, and an end effector secured to a proximal end of the elongated core, in accordance with one embodiment of the present patent application.

FIG. 28B is a top plan view of the barbed suture shown in FIG. 28A.

FIG. 29A is a perspective view of a barbed suture having an elongated core and an end effector secured to a proximal end of the elongated core, in accordance with one preferred embodiment of the present patent application.

DETAILED DESCRIPTION OF PREFERRED EMBODIMENTS

Figure 1A:
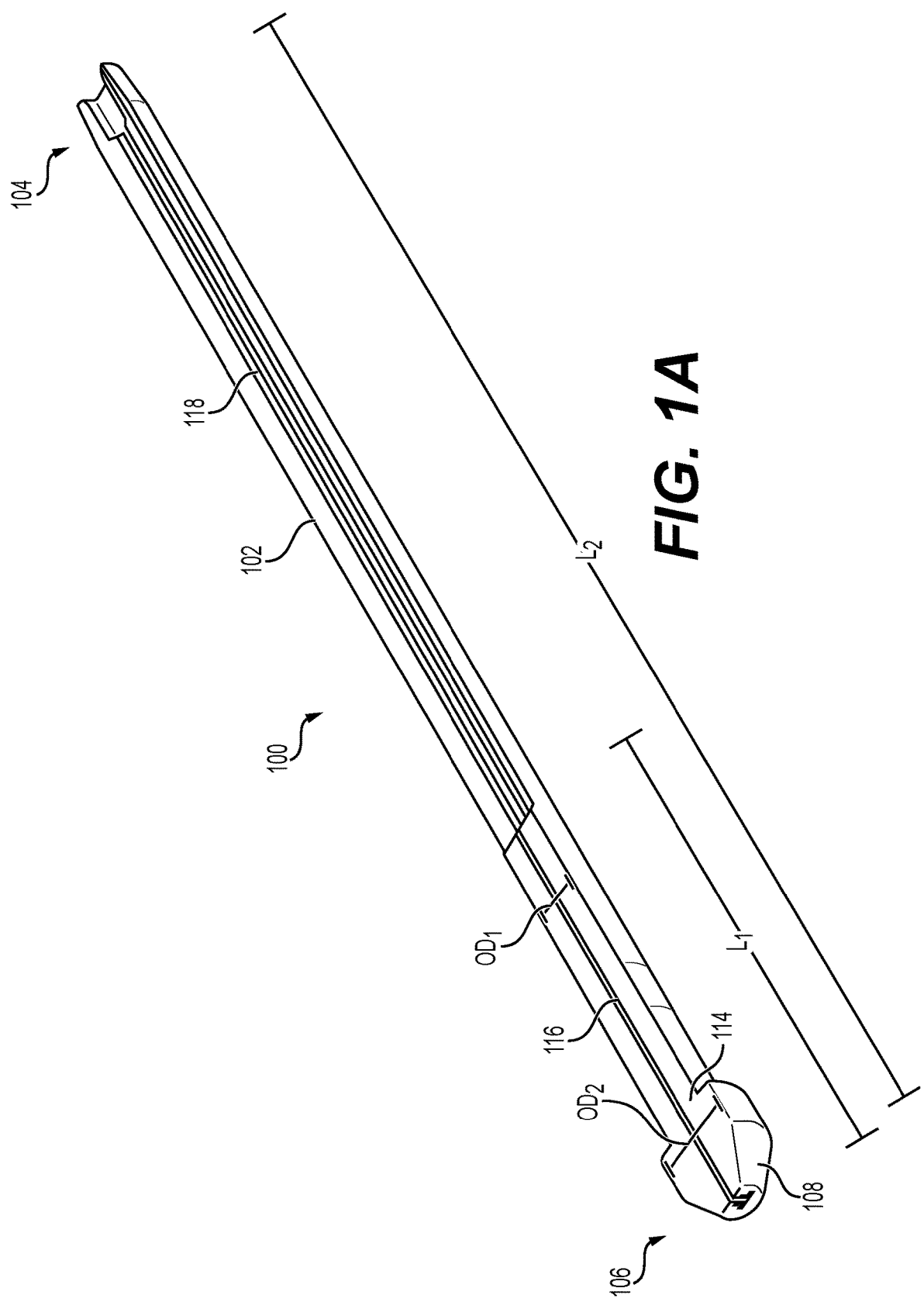
FIG. 1A is a perspective view of a cartridge used for making braided sutures, in accordance with one embodiment of the present patent application.
Figure 1B:
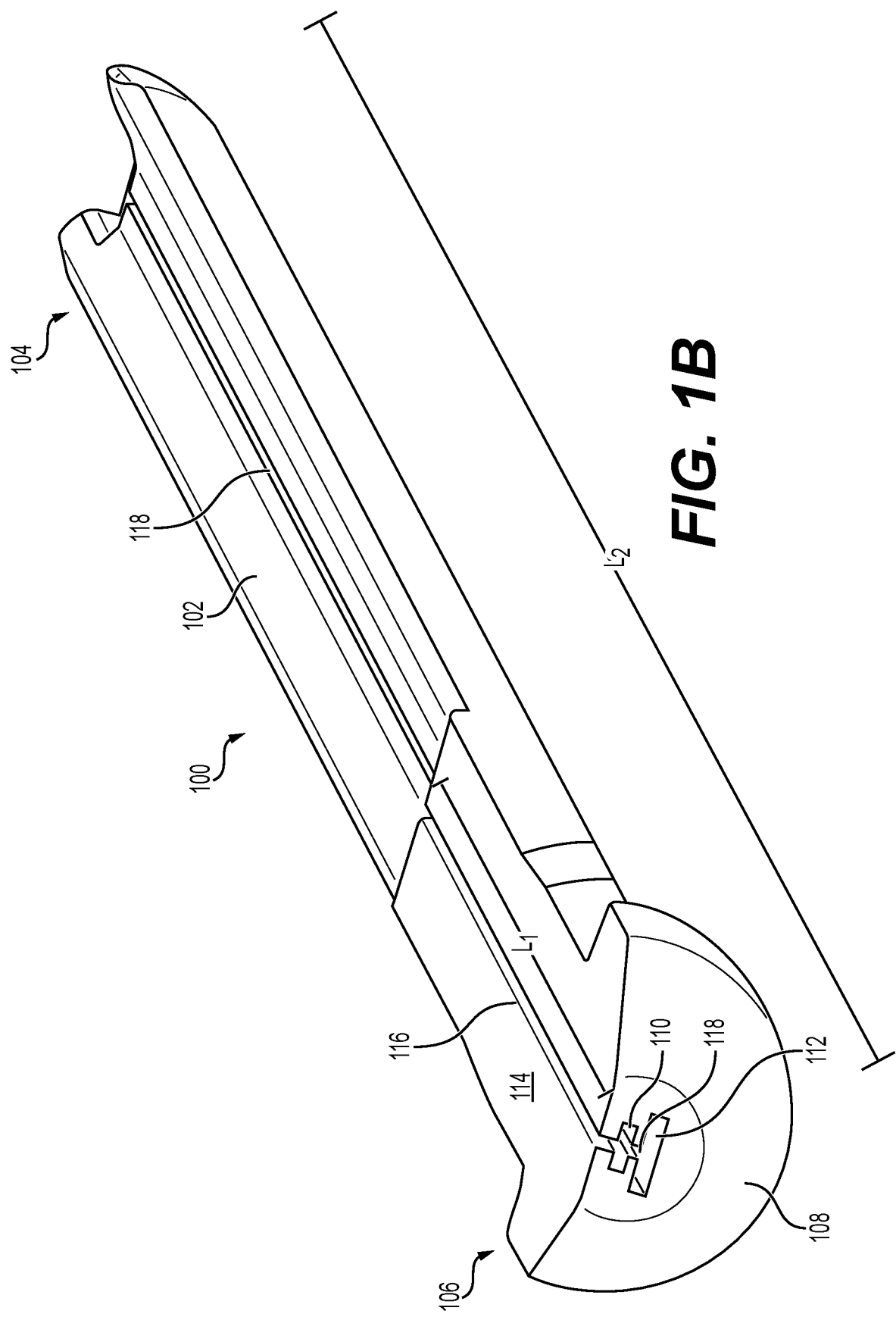
FIG. 1B is another perspective view of the cartridge shown in FIG. 1A.

Referring to FIGS. 1A and 1B, in one embodiment, a cartridge 100 that is adapted to hold a suture (e.g., a barbed suture having an end effector) for a suture braiding procedure preferably includes an elongated body 102 having a proximal end 104 and a distal end 106. In one embodiment, the cartridge 100 preferably has a head 108 located at the distal end 106 of the elongated body 102 that has a larger outer dimension (e.g., a larger outer diameter) than a proximal section of the elongated body 102.

In one embodiment, the elongated body 102 preferably has a first outer diameter $OD_1$ and the head 108 preferably has a second outer diameter $OD_2$ that is larger than the first outer diameter $OD_1$. In one embodiment, the first outer diameter of the elongated body is about 0.30 inches, and the second outer diameter $OD_2$ of the head 108 is about 0.50 inches. As will be described in more detail herein, providing a cartridge 100 with a relatively larger dimension head 108 preferably facilitates positioning and securing the cartridge 100 within a guide tube of a braiding system and prevents the head at the distal end of the cartridge from falling into and/or entering into the distal end of the guide tube.

In one embodiment, the cartridge 100 preferably includes a first channel 110 that extends to the distal end 106 of the elongated body 102, and a second channel 112 that also extends to the distal end 106 of the elongated body 102. The first and second channels 110, 112 preferably defines separate and distinct pathways through the cartridge 100. In one embodiment, the first and second channels 110, 112 desirably extend along respective axes that are parallel with one another. In one embodiment, the first and second channels have different cross-sectional dimensions. In one embodiment, the first channel is wider than high, and the second channel 112 is also wider than high.

In one embodiment, the first channel 110 preferably has a first length $L_1$ and the second channel 112 preferably has a second length $L_2$ that is greater than the first length $L_1$. In one embodiment, the first length $L_1$ of the first channel 110 may be about 2.25 inches and the second length $L_2$ of the second channel 112 is about 6.75 inches.

In one embodiment, the cartridge 100 preferably includes a major surface 114 that extends to the distal end 106 of the elongated body 102. In one embodiment, the cartridge 100 preferably includes a laterally extending slot 116 that extends from the major surface 114 to a first end (e.g., an upper end) of the first channel 110 for providing access to the first channel 110. In one embodiment, the laterally extending slot 116 has a length that matches the first length $L_1$ of the first channel 110. In one embodiment, prior to commencement of a braiding procedure, when a suture is being loaded into the cartridge 100, a distal section of the suture may be passed through the laterally extending slot 116 for positioning the distal section of the suture within the first channel 110.

In one embodiment, the cartridge 100 preferably includes an elongated slot 118 that matches the length $L_2$ of the second channel 112. In one embodiment, the elongated slot 118 extends to the distal end 106 of the elongated body 102 for interconnecting the first and second channels 110, 112 adjacent the distal end 106 of the elongated body 102.

Figure 2A:
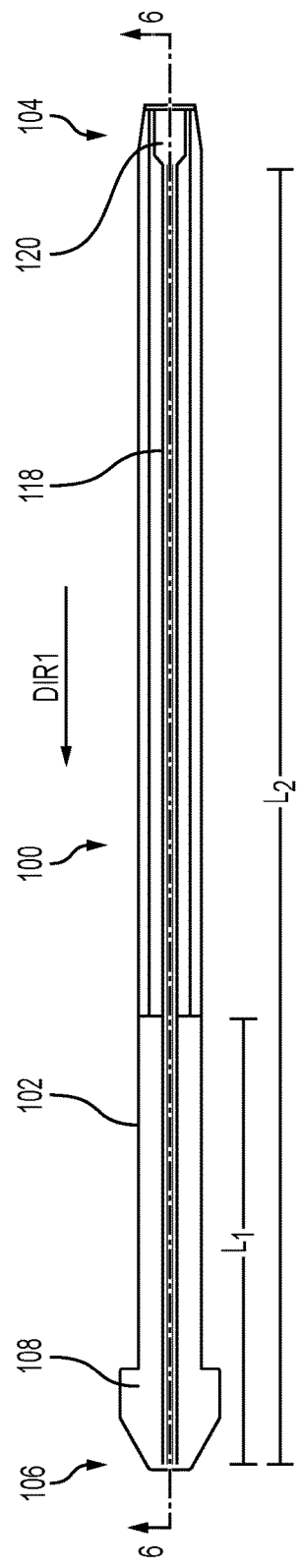
FIG. 2A is a top plan view of the cartridge shown in FIGS. 1A and 1B.
Figure 2B:
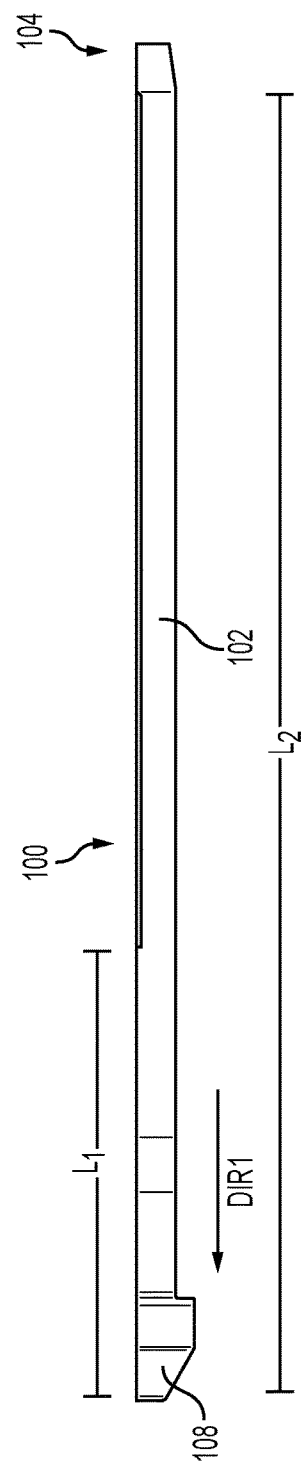
FIG. 2B is a side elevation view of the cartridge in shown in FIGS. 1A and 1B.
Figure 2C:
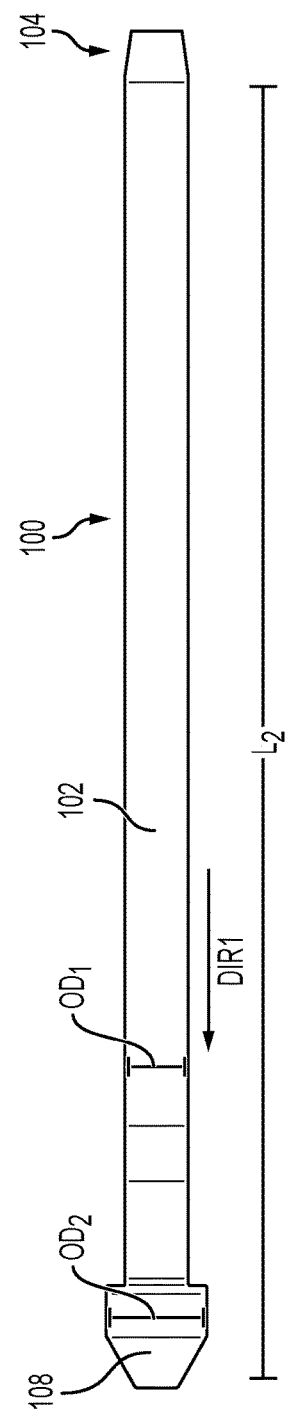
FIG. 2C is a bottom view of the cartridge shown in FIGS. 1A and 1B.

Referring to FIGS. 2A-2C, in one embodiment, the elongated body 102 of the cartridge 100 preferably includes the proximal end 104, the distal end 106, and the larger diameter head 108 that is adjacent the distal end. In one embodiment, the first channel 110 (FIG. 1B) and the laterally extending slot 116 have similar lengths $L_1$ of about 2.25 inches. In one embodiment, the second channel 112 (FIG. 1B) and the elongated slot 118 have similar lengths $L_2$ of about 6.75 inches.

Referring to FIG. 2A, in one embodiment, the proximal end 104 of the elongated body 102 desirably includes an end effector opening 120 that is preferably adjacent the proximal end of the second channel 112 (FIG. 1B) and that is adapted to receive an end effector located at a proximal end of a suture (e.g., a barbed suture). In one embodiment, the end effector of the suture is adapted to be pulled distally (i.e., in the distal direction DIR1) through the second channel 112 (FIG. 1B) while a distal section of the suture is pulled through the first channel 110 (FIG. 1B) of the cartridge 100. In one embodiment, an interconnecting segment of the suture that is distal to the end effector preferably interconnects the end effector with the distal section of the suture. In one embodiment, the interconnecting segment preferably passes through the elongated slot 118 of the cartridge 100 as the suture is pulled distally in the direction DIR1 through the first and second channels 110, 112 (FIG. 1B) of the cartridge 100.

Figure 3:
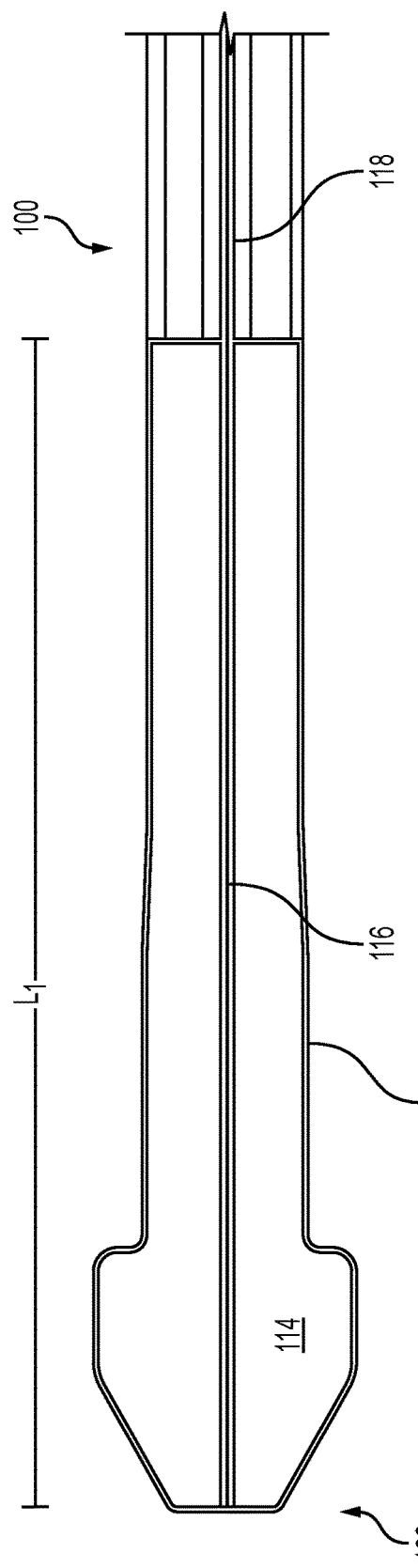
FIG. 3 is a top plan view of a distal end of the cartridge shown in FIGS. 1A-1B and 2A-2C.

Referring to FIG. 3, in one embodiment, the first channel 110 (FIG. 1B) of the cartridge 100 extends to the distal end 106 of the elongated body 102 and has the first length $L_1$ of about 2.25 inches. The cartridge 100 desirably includes the laterally extending slot 116 that extends from the major surface 114 to the first channel for enabling a distal end of a suture to be positioned within the first channel. The cartridge desirably includes the elongated slot 118 that extends along the length of the elongated body 102 for interconnecting the first and second channels 110, 112 (FIG. 1B), preferably where the first and second channels overlap near the distal end 106 of the elongated body 102 of the cartridge 100.

Figure 4:
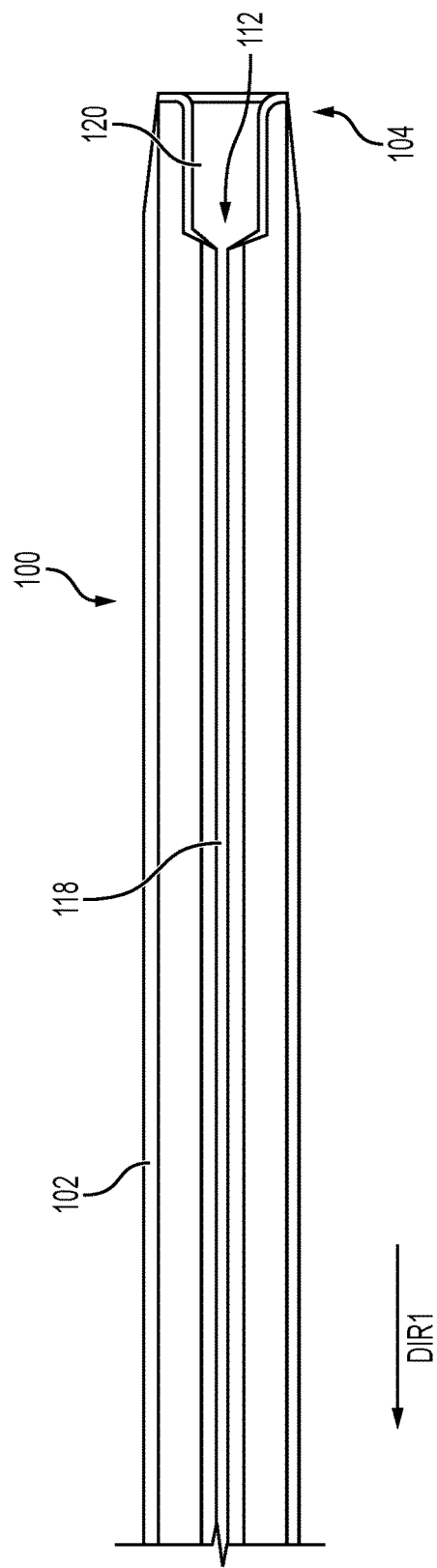
FIG. 4 is a top plan view of a proximal end of the cartridge shown in FIGS. 1A-1C and 2A-2C.

Referring to FIG. 4, in one embodiment, the elongated slot 118 preferably extends between the proximal end 104 of the elongated body 102 and the distal end 106 (FIG. 3) of the elongated body. The elongated slot 118 preferably interconnects the first and second channels 110, 112 (FIG. 1B) for enabling the end effector of the suture to move distally (e.g., in the direction DIR1) within the second channel 112 (FIG. 1B) while the distal section of the suture that includes barbs is pulled through the first channel 110 (FIG. 1B) of the cartridge 100. In one embodiment, an end-effector (e.g., a stopper) secured to a proximal end of a suture (e.g., a barbed suture) may be inserted into the end effector opening 120 for aligning the end effector of the suture with the second channel 112 (FIG. 1B) of the cartridge 100.

Figure 5A:
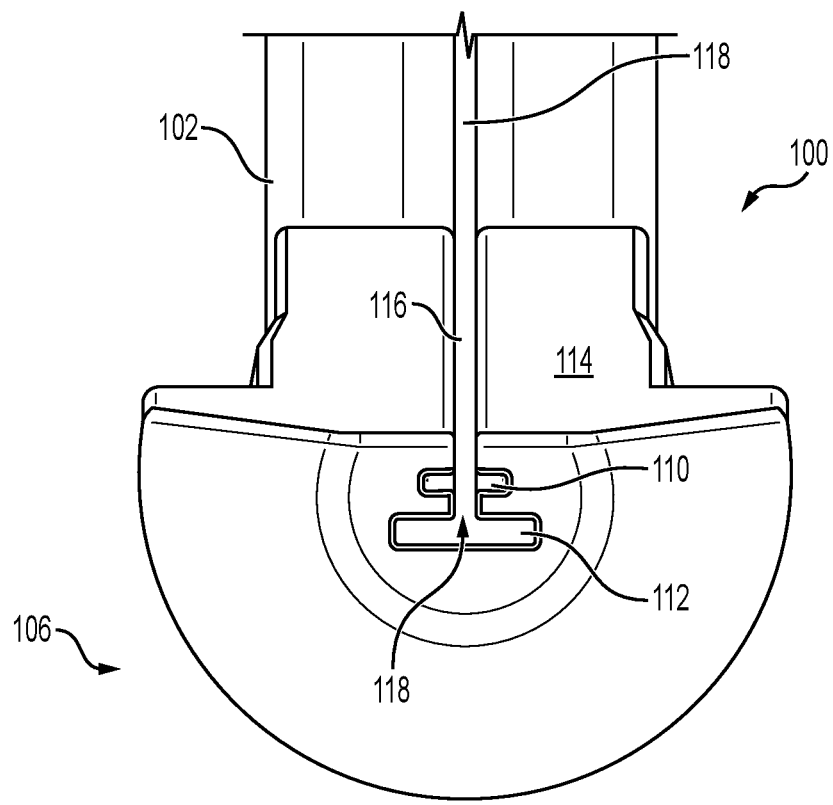
FIG. 5A is a perspective view of a distal end of the cartridge shown in FIGS. 1A-1B and 2A-2C.
Figure 5B:
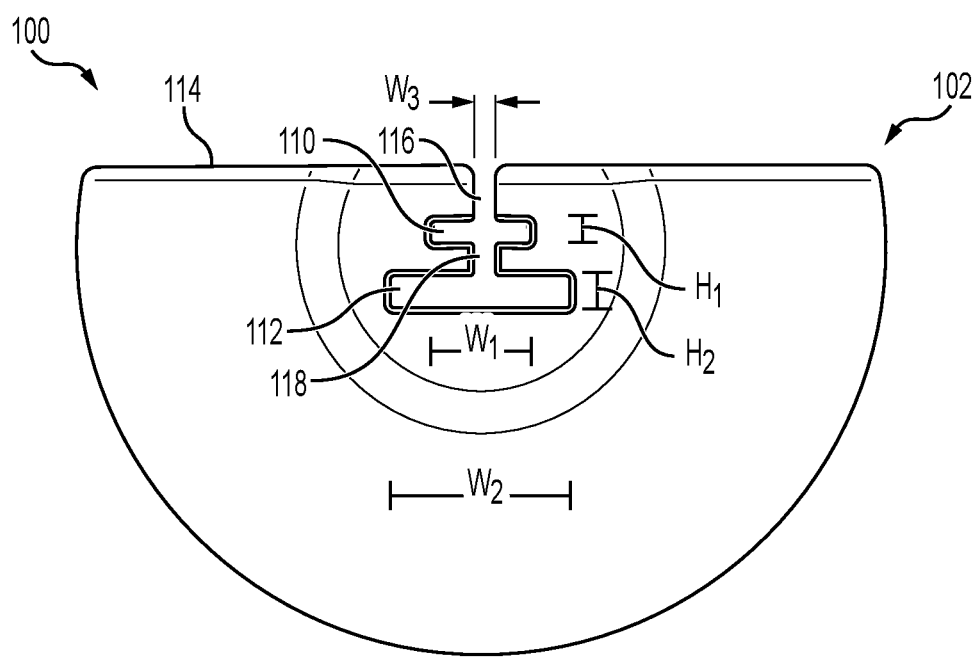
FIG. 5B is a distal end view of the cartridge shown in FIGS. 1A-1B and 2A-2C.

Referring to FIGS. 5A and 5B, in one embodiment, the cartridge 100 preferably includes the first channel 110 that extends to the distal end 106 of the elongated body 102, and the second channel 112 that also extends to the distal end 106 of the elongated body 102. In one embodiment, the first and second channels 110, 112 preferably extend along respective axes that are parallel to one another. In one embodiment, the first and second channels 110, 112 define separate and distinct paths through the elongated body of the cartridge 100.

In one embodiment, the elongated body 102 preferably includes the major surface 114 that extends laterally across the width of the elongated body and that extends to the distal end of the elongated body. In one embodiment, the laterally extending slot 116 desirably extends from the major surface 114 to the first channel 110 of the cartridge 100 for enabling the distal end of a suture to be inserted into the first channel 110 prior to placing the cartridge 100 into a braiding machine. In one embodiment, where the first and second channels 110, 112 overlap one another along the length of the first channel 110, the elongated slot 118 preferably extends from the first channel 110 and the second channel 112, which enables the interconnecting segment of the suture to pass through the elongated slot to the distal end of the elongated body of the cartridge.

In one embodiment, the first and second channels preferably have respective cross-sectional dimensions that are different. Referring to FIG. 5B, in one embodiment, the first channel 110 preferably has a width $W_1$ of about 0.086 inches and a height $H_1$ of about 0.012 inches. In one embodiment, the second channel 112 preferably has a width $W_2$ of about 0.110 inches and height $H_2$ of about 0.016 inches. In one embodiment, the laterally extending slot 116 and the elongated slot 118 desirably have similar widths $W_3$ (FIG. 5B) of about 0.010 inches. In one embodiment, as a braider pulls a distal end of a barbed suture in a distal direction through the first channel 110, the outer dimensions of the barbs of the barbed suture preferably create a slight frictional engagement with the inner surfaces of the first channel for generating a slight drag on the barbed suture. In one embodiment, as an end effector at a proximal end of the barbed suture is pulled in the distal direction through the second channel 112, the outer dimensions of the end effector preferably create a slight frictional engagement with the inner surfaces of the second channel for generating a slight drag on the end effector.

Figure 6:
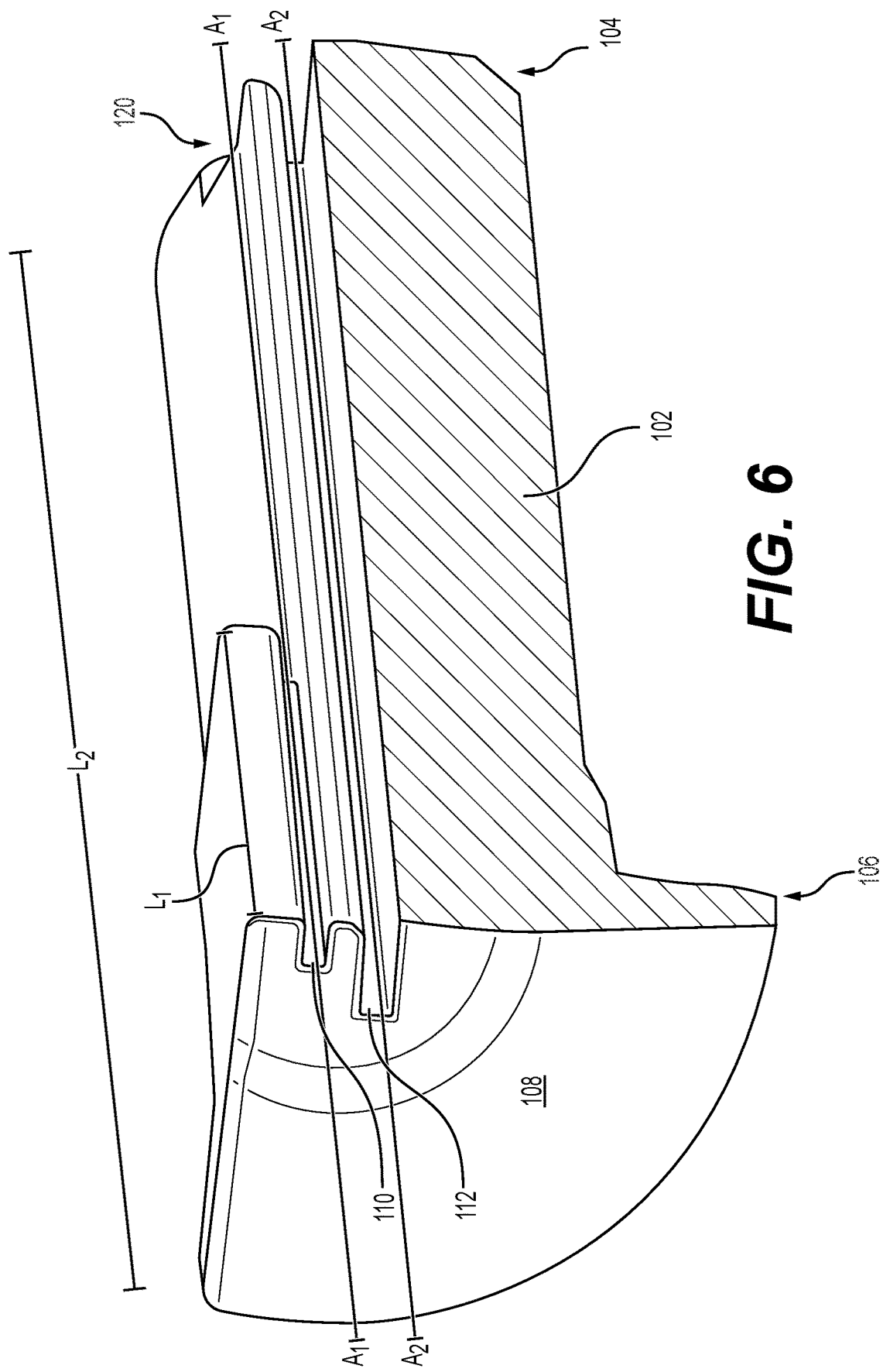
FIG. 6 is a cross-sectional view of the cartridge shown in FIG. 2A.
Figure 7:
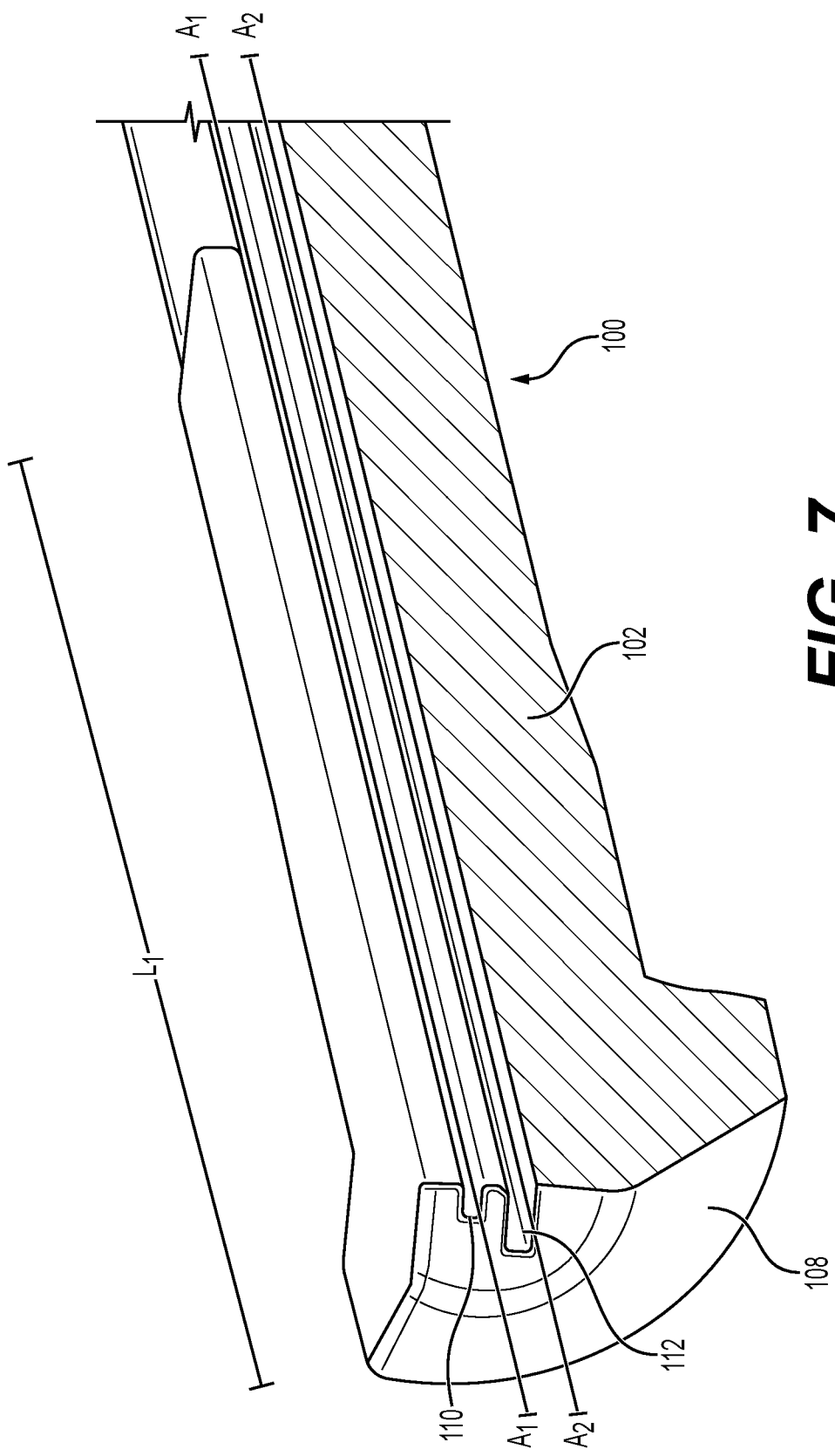
FIG. 7 is a magnified view of a distal end of the cartridge shown in FIG. 6.

Referring to FIGS. 6 and 7, in one embodiment, the elongated body 102 of the cartridge 100 has the proximal end 104 and the distal end 106 including the larger diameter head 108. The proximal end 104 of the elongated body 102 desirably includes the end effector opening 120 that is adapted to receive the end effector of a suture. The cartridge 100 preferably includes the second channel 112 that extends between the proximal end 104 and the distal end 106 of the elongated body 102. In one embodiment, the second channel 112 preferably has a length $L_2$ that extends along the longitudinal axis of the elongated body 102 of the cartridge 100. In one embodiment, the cartridge 100 preferably includes the first channel 110 that extends through a distal section of the elongated body 102. The first channel 110 preferably defines a length $L_1$ that is less than the length $L_2$ of the second channel 112 of the cartridge 100. In one embodiment, the first channel 110 preferably extends along a first axis $A_1$ and the second channel 112 preferably extends along a second axis $A_2$, which is parallel to the first axis $A_1$.

Figure 8:
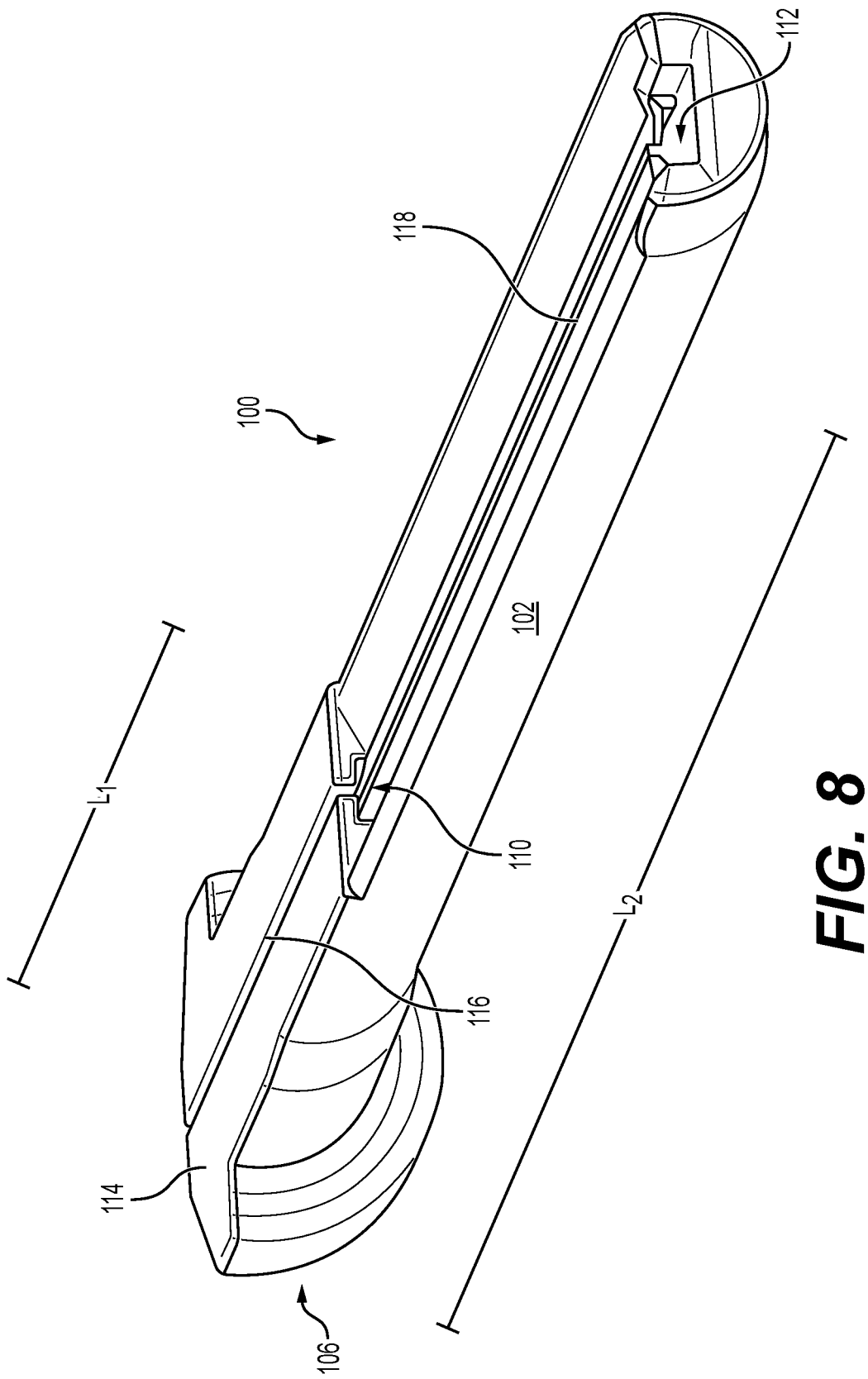
FIG. 8 is a perspective view of a proximal end of the cartridge shown in FIGS. 1A-1B and 2A-2C.

Referring to FIG. 8, in one embodiment, the cartridge 100 preferably includes the laterally extending slot 116 that extends from the major surface 114 to a first end (e.g., an upper end) of the first channel 110 for providing access to the first channel 110 via the major surface 114. The elongated slot 118 preferably interconnects the first channel 110 and the second channel 112, whereby the first and second channels overlap one another adjacent the distal end 106 of the elongated body 102. In one embodiment, the end effector at a proximal end of a suture may be inserted into the second channel 112, and the distal section of the suture that includes barbs may be passed through the laterally extending slot 116 for positioning the distal section of the suture within the first channel 110. As will be described in more detail herein, the elongated slot 118 preferably enables the end effector (e.g., a stopper) of a suture insert that is disposed within the second channel 112 to remain interconnected with the distal section of the suture that is disposed within the first channel 110.

Figure 9A:
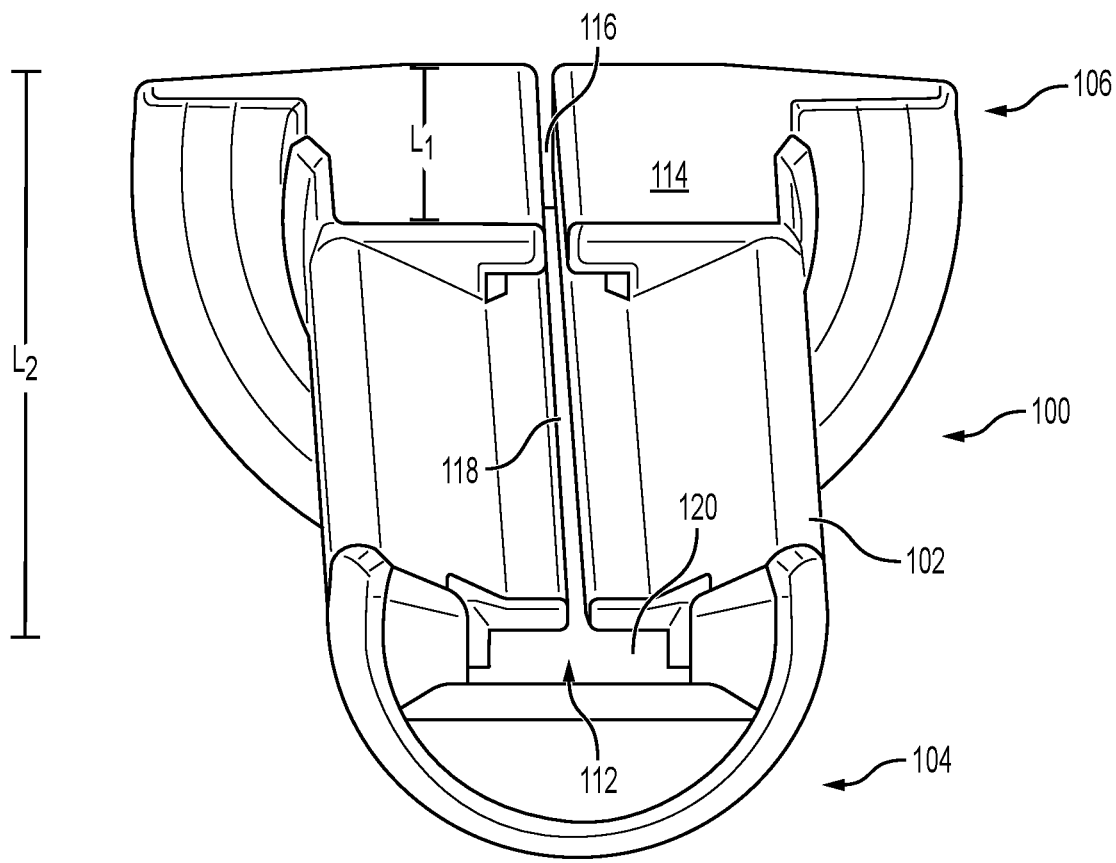
FIG. 9A is a perspective view of the proximal end of the cartridge shown in FIG. 8.
Figure 9B:
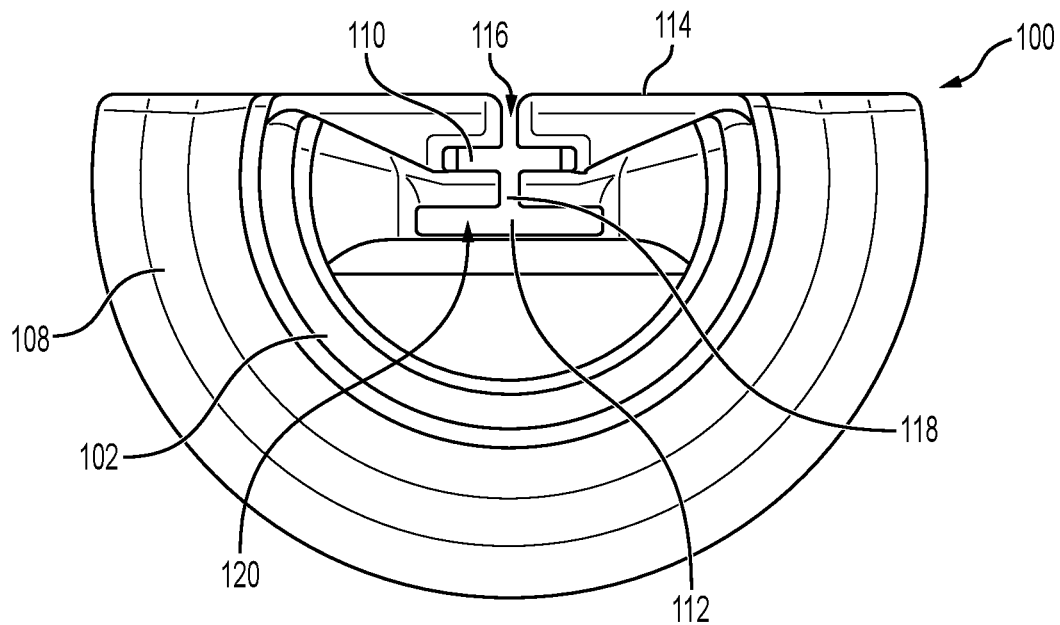
FIG. 9B is a proximal end view of the cartridge shown in FIG. 9A.

Referring to FIGS. 9A and 9B, in one embodiment, the cartridge 100 desirably includes the laterally extending slot 116 having a length $L_1$. The laterally extending slot 116 preferably extends from the major surface 114 of the elongated body 102 to the first channel 110 for enabling a distal section of a suture to be disposed within the first channel 110. In one embodiment, the cartridge 100 preferably includes the elongated slot 118 that has a length $L_2$ that is greater than the length $L_1$ of the laterally extending slot 116. The portions of the first and second channels 110, 112 that overlap one another are preferably interconnected by the elongated slot 118, which enables an interconnecting segment of the suture to pass through the elongated slot 118 while the end effector is pulled through the second channel 112 and the distal section of the suture is pulled through the first channel 110. The proximal end 104 of the elongated body 102 preferably includes the end effector opening 120 that enables the end effector at a proximal end of a suture to be inserted into the second channel 112 of the cartridge 100.

In one embodiment, a suture (e.g., a barbed suture) may be loaded into the cartridge 100 by inserting the end effector of the suture into the end effector opening 120 located adjacent the proximal end of the second channel 112, and passing the distal end of the suture through the laterally extending slot 116 for positioning a distal section of the suture within the first channel 110. An interconnecting segment of the elongated core of the suture that is distal to the end effector preferably passes through the elongated slot 118 for enabling the end effector of the suture to be pulled through the second channel 112 while the distal section of the suture is pulled through the first channel 110.

Referring to FIGS. 10A-10C, in one embodiment, a suture 130 is adapted to be loaded into the cartridge 100 (FIGS. 1A and 1B) shown and described herein. In one embodiment, the suture 130 is preferably a barbed suture including an elongated core 132 having a proximal end 134 and a distal end 136. In one embodiment, the barbed suture 130 preferably includes a plurality of barbs 138 that project outwardly from opposite sides of the elongated core 132. In one embodiment, the distal end 136 of the elongated core 132 may be devoid of barbs. The barbed suture 130 preferably includes an end effector 140 that is secured to the proximal end 134 of the elongated core 132. In one embodiment, the barbed suture 130 preferably includes an interconnecting segment 142 that is located between the end effector 140 and the barbs 138 that extend from the elongated core 132. In one embodiment, the barbed suture 130 preferably includes a proximal barbed section 143 that is distal to the interconnecting segment 142 and a distal barbed section 145 that is distal to the proximal barbed section 143. In one embodiment, a midway point that is about halfway along the length of the elongated core 132 may divide the proximal barbed section 143 from the distal barbed section 145.

In one embodiment, the end effector 140 may be a stopper tab having a diamond-like shape, which has a shape and configuration that is designed to facilitate smooth transition of the braided filaments from the elongated core of the barbed suture onto the leading portion of the flattened, stopper tab as well as the transition from the trailing portion of the flattened, stopper tab back to the non-barbed, leading end of the elongated core of the next barbed suture. The angle of the leading portion of the diamond-shaped stopper tab preferably complements that of the braid point where the filaments converge maintaining the stopper tab in the center of the braiding zone and allowing for balanced coverage of the tab.

Figure 11:
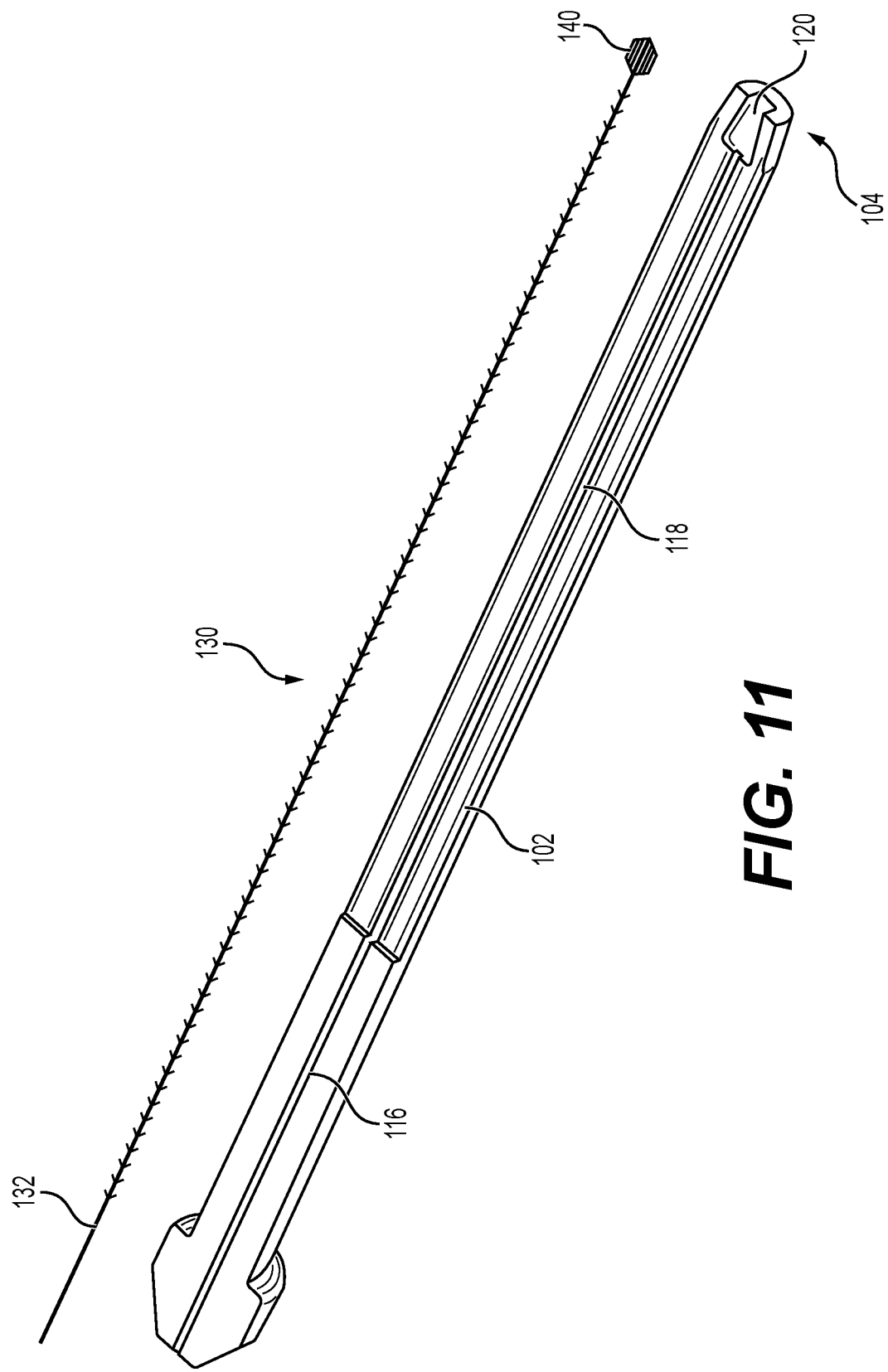
FIG. 11 is a perspective view of a cartridge and a barbed suture that is configured for being loaded into the cartridge, in accordance with one embodiment of the present patent application.
Figure 12:
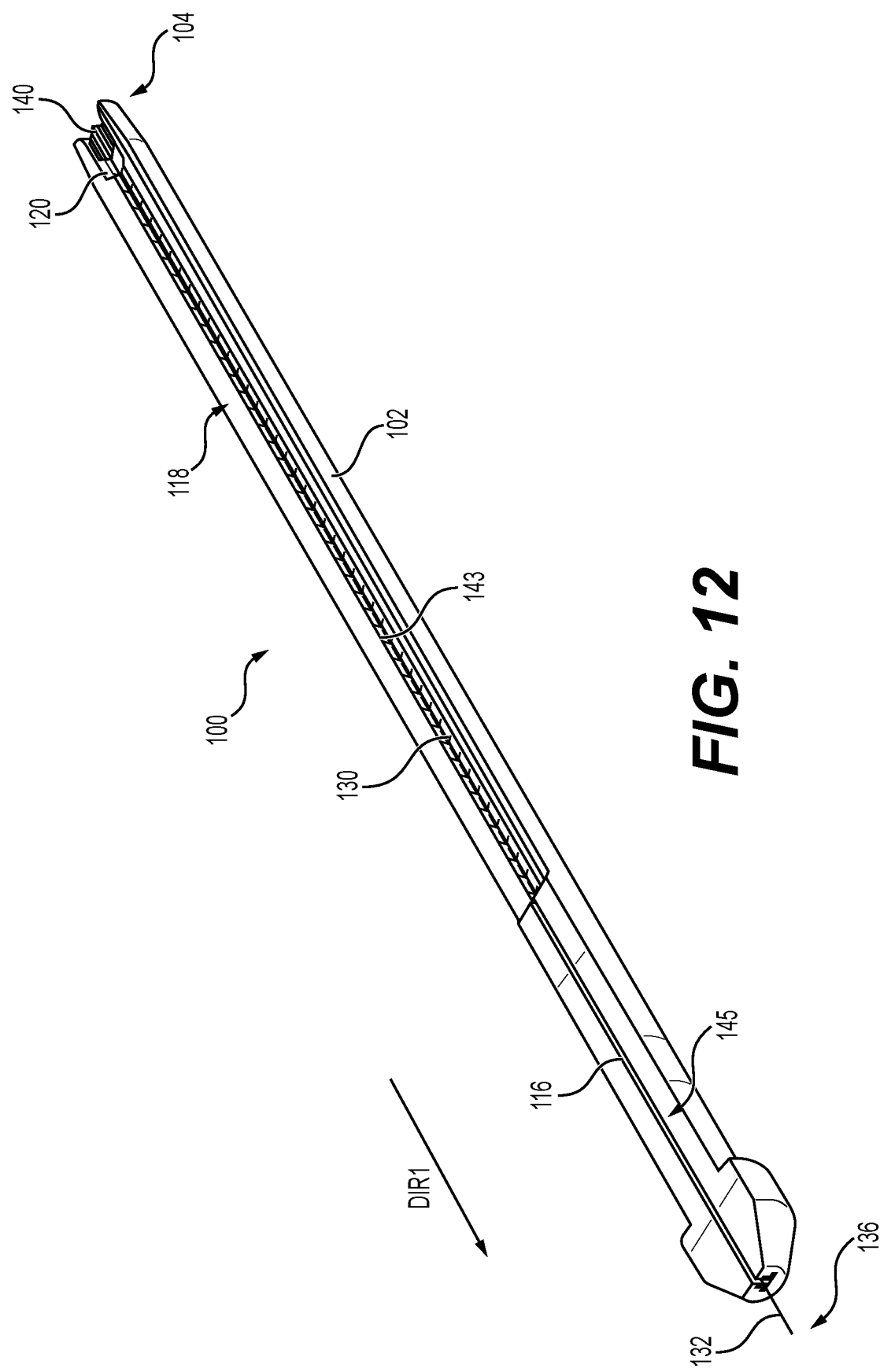
FIG. 12 is a perspective view of the cartridge and the barbed suture of FIG. 11 after the barbed suture has been loaded into the cartridge, in accordance with one embodiment of the present patent application.

Referring to FIG. 11, in one embodiment, in order to load the barbed suture 130 into the cartridge 100, the barbed suture 130 is preferably positioned adjacent the cartridge 100 (FIGS. 1A and 1B) with the end effector 140 aligned with the end effector opening 120 located at the proximal end 104 of the elongated body 102. The longitudinal axis of the elongated core 132 of the barbed suture 130 is preferably aligned with the first and second elongated slots 116, 118 that extend along the length of the elongated body 102.

Referring to FIGS. 12 and 13A-13C, in one embodiment, the end effector 140 of the barbed suture 130 may be inserted into the end effector opening 120 located at the proximal end 104 of the elongated body 102 of the cartridge 100. The distal end 136 of the elongated core 132 is preferably passed through the laterally extending slot 116 of the cartridge 100 for positioning the distal barbed section 145 (FIG. 10A) of the barbed suture 130 within the first channel 110 (FIG. 5B) of the cartridge 100. After the barbed suture is loaded into the cartridge 100, the end effector 140 is preferably positioned within the second channel 112 (FIG. 5B) of the cartridge, the proximal barbed section 143 of the barbed suture 130 that is distal to the end effector 140 preferably overlies the elongated slot 118 and the second channel 112 (FIG. 5B) of the cartridge 100, and the distal barbed section 145 (FIG. 10A) of the barbed suture 130 is preferably positioned within the first channel 110 (FIG. 5B) of the cartridge 100, where it also overlies the elongated slot 118 and the second channel 112 (FIG. 5B) of the cartridge 100.

In one embodiment, the interconnecting segment 142 (FIG. 13A) of the elongated core 132 preferably passes through the elongated slot 118 of the elongated body 102 for interconnecting the end effector 140 with the proximal and distal barbed sections 143, 145 of the barbed suture 130 as the barbed suture and the end effector are pulled through the cartridge 100 in the distal direction designated DIR1. In one embodiment, when the barbed suture 130 is loaded into the cartridge 100, the distal end 136 of the elongated core 132 of the barbed suture 130 preferably extends distally beyond the distal end of the head 108 of the elongated body 102 for being engaged by a braiding machine. In one embodiment, during a braiding procedure, with the cartridge 100 held in a stationary position (e.g., by a guide tube), a braiding system preferably engages the distal end 136 of the elongated core 132 for pulling the barbed suture in the distal direction DIR1 to pull the barbed suture into the braider and remove the barbed suture from the cartridge.

Figure 14A:
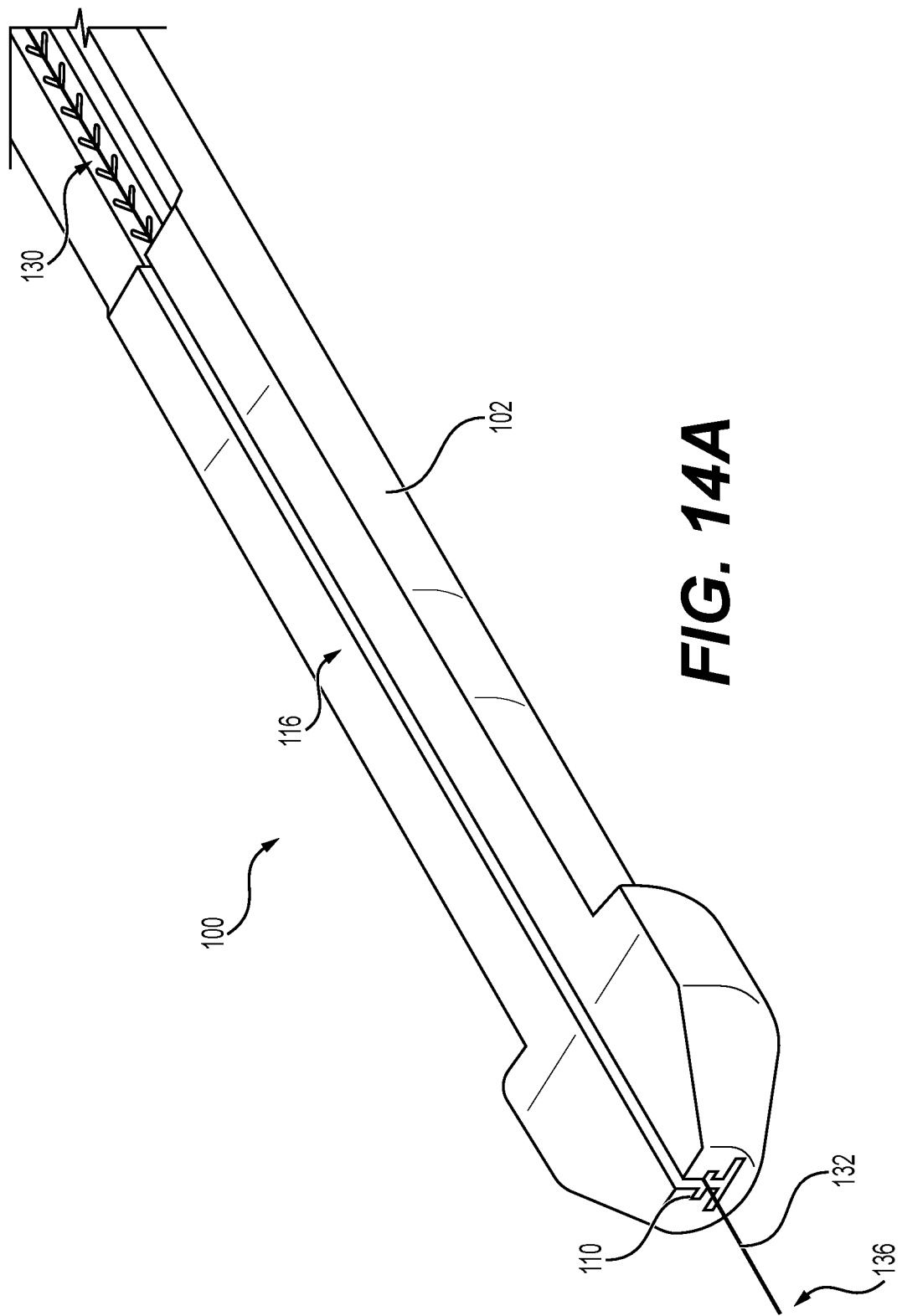
FIG. 14A is a perspective view of a distal end of the cartridge shown in FIGS. 12 and 13A-13C with a distal end of a barbed suture projecting distally beyond a distal-most end of the cartridge, in accordance with one embodiment of the present patent application.
Figure 14C:
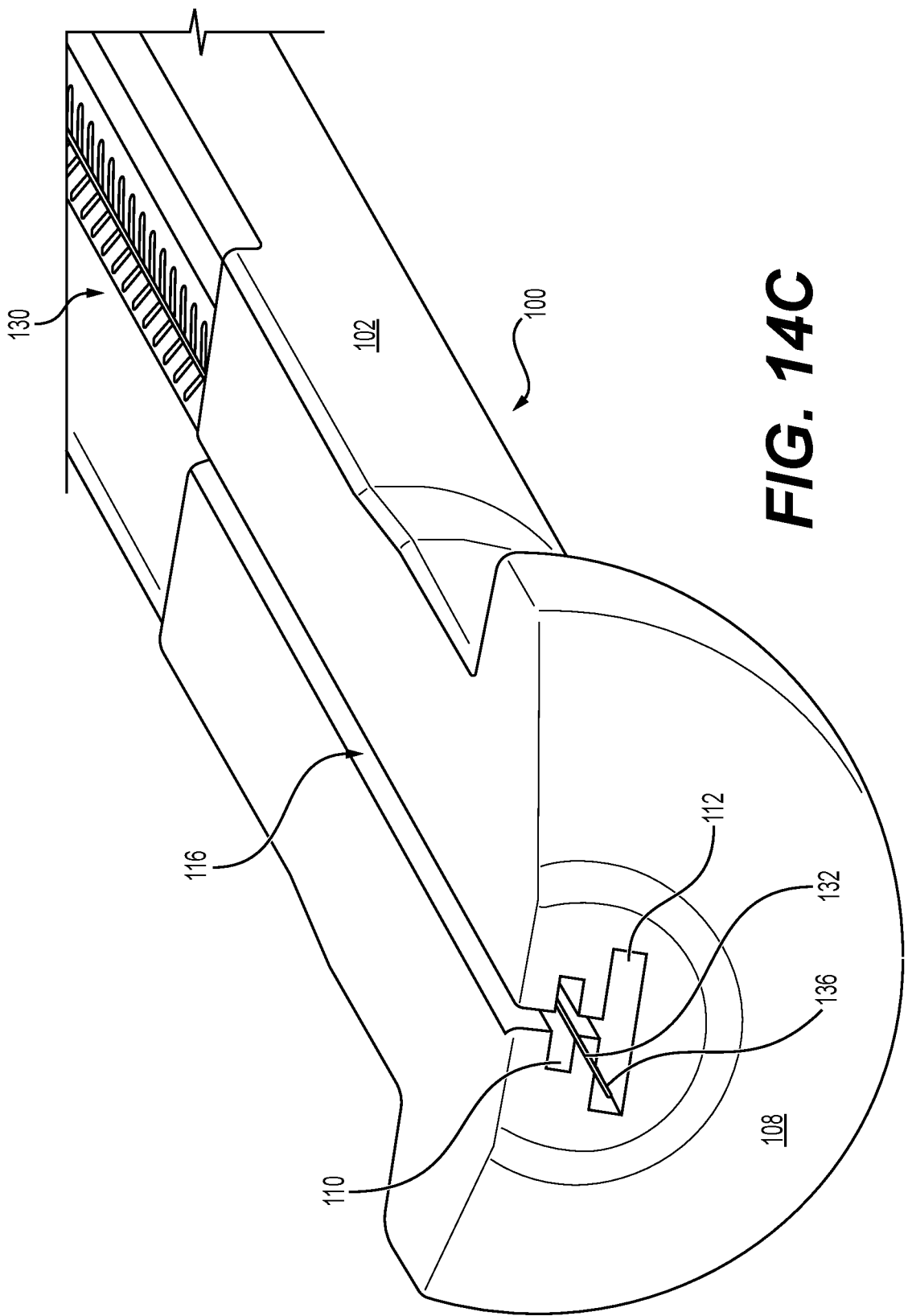
FIG. 14C is another magnified view of the distal end of the cartridge and the barbed suture shown in FIG. 14A.

Referring to FIGS. 14A-14C, in one embodiment, when loading the barbed suture 130 into the cartridge 100, a distal section (e.g., the distal barbed section 145 shown in FIG. 10A) of the barbed suture 130 may be passed through the laterally extending slot 116 for positioning the barbed distal section of the barbed suture 130 with the first channel 110 of the cartridge 100. In one embodiment, after the barbed suture has been loaded into the cartridge, the distal end 136 of the elongated core 132 of the barbed suture 130 preferably extends distally beyond the distal end of the head 108 of the cartridge 100, whereby the distal end 136 of the elongated core 132 may be grasped by a braider for drawing the barbed suture out of the cartridge and into a braiding assembly for braiding the barbed suture.

Figure 15A:
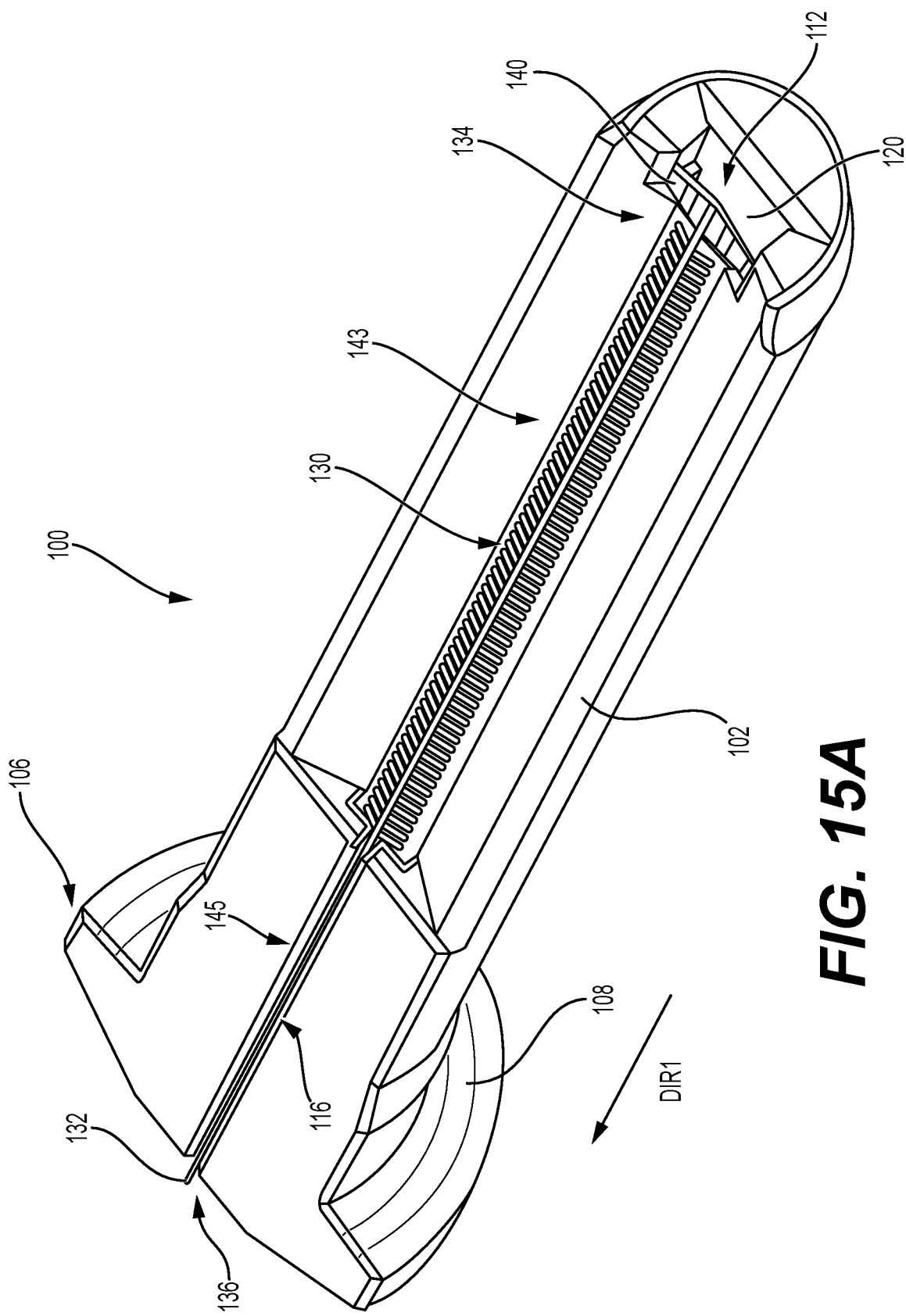
FIG. 15A is a perspective top side view of the cartridge and the barbed suture shown in FIGS. 13A-130.
Figure 15B:
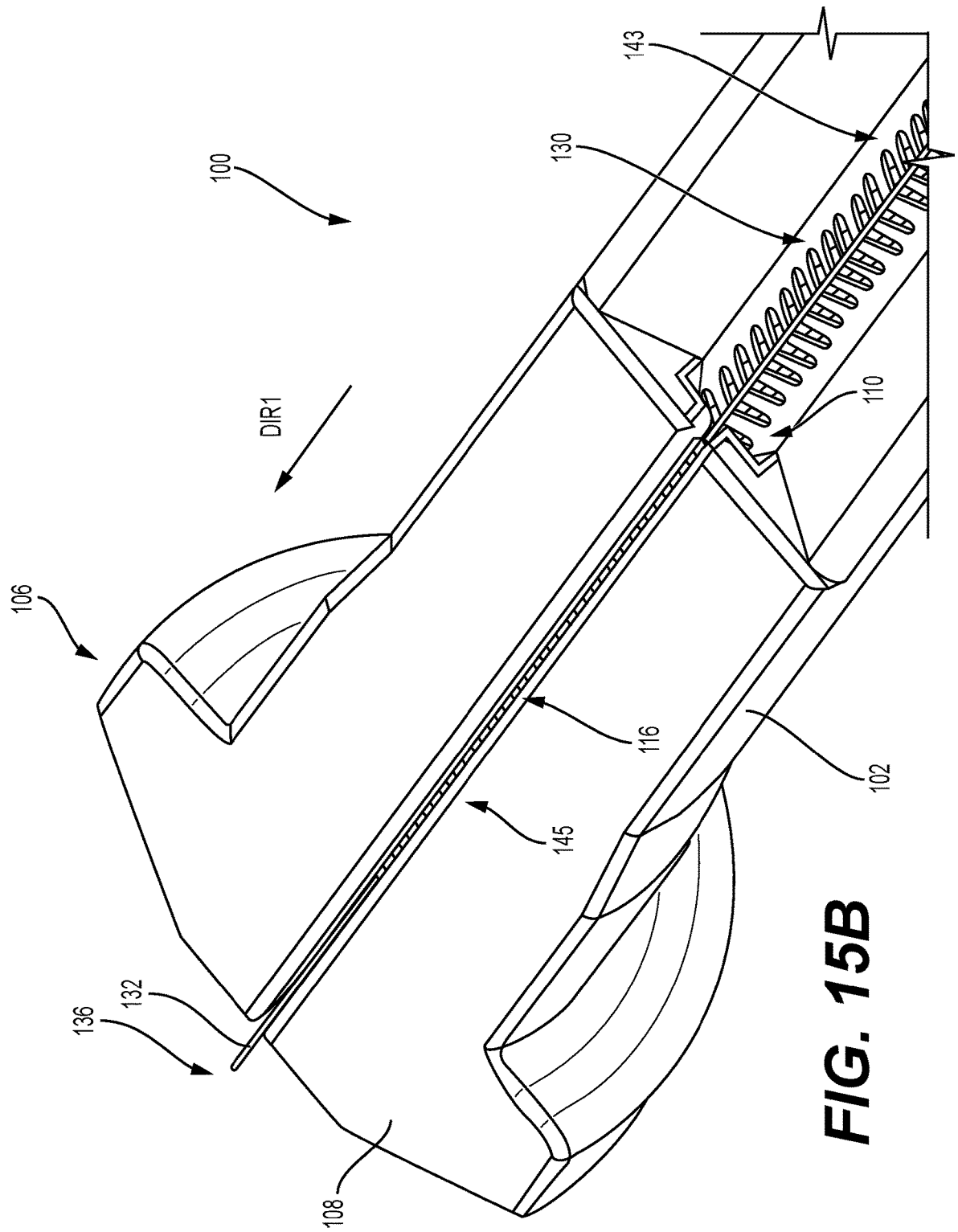
FIG. 15B is a perspective, magnified top side view of a distal end of the cartridge and the barbed suture shown in FIG. 15A.

Referring to FIGS. 15A and 15B, in one embodiment, when loading the barbed suture into the cartridge 100, the end effector 140 at the proximal end 134 of the barbed suture 130 is preferably inserted into the end effector opening 120, which is located at the proximal end 104 of the elongated body 102 of the cartridge. In one embodiment, the end effector 140 is preferably disposed within the second channel 112 that extends to the distal end 106 of the elongated body 102.

In one embodiment, after the end effector has been inserted into the second channel, the proximal barbed section 143 of the barbed suture 130 preferably overlies both the elongated slot 118 (FIG. 2A) and the second channel 112 of the cartridge 100. In one embodiment, the laterally extending slot 116 located adjacent the distal end 106 of the elongated body 102 enables the distal end of the barbed suture 130 to be inserted into the first channel 110 and pulled in the distal direction DIR1 for positioning the distal end 136 of the elongated core 132 distal to the larger diameter head 108 of the elongated 102.

Figure 16A:
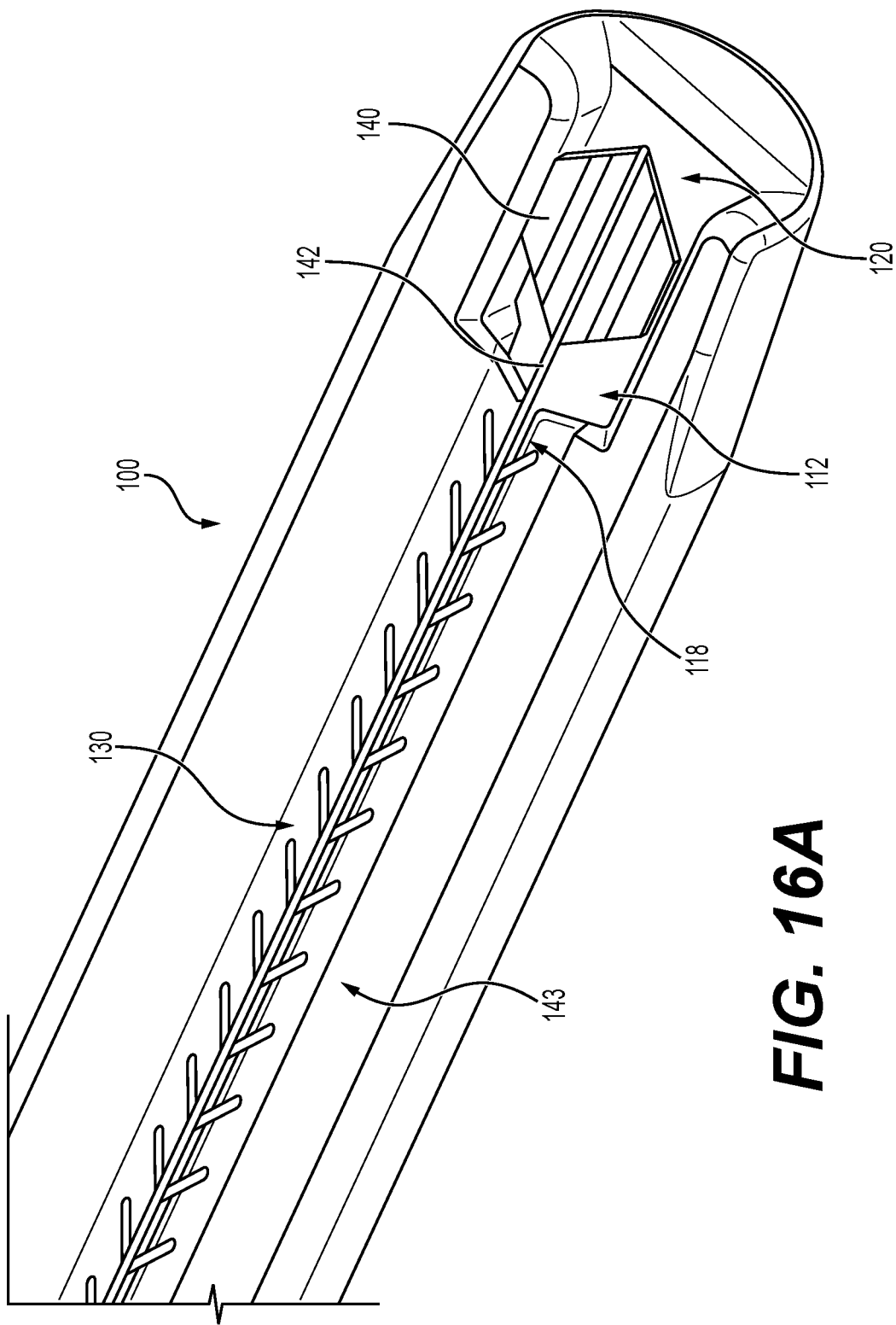
FIG. 16A is a perspective, magnified view of the proximal end of the cartridge and the barbed suture shown in FIG. 15.
Figure 16B:
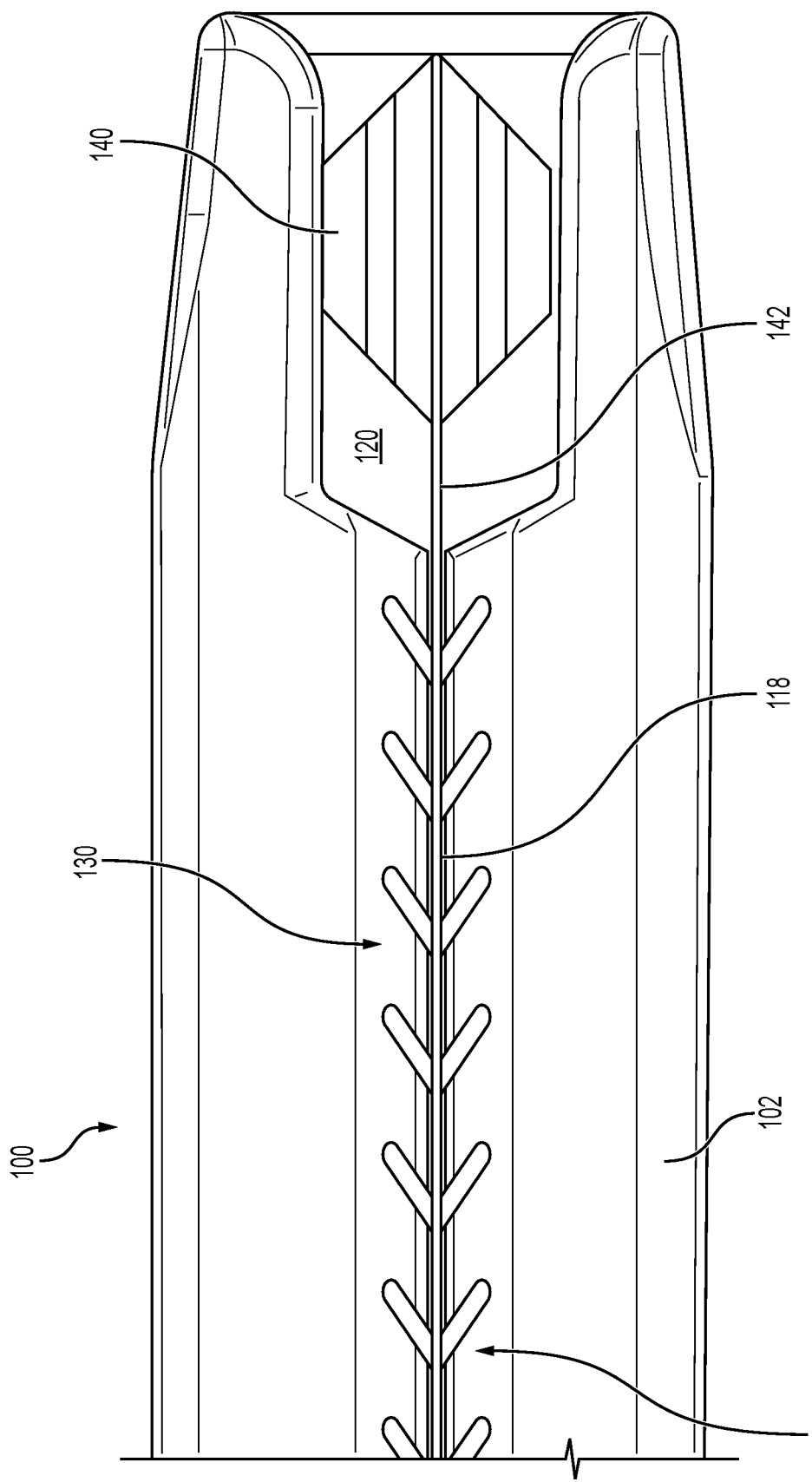
FIG. 16B is a top plan view of the proximal end of the cartridge and the barbed suture shown in FIG. 16A.

Referring to FIGS. 16A and 16B, in one embodiment, after the end effector 140 has been inserted into the second channel 112, the interconnecting segment 142 of the barbed suture 130 that is distal to the end effector 140 preferably passes through the elongated slot 118 for enabling the end effector 140 to be pulled through the second channel 112 while the proximal and distal barbs sections 143, 145 of the barbed suture are pulled through the first channel 110 (FIG. 15B).

Figure 17:
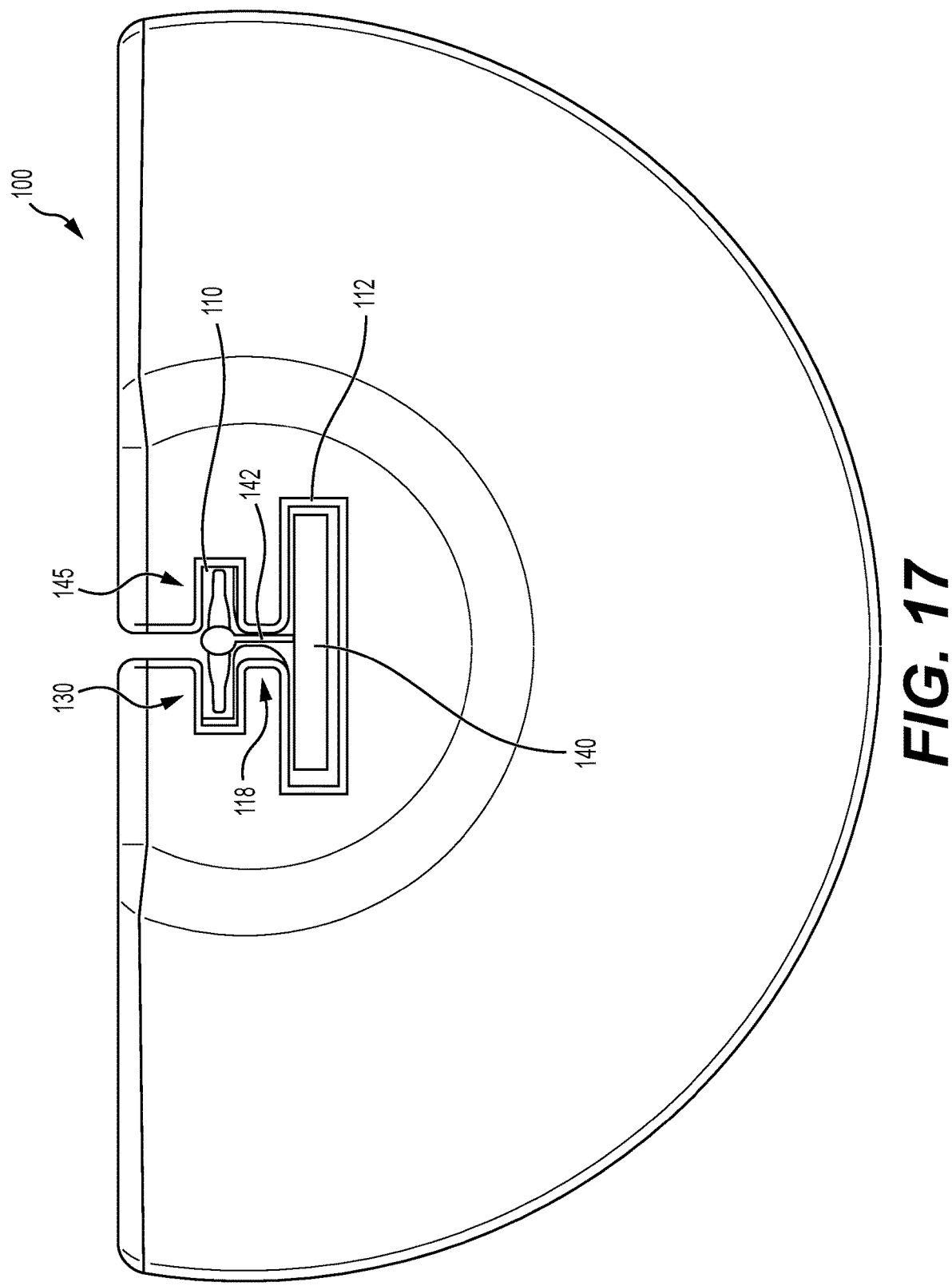
FIG. 17 is a distal end view of the cartridge and the barbed suture shown in FIGS. 13A-13C and 14A-140.

Referring to FIG. 17, in one embodiment, after the barbed suture 130 is loaded into the cartridge 100, the distal barbed section 145 of the barbed suture is preferably positioned within the first channel 110 of the cartridge 100, and the end effector 140 of the barbed suture 130 is preferably positioned within the second channel 112 of the cartridge 100. The interconnecting segment 142 (FIGS. 16A and 16B) of the barbed suture preferably passes through the elongated slot 118 of the cartridge 100 for enabling the barbed suture 132 to be pulled toward the distal end of the cartridge with the end effector 140 disposed within the second channel 112 and the distal barbed section 145 of the barbed suture 130 disposed within the first channel 110.

In one embodiment, the cross-sectional dimension of the width of the first channel is smaller than the width of the second channel. The two separate pathways (i.e., the first and second channels) are needed to limit the movement of the overall core structure in order to prevent the end effector from kicking out of the axis of the barbed suture 130 as it is over-braided. In one embodiment, as the barbed suture is pulled from the distal end of the cartridge 100 by a braider, the outer dimension of the distal barbed section 145 and the proximal barbed section 143 (FIG. 16B) have frictional engagement with the first channel to generate a drag on the barbed sections of the barbed suture. In addition, as the end effector 140 is pulled distally through the second channel 112, the outer dimension of the end effector has frictional engagement with the second channel to generate a drag on the end effector of the barbed suture. The frictional engagements are preferably sufficient to maintain alignment of the barbed suture in a single plane, but are desirably less than the "take-up" force of the braider.

Figure 18A:
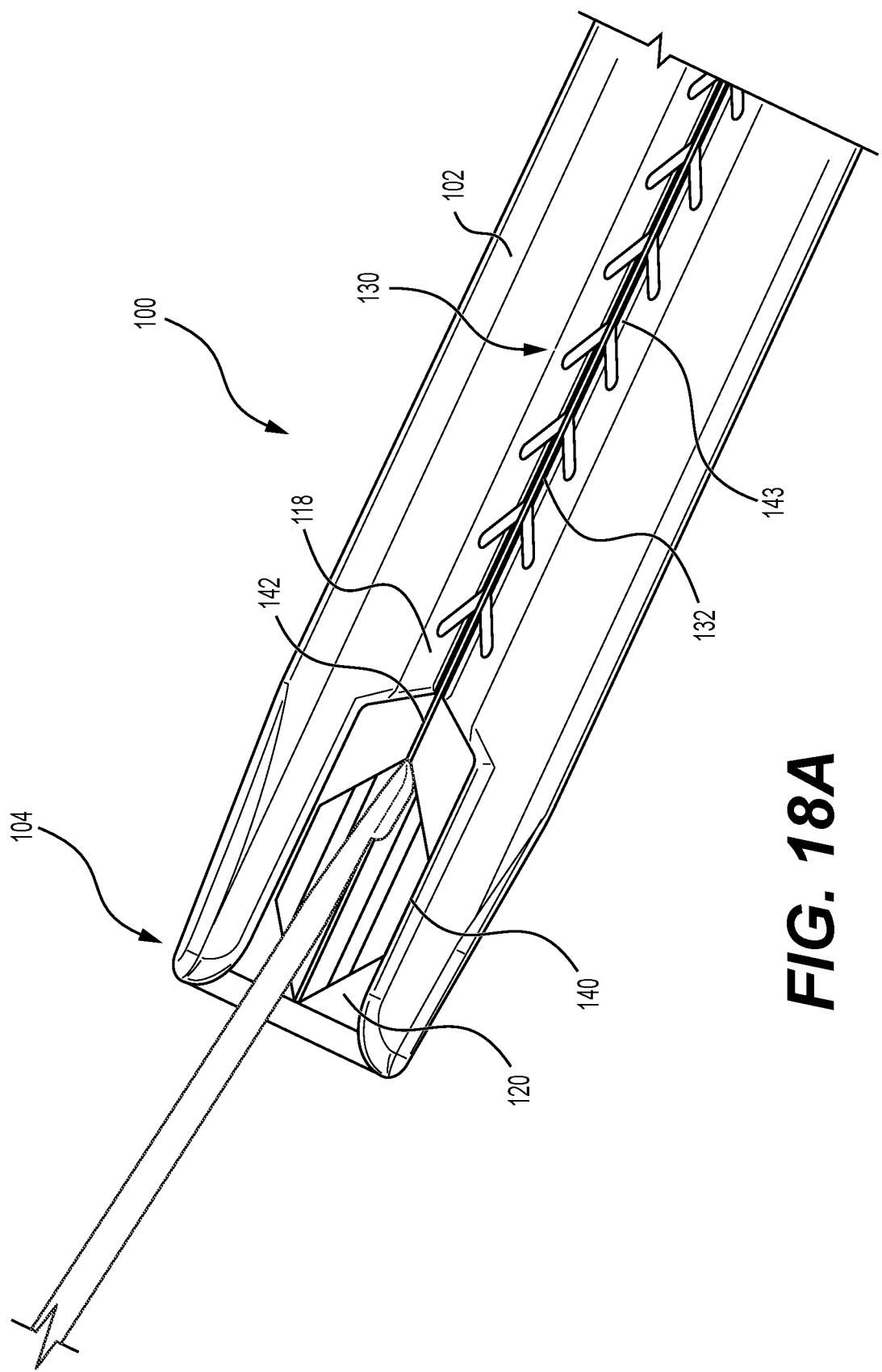
FIG. 18A illustrates a first step of a method of loading a barbed suture into a cartridge, in accordance with one embodiment of the present patent application.

Referring to FIG. 18A, in one embodiment, in one method of loading a suture into a cartridge for conducting a braiding procedure, the end effector 140 of the barbed suture 130 may be inserted into the end effector opening 120 located at the proximal end 104 of the elongated body 102 of the cartridge 100. The interconnecting segment 142 of the elongated core 132 of the barbed suture 130, which is distal to the end effector 140, preferably passes through the elongated slot 118 of the cartridge 100 so that the end effector 140 may be positioned within the second channel while the proximal barbed section 143 of the barbed suture 130 may be positioned above both the elongated slot 118 and the second channel 112 (FIG. 5B).

Figure 18B:
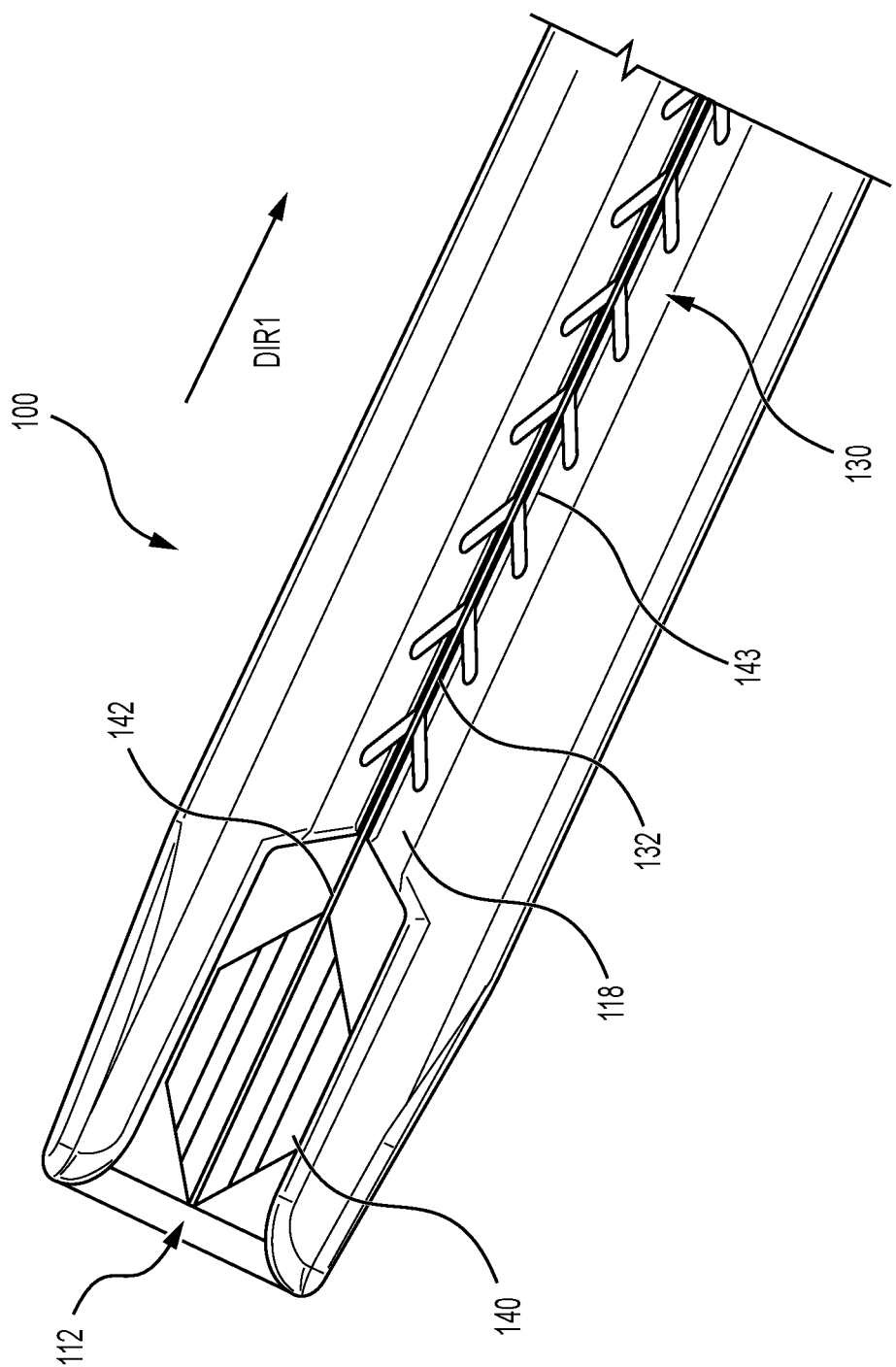
FIG. 18B illustrates a second stage of a method of loading a barbed suture into a cartridge, in accordance with one embodiment of the present patent application.

Referring to FIG. 18B, in one embodiment, after the end effector 140 has been positioned within the second channel 112 of the cartridge 100, the interconnecting segment 142 of the elongated core 132 preferably passes through the elongated slot 118. The proximal barbed section 143 of the barbed suture 130, which is distal to the interconnecting segment 142, preferably overlies the elongated slot 118. The distal end of the barbed suture 130 may be pulled in the distal direction designated DIR1, which, in turn, pulls the end effector 140 through the second channel 112 in the distal direction DIR1.

Figure 18C:
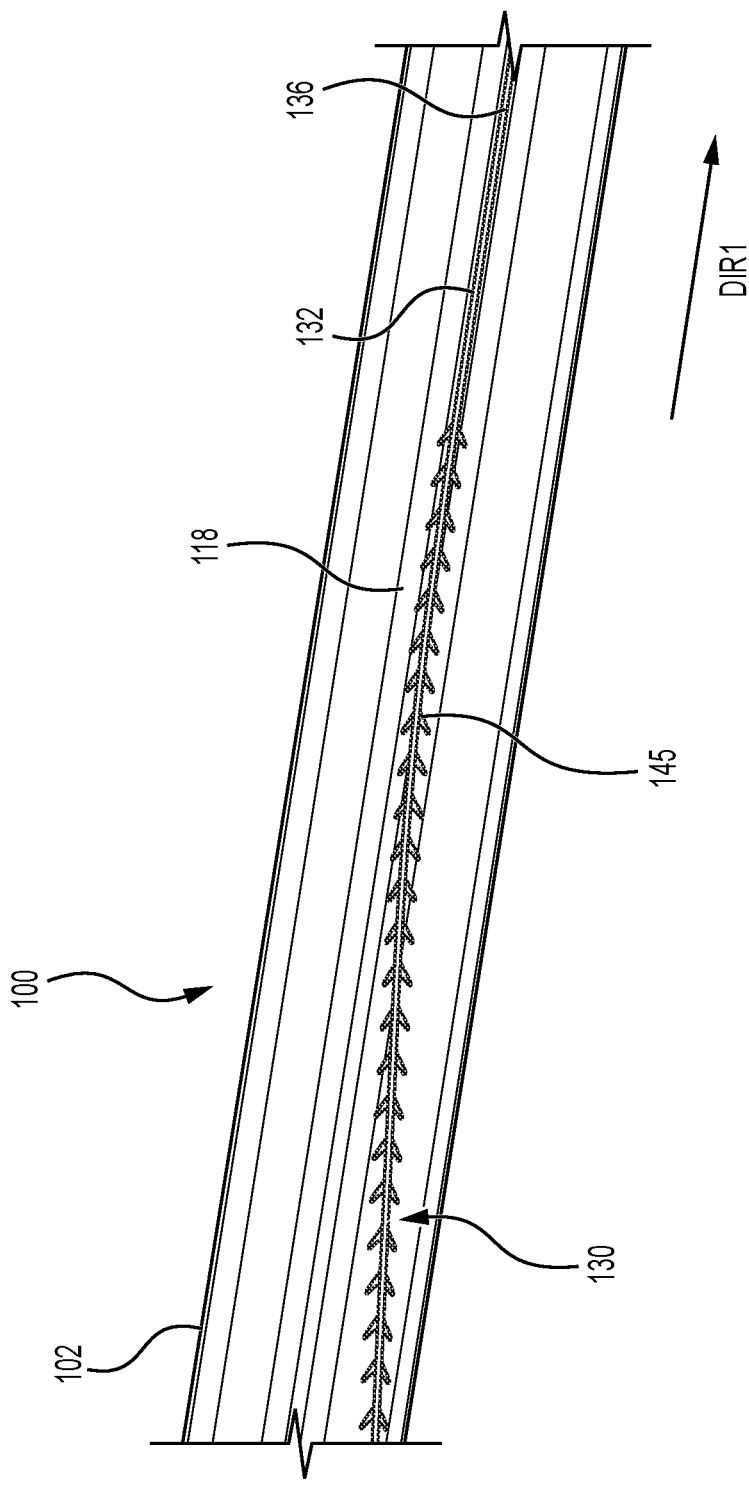
FIG. 18C illustrates a third stage of a method of loading a barbed suture into a cartridge, in accordance with one embodiment of the present patent application.

Referring to FIG. 18C, in one embodiment, the distal end 136 of the elongated core 132 of the barbed suture 130 is preferably passed through the laterally extending slot 116 (FIG. 5A) located adjacent the distal end of the elongated body 102 of the cartridge 100 for positioning the distal barbed section 145 of the barbed suture 130 within the first channel 110 (FIG. 5A) of the cartridge 100. The distal end 136 of the elongated core 132 is preferably pulled in the distal direction DIR1 for loading the barbed suture 130 into the cartridge 100.

Figure 18D:
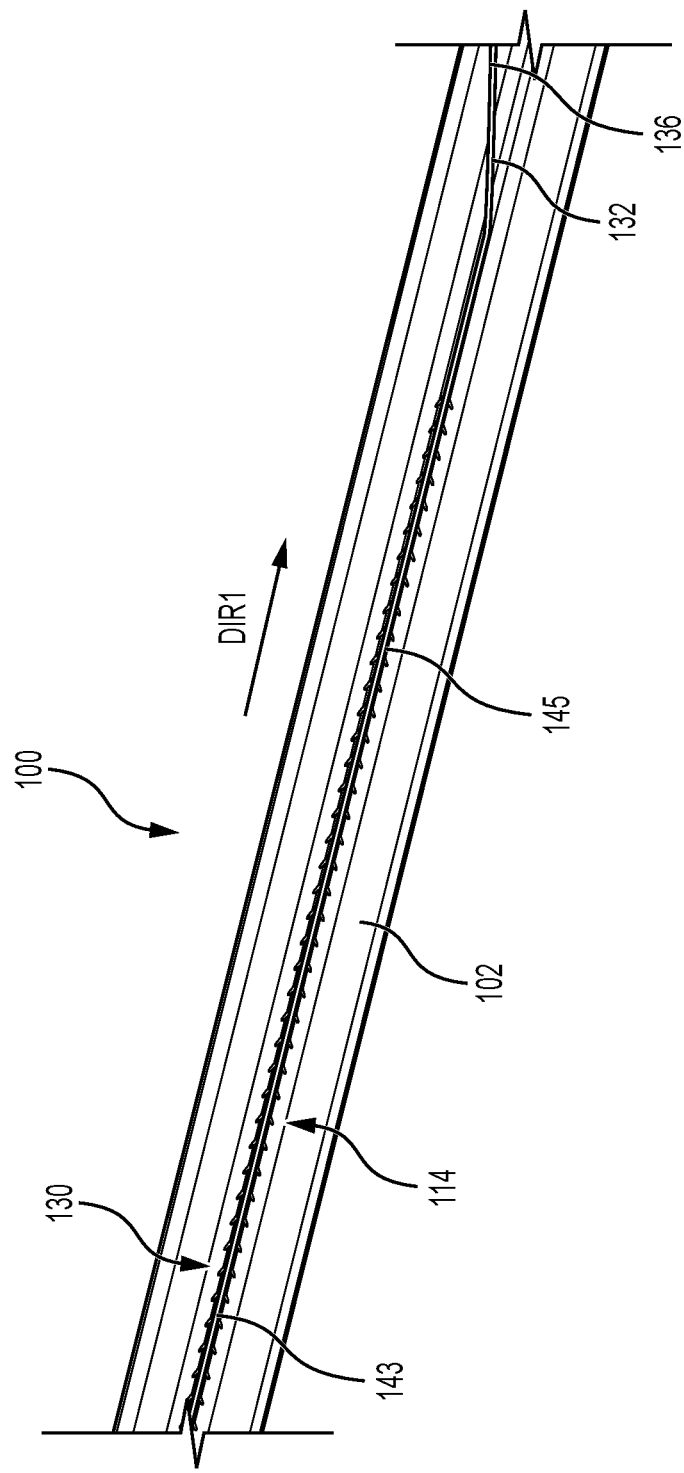
FIG. 18D illustrates a fourth stage of a method of loading a barbed suture into a cartridge, in accordance with one embodiment of the present patent application.

Referring to FIG. 18D, in one embodiment, the distal end 136 of the elongated core 132 of the barbed suture 130 is preferably pulled in the distal direction DIR1 until the distal end 136 of the elongated core 132 is distal to the head 108 of the elongated body 102 of the cartridge 100, whereupon the distal end 136 may be engaged by a braider. The barbed distal section 145 of the barbed suture 130 is preferably positioned within the first channel 110 (FIG. 5A) of the elongated body 102 of the cartridge 100 while the proximal barbed section 143 of the barbed suture 130 overlies the elongated slot 118 and the second channel 112 (FIG. 5A) of the elongated body.

Figure 18E:
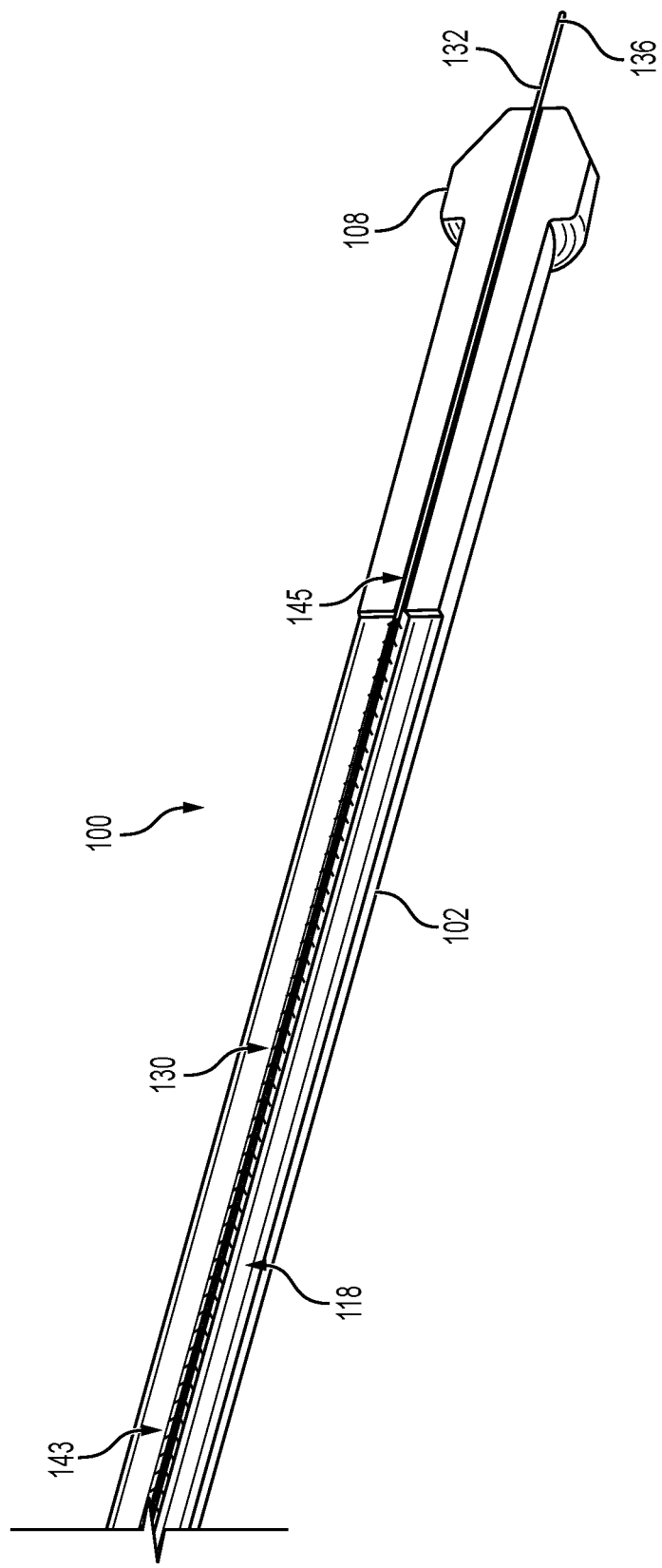
FIG. 18E illustrates a fifth stage of a method of loading a barbed suture into a cartridge, in accordance with one embodiment of the present patent application.

Referring to FIG. 18E, in one embodiment, after the barbed suture 130 has been loaded into the cartridge 100, the distal end 136 of the elongated core 132 preferably extends distally beyond the head 108 located at the distal end of the elongated body 102 of the cartridge 100. The distal barbed section 145 of the barbed suture 130 preferably passes through the first channel 110 (FIG. 5A) of the cartridge 100 while the proximal barbed section 143 of the barbed suture 130 overlies the elongated slot 118 and the second channel 112 (FIG. 5A) that extends beneath the elongated slot 118.

Figure 19A:
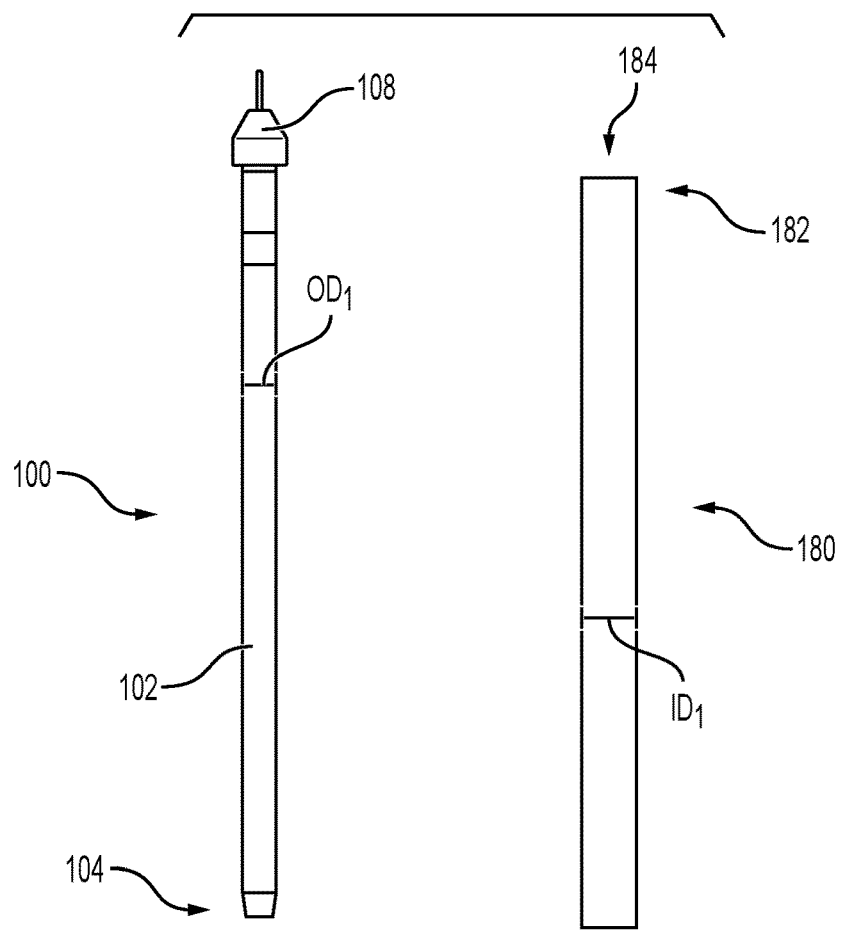
FIG. 19A shows a side elevation view of a cartridge and a cartridge guide tube, in accordance with one embodiment of the present patent application.
Figure 19B:
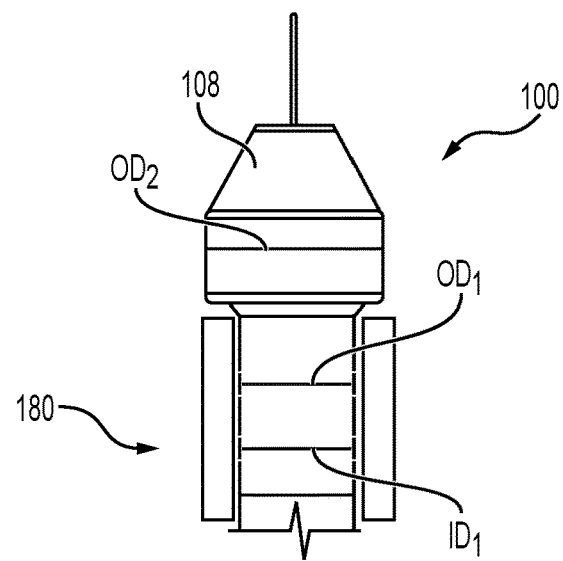
FIG. 19B shows a cross-sectional view of the cartridge guide tube of FIG. 19A after the cartridge has been inserted into the cartridge guide tube.

Referring to FIGS. 19A and 19B, in one embodiment, the proximal end 104 of the elongated body 102 of the cartridge 100 may be inserted into a cartridge guide tube 180 having a distal end 182 with an opening 184 that is adapted to receive the elongated body 102 of the cartridge 100. The elongated body 102 of the cartridge 100 has an outer diameter $OD_1$ that preferably matches or is slightly smaller than the inner diameter $ID_1$ of the cartridge guide tube 180. The larger diameter head 108 of the cartridge 100 has an outer diameter $OD_2$ that is greater than the inner diameter $ID_1$ of the opening 184 at the distal end 182 of the cartridge guide tube 180, which prevents the cartridge 100 from entering the distal end 182 of the cartridge guide tube 180. The increased diameter of the head 108 insures that the head 108 of the cartridge 100 does not slip into and/or fall inside the cartridge guide tube 180.

Figure 20:
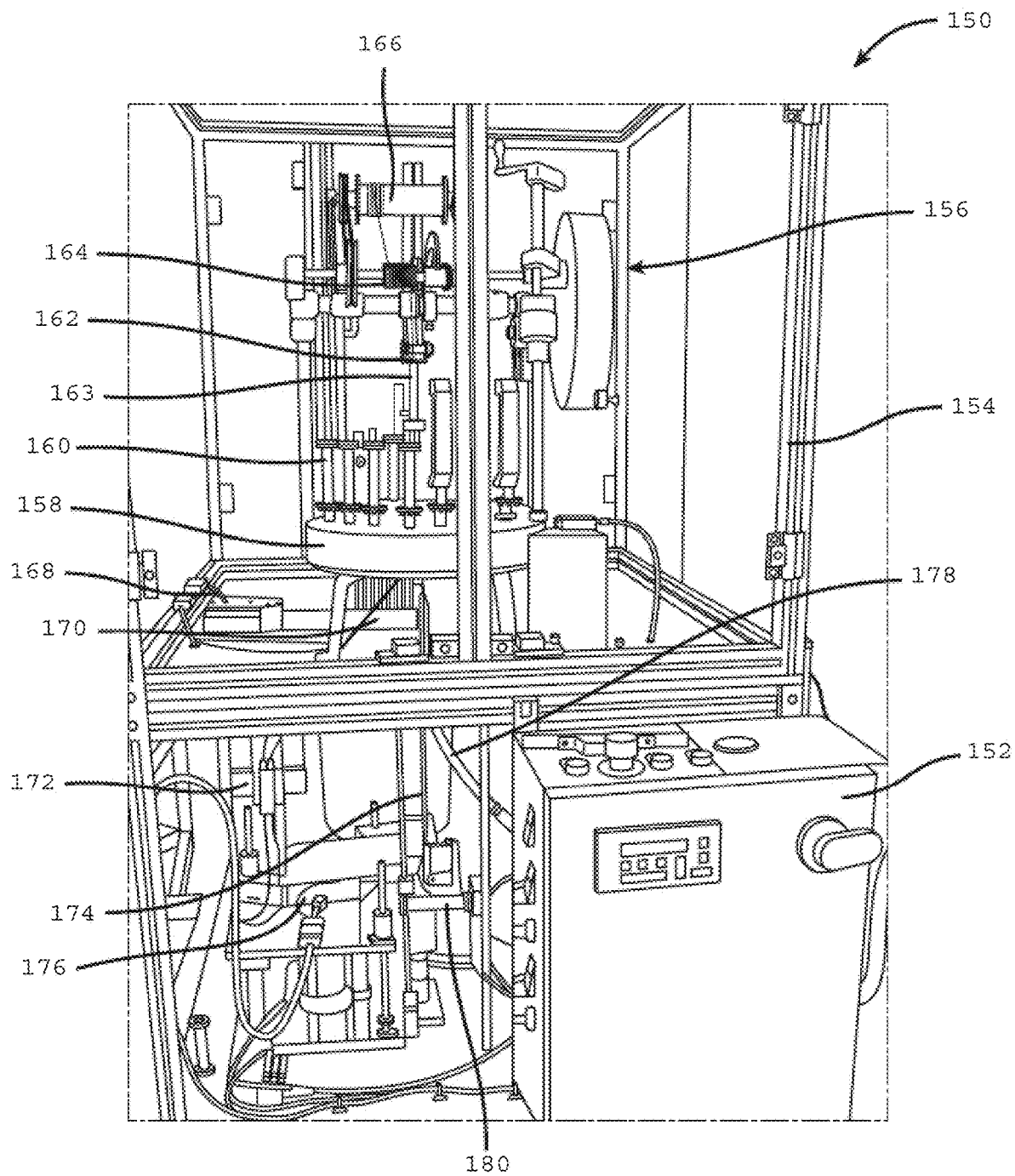
FIG. 20 is a perspective view of an automated braiding system used for braiding barbed sutures, in accordance with one embodiment of the present patent application.

Referring to FIG. 20, in one embodiment, the cartridge and the barbed suture loaded into the cartridge may be inserted into an automated braiding system 150 for making braided barbed sutures, such as that disclosed in U.S. Pat. Nos. 8,210,085, 8,733,223, and 9,206,535, assigned to Ethicon, Inc., the disclosures of which are hereby incorporated by reference herein. In one embodiment, the automated braiding system 150 preferably includes a system controller 152 for controlling operation of the system. The automated system 150 preferably includes an enclosed area 154 that houses a braider assembly 156 adapted for braiding filaments around barbed sutures to form braided barbed sutures. The braider assembly 156 preferably includes a braider plate 158 and bobbins 160 that contain multi-filaments that are positioned around the braider plate 158. The braider assembly 156 desirably includes a braider eyelet 162 for directing the filaments toward a central braiding zone, a cartridge guide tube 163, a braider dowel 164 and a suture collection spool 166. The braider system also preferably includes an air cylinder 168 located beneath the braider plate 158 and a magazine 170 for holding a plurality of cartridges 100 that are pre-loaded with barbed sutures to be braided. In one embodiment, the air cylinder preferably serves as an actuator to move the cartridges.

In one embodiment, the automated braiding system 150 also preferably includes a fiber optic sensor display 172 and a cartridge insertion rod 174 for advancing loaded cartridges, one at a time, into the enclosed area 154. The automated braiding system 150 also desirably includes a lifting rack 176 that is moveable in a first direction (e.g., up) for advancing a loaded cartridge toward the braider eyelet 162, and in a second direction (e.g., down) for dispensing an empty cartridge from the automated system. The air cylinder may be coupled with the lifting rack.

In one embodiment, the automated braiding system 150 also desirably includes a cartridge ejection tube 178 for dispensing empty cartridges from the system after the barbed sutures 130 have been withdrawn from the cartridges by the braider system, and preferably after the cartridges have been returned to a position below the braider plate 158 by the lifting rack 176.

Figure 21:
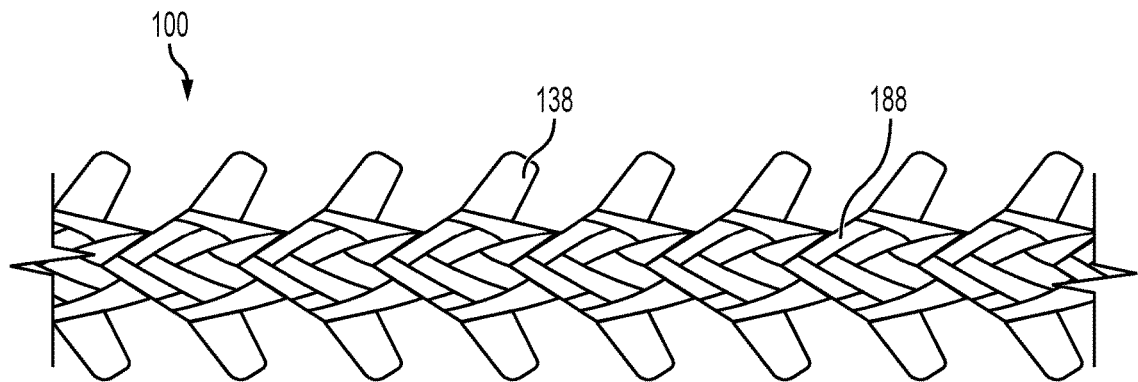
FIG. 21 shows a top plan view of a section of a braided barbed suture, in accordance with one embodiment of the present patent application.

Referring to FIG. 21, in one embodiment, filaments 188 are braided about the elongated core 132 (FIG. 10A) of the barbed suture 100 to form a braided barbed suture. In the braided barbed suture of FIG. 21, a plurality of filaments are braided about the suture along the length thereof. The barbs 138 preferably project through the plurality of filaments so that the barbs remain exposed. The barbs 138 preferably lie in a single plane, which preferably results from the barbed insert being held in a single plane by the cartridge as the barbed insert is withdrawn from the cartridge.

Figure 22A:
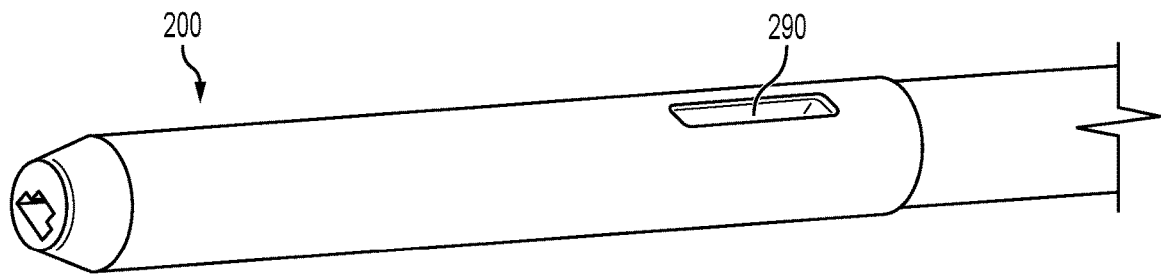
FIG. 22A is a perspective view of a cartridge for a barbed suture, in accordance with one embodiment of the present patent application.
Figure 22B:
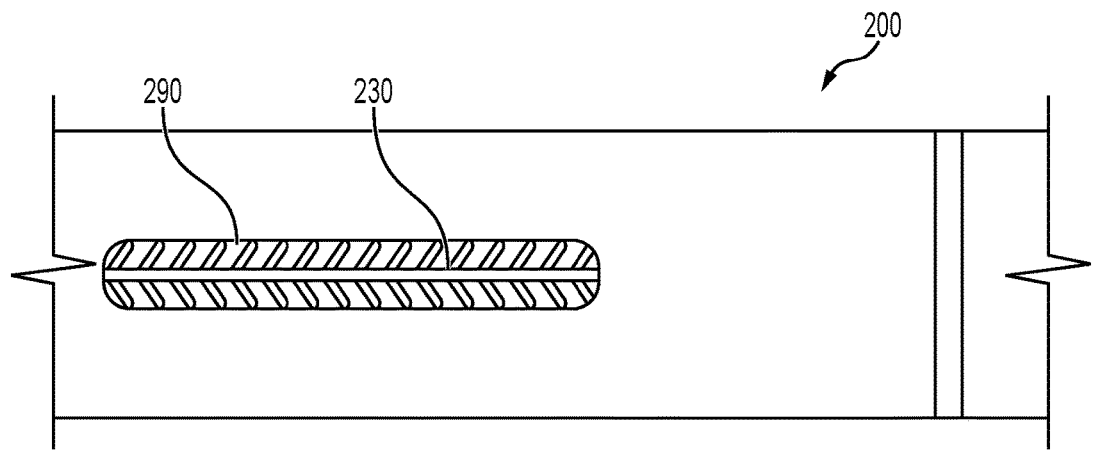
FIG. 22B shows a mid-section of the cartridge of FIG. 22A with a barbed suture visible through an optical window, in accordance with one embodiment of the present patent application.

Referring to FIGS. 22A and 22B, in one embodiment, a cartridge 200 for a barbed suture preferably includes an optical window 290 that provides a view of the barbed suture 230 when the barbed suture is disposed in the cartridge. The optical window 290 may be located in an intermediate section of the cartridge 200. In one embodiment, the automated braiding system 150 (FIG. 20) preferably includes an optical sensor adapted to determine when the barbed suture 230 has been completely dispensed from the cartridge 200. In one embodiment, once the barbed suture has been completely dispensed, the optical sensor will send at least one signal to a system controller indicating that the barbed insert has been dispensed. In response, the system controller will preferably issue commands for retracting the empty cartridge 200 below the braider plate and discharging the empty cartridge from the system so that another cartridge loaded with a barbed suture may be advanced into place for braiding.

In one embodiment of the present invention, barbed sutures are loaded into the cartridges and the loaded cartridges are advanced into the enclosed area 154 of the automated braider system. Once the barbed inserts are advanced into the enclosed area, filaments are preferably braided around the barbed inserts to make braided barbed sutures. The barbed inserts and filaments may be made of biocompatible absorbable materials, non-absorbable materials, and combinations of absorbable and non-absorbable materials. Preferred non-absorbable materials suitable for both the barbed inserts and the filaments are polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons, etc. and the like, or copolymers of combinations thereof. Preferred absorbable polymeric materials suitable for both the barbed inserts and the filaments include polydioxanone, polyglycolic acid, copolymers of glycolide and lactide, polyoxaesters, and poliglecaprone. In certain preferred embodiments, these may include combinations of both absorbable and non-absorbable materials, especially for the filaments. In addition, metals or ceramics may be suitable for certain applications, such as instances where specific strength or corrosion resistance is necessary. In one preferred embodiment, the preferred material is a polymer blend of polyvinylidene fluoride and polyvinylidene fluoride-co-hexafluoropropylene material. In a highly preferred embodiment, the filament material is polyethylene terephthalate. In addition, any of these materials may have conventional surface modifications that include coatings, plasma treatments, therapeutics such as antimicrobial and/or antibacterial materials (e.g., Triclosan) and the like.

In one embodiment, cartridges for feeding barded sutures into braiding systems may have a wide variety of shapes and configurations. For example, referring to FIGS. 23A-23D, in one embodiment, a cartridge 300 that is adapted to advance a suture into a braiding assembly for suture braiding preferably includes an elongated body 302 having a proximal end 304 and a distal end 306 with a chamfered leading end 308. The cartridge preferably has one or more of the structural features of the cartridge embodiments shown and described above in FIGS. 1A-9B.

In one embodiment, the cartridge 300 preferably includes a first channel 310 that extends to the distal end 306 of the elongated body 302, and a second channel 312 that also extends to the distal end 306 of the elongated body 302. The first and second channels 310, 312 preferably define separate and distinct pathways through the cartridge 300. In one embodiment, the first and second channels 310, 312 desirably extend along respective axes that are parallel with one another. In one embodiment, the first and second channels have different cross-sectional areas and/or dimensions. In one embodiment, the first channel 310 may be wider than high, and the second channel 312 may also be wider than high.

In one embodiment, the cartridge 300 preferably includes a major surface 314 that extends to the distal end 306 of the elongated body 302. In one embodiment, the cartridge 300 preferably includes a laterally extending slot 316 that extends from the major surface 314 to a first end (e.g., an upper end) of the first channel 310 for providing access to the first channel 310. In one embodiment, the laterally extending slot 316 has a length that matches the length of the first channel 310. In one embodiment, prior to commencement of a braiding procedure, when a suture is being loaded into the cartridge 300, a distal section of the suture may be passed through the laterally extending slot 316 for positioning the distal section of the suture within the first channel 310.

In one embodiment, the cartridge 300 preferably includes an elongated slot 318 that substantially matches the length of the second channel 312. In one embodiment, the elongated slot 318 extends to the distal end 306 of the elongated body 302 for interconnecting the first and second channels 310, 312 adjacent the distal end 306 of the elongated body 302.

In one embodiment, the proximal end 304 of the elongated body 302 desirably includes an end effector opening 320 that is preferably adjacent the proximal end of the second channel 312 and that is adapted to receive an end effector located at a proximal end of a suture (e.g., a barbed suture). In one embodiment, the end effector of the suture is adapted to be pulled distally (i.e., in the distal direction DIR1) through the second channel 312 (FIG. 23D) while a barbed distal section of the suture is pulled through the first channel 310 (FIG. 23D) of the cartridge 300. In one embodiment, an interconnecting segment of the suture that is distal to the end effector preferably interconnects the end effector with the proximal end of the suture core. In one embodiment, the interconnecting segment preferably passes through the elongated slot 318 of the cartridge 300 as the suture is pulled distally in the direction DIR1 through the first and second channels 310, 312 (FIGS. 23A and 23B) of the cartridge 300.

Figure 23A:
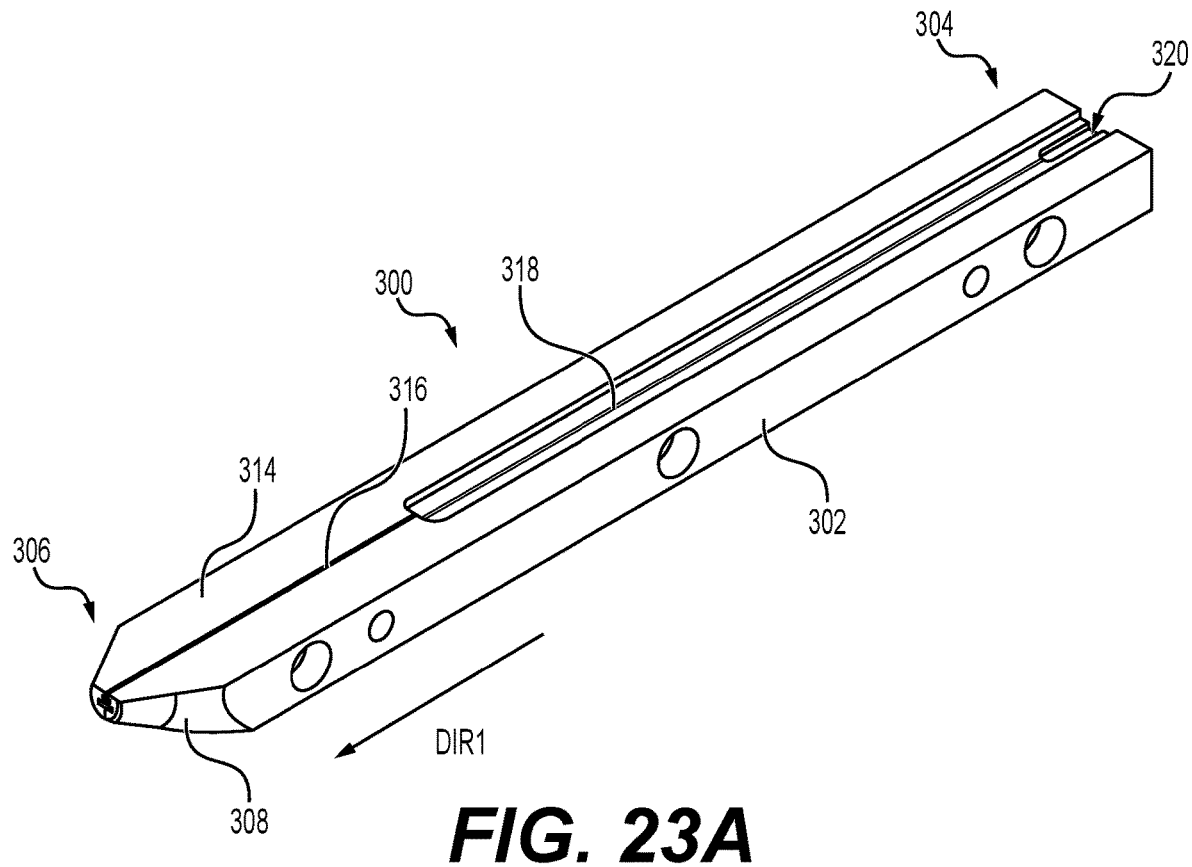
FIG. 23A is a perspective view of a cartridge for a barbed suture, the cartridge including an elongated body having a chamfered distal end, in accordance with one embodiment of the present patent application.
Figure 23B:
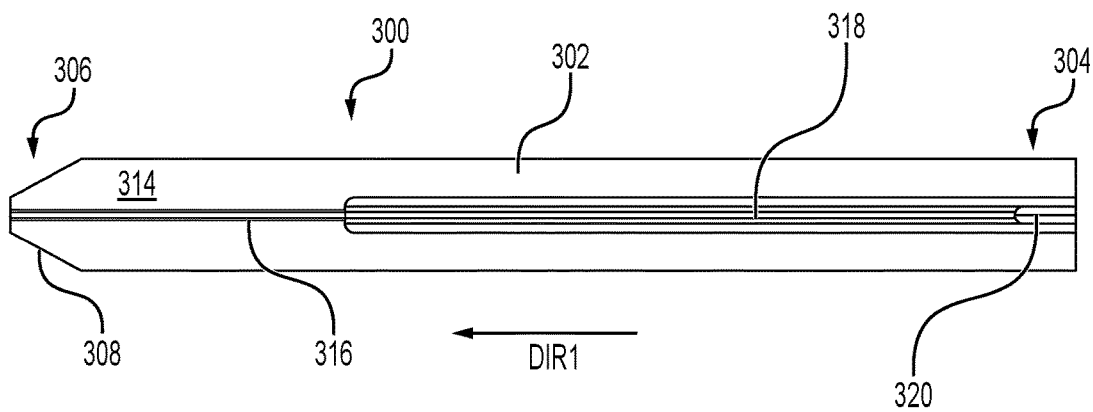
FIG. 23B is a top plan view of the cartridge shown in FIG. 23A.
Figure 23C:
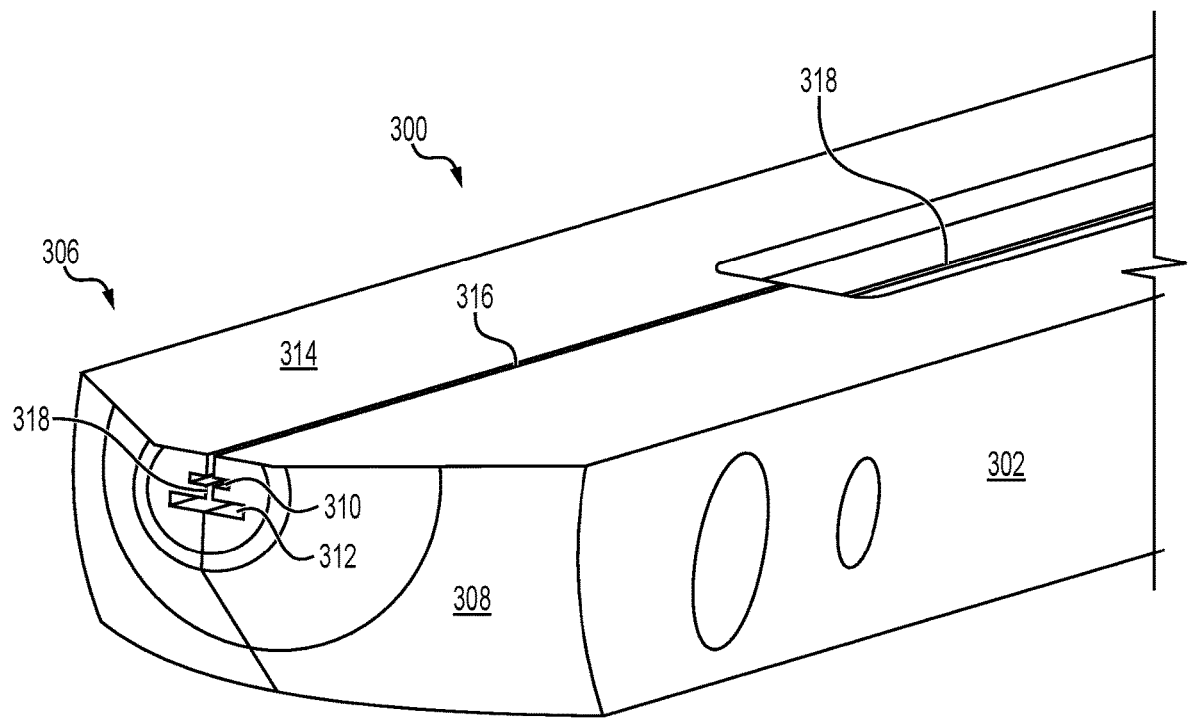
FIG. 23C is a magnified view of the distal end of the cartridge shown in FIGS. 23A and 23B.
Figure 23D:
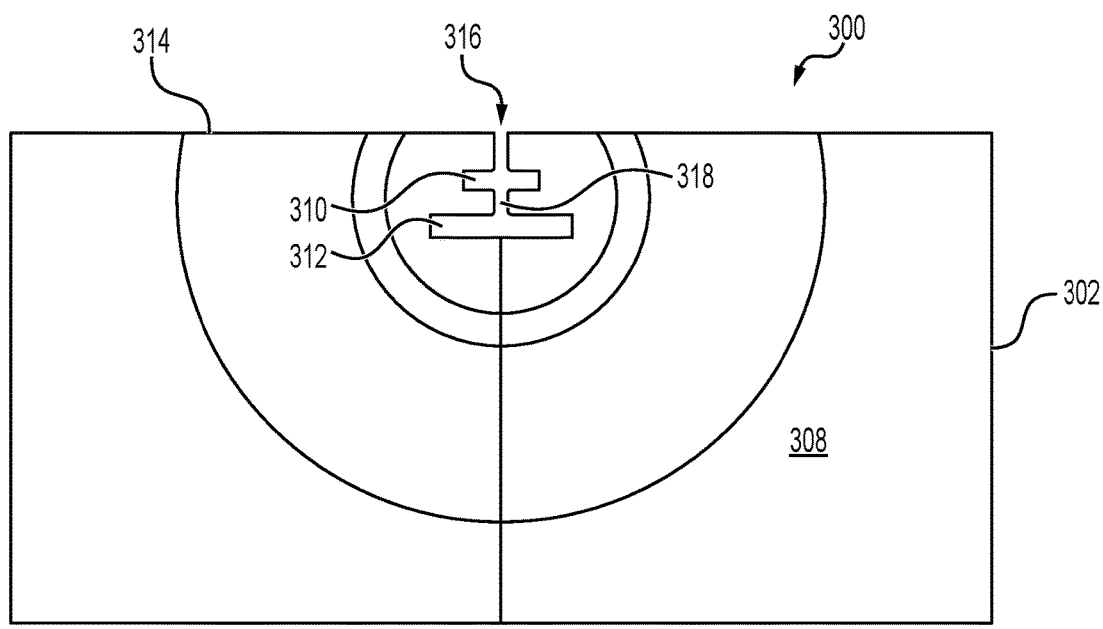
FIG. 23D is a distal end view of the cartridge shown in FIGS. 23A-23C.

Referring to FIGS. 23C and 23D, in one embodiment, the cartridge 300 preferably includes the first channel 310 that extends to the distal end 306 of the elongated body 302, and the second channel 312 that also extends to the distal end 306 of the elongated body 302. In one embodiment, the first and second channels 310, 312 preferably extend along respective axes that are parallel to one another. In one embodiment, the first and second channels 310, 312 define separate and distinct paths through the elongated body of the cartridge 300.

In one embodiment, the elongated body 302 preferably includes the major surface 314 that extends laterally across the width of the elongated body and that extends to the distal end of the elongated body. In one embodiment, the laterally extending slot 316 desirably extends from the major surface 314 to the first channel 310 of the cartridge 300 for enabling the distal end of a suture to be inserted into the first channel 310 prior to placing the cartridge 300 into a braiding machine. In one embodiment, where the first and second channels 310, 312 overlap one another along the length of the first channel 310, the elongated slot 318 preferably extends from the first channel 310 and the second channel 312, which enables the interconnecting segment of the suture to pass through the elongated slot to the distal end of the elongated body of the cartridge.

In one embodiment, the first and second channels 310, 312 preferably have respective cross-sectional areas that are different. In one embodiment, as a braider pulls a distal end of a barbed suture in a distal direction through the first channel 310, the outer dimensions of the barbs of the barbed suture preferably create a slight frictional engagement with the inner surfaces of the first channel for generating a slight drag on the barbed suture. In one embodiment, as an end effector at a proximal end of the barbed suture is pulled in the distal direction through the second channel 312, the outer dimensions of the end effector preferably create a slight frictional engagement with the inner surfaces of the second channel for generating a slight drag on the end effector.

Referring to FIGS. 24A-24D, in one embodiment, a cartridge 400 that is adapted to hold a suture for a suture braiding procedure preferably includes an elongated body 402 having a proximal end 404 and a distal end 406 having a rectangular shaped leading end 408. The cartridge preferably has one or more of the structural features of the cartridge embodiments shown and described above in FIGS. 1A-9B.

In one embodiment, the cartridge 400 preferably includes a first channel 410 that extends to the distal end 406 of the elongated body 402, and a second channel 412 that also extends to the distal end 406 of the elongated body 402. The first and second channels 410, 412 preferably define separate and distinct pathways through the cartridge 400. In one embodiment, the first and second channels 410, 412 desirably extend along respective axes that are parallel with one another. In one embodiment, the first and second channels have different cross-sectional areas. In one embodiment, the first channel 410 may be wider than high, and the second channel 412 may also be wider than high.

In one embodiment, the cartridge 400 preferably includes a major surface 414 that extends to the distal end 406 of the elongated body 402. In one embodiment, the cartridge 400 preferably includes a laterally extending slot 416 that extends from the major surface 414 to a first end (e.g., an upper end) of the first channel 410 for providing access to the first channel 410. In one embodiment, the laterally extending slot 416 has a length that matches the length of the first channel 410. In one embodiment, prior to commencement of a braiding procedure, when a suture is being loaded into the cartridge 400, a distal section of the suture may be passed through the laterally extending slot 416 for positioning the distal section of the suture within the first channel 410.

In one embodiment, the cartridge 400 preferably includes an elongated slot 418 that matches the length of the second channel 412. In one embodiment, the elongated slot 418 extends to the distal end 406 of the elongated body 402 for interconnecting the first and second channels 410, 412 adjacent the distal end 406 of the elongated body 402.

In one embodiment, the proximal end 404 of the elongated body 402 desirably includes an end effector opening 420 that is preferably adjacent the proximal end of the second channel 412 and that is adapted to receive an end effector located at a proximal end of a suture (e.g., a barbed suture). In one embodiment, the end effector of the suture is adapted to be pulled distally (i.e., in the distal direction DIR1) through the second channel 412 (FIG. 24D) while a barbed distal section of the suture is pulled through the first channel 410 (FIG. 24D) of the cartridge 400. In one embodiment, an interconnecting segment of the suture that is distal to the end effector preferably interconnects the end effector with the proximal end of the suture core. In one embodiment, the interconnecting segment preferably passes through the elongated slot 418 of the cartridge 400 as the suture is pulled distally in the direction DIR1 through the first and second channels 410, 412 (FIGS. 24A and 24B) of the cartridge 400.

Figure 24A:
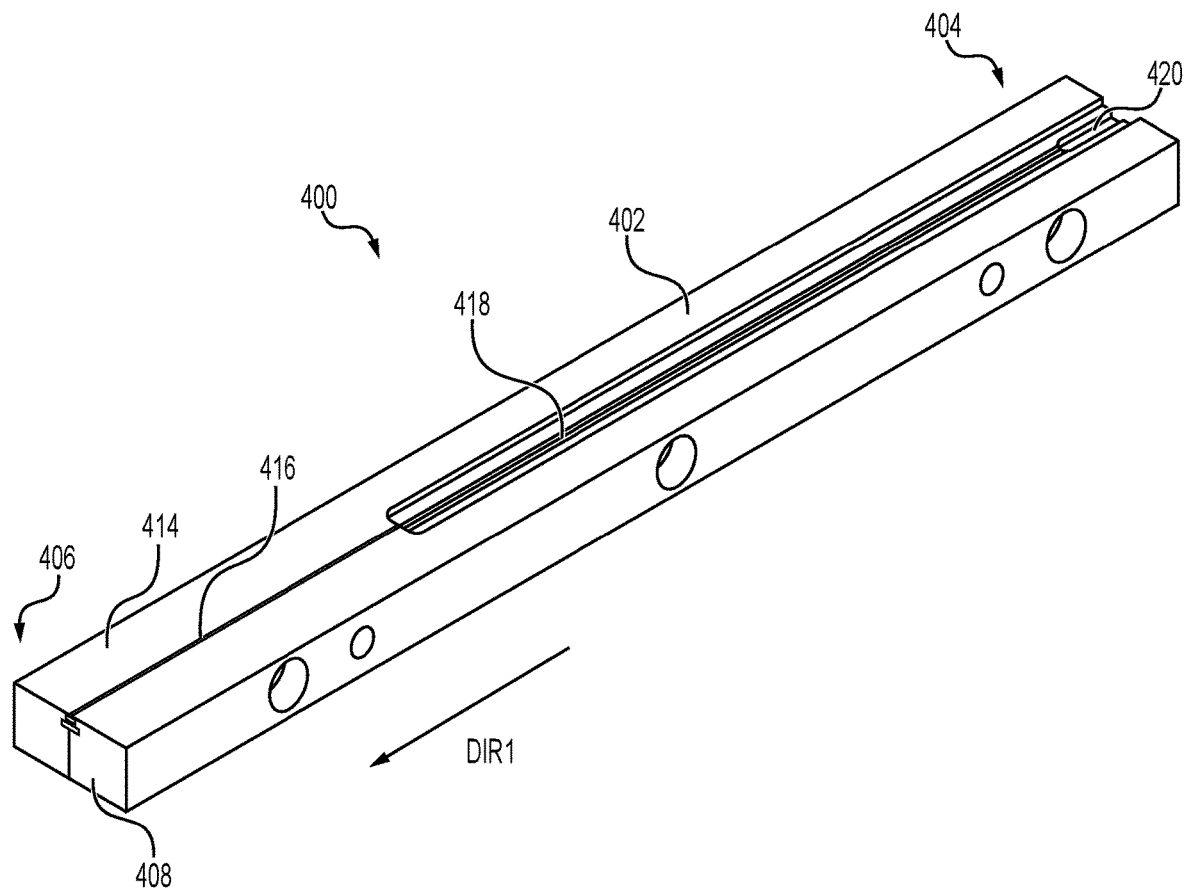
FIG. 24A is a perspective view of a cartridge for a barbed suture, the cartridge including an elongated body having a rectangular distal end, in accordance with one embodiment of the present patent application.
Figure 24B:
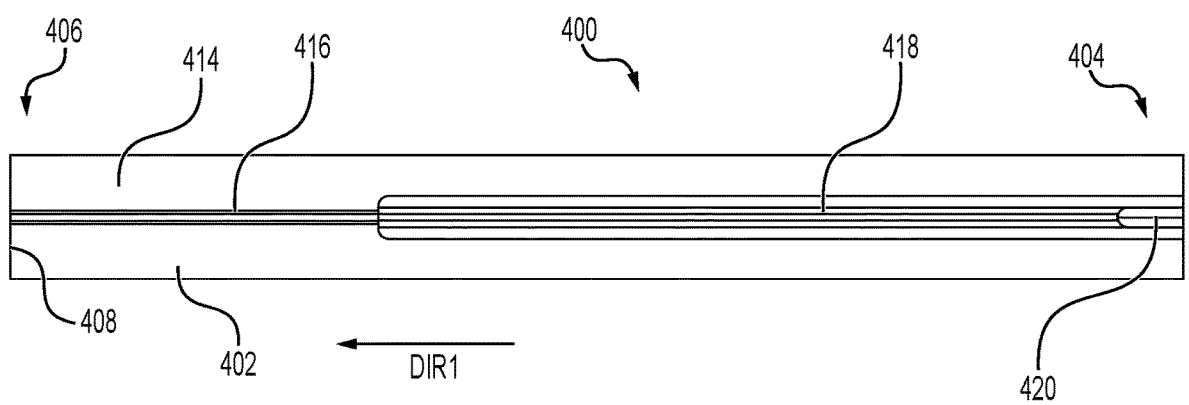
FIG. 24B is a top plan view of the cartridge shown in FIG. 24A.
Figure 24C:
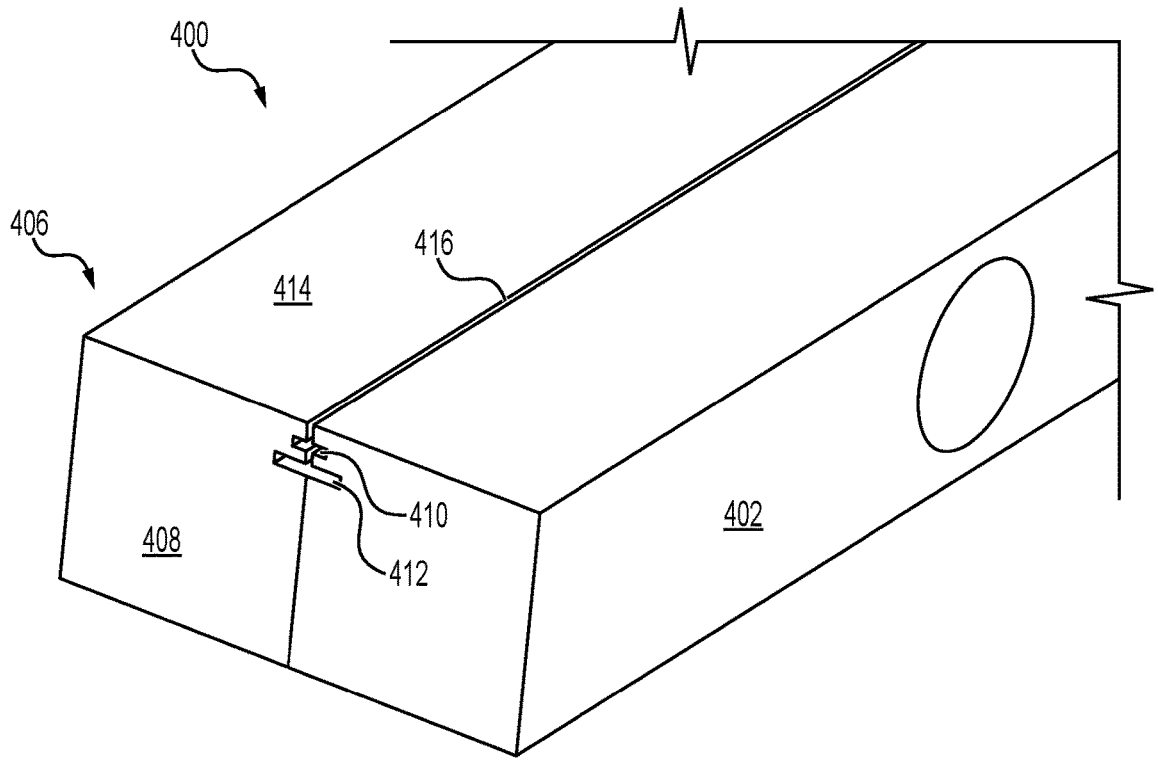
FIG. 24C is a magnified view of the distal end of the cartridge shown in FIGS. 24A and 24B.
Figure 24D:
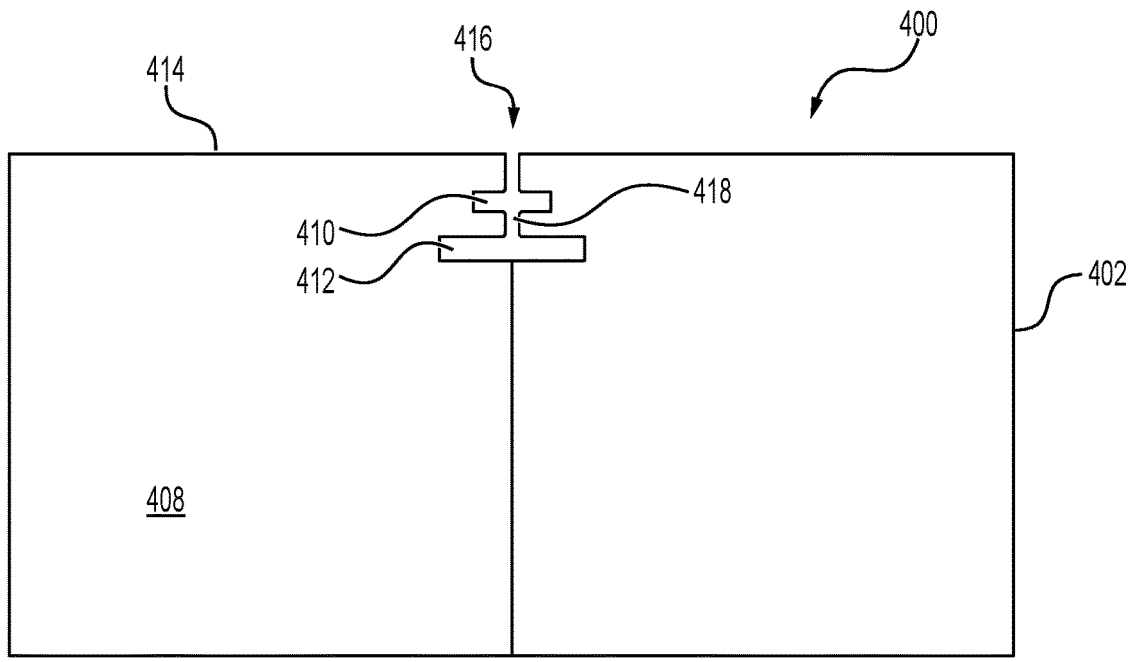
FIG. 24D is a distal end view of the cartridge shown in FIGS. 24A-24C.

Referring to FIGS. 24C and 24D, in one embodiment, the cartridge 400 preferably includes the first channel 410 that extends to the distal end 406 of the elongated body 402, and the second channel 412 that also extends to the distal end 406 of the elongated body 402. In one embodiment, the first and second channels 410, 412 preferably extend along respective axes that are parallel to one another. In one embodiment, the first and second channels 410, 412 define separate and distinct paths through the elongated body of the cartridge 400.

In one embodiment, the elongated body 402 preferably includes the major surface 414 that extends laterally across the width of the elongated body and that extends to the distal end of the elongated body. In one embodiment, the laterally extending slot 416 desirably extends from the major surface 414 to the first channel 410 of the cartridge 400 for enabling the distal end of a suture to be inserted into the first channel 410 prior to placing the cartridge 400 into a braiding machine. In one embodiment, where the first and second channels 410, 412 overlap one another along the length of the first channel 410, the elongated slot 418 preferably extends from the first channel 410 and the second channel 412, which enables the interconnecting segment of the suture to pass through the elongated slot to the distal end of the elongated body of the cartridge.

In one embodiment, the first and second channels 410, 412 preferably have respective cross-sectional areas that are different. In one embodiment, as a braider pulls a distal end of a barbed suture in a distal direction through the first channel 410, the outer dimensions of the barbs of the barbed suture preferably create a slight frictional engagement with the inner surfaces of the first channel for generating a slight drag on the barbed suture. In one embodiment, as an end effector at a proximal end of the barbed suture is pulled in the distal direction through the second channel 412, the outer dimensions of the end effector preferably create a slight frictional engagement with the inner surfaces of the second channel for generating a slight drag on the end effector.

Referring to FIGS. 25A-25D, in one embodiment, a cartridge 500 that is adapted to hold a suture for a suture braiding procedure preferably includes an elongated body 502 having a proximal end 504 and a distal end 506 having a rounded leading end 508. The cartridge preferably has one or more of the structural features of the cartridge embodiments shown and described above in FIGS. 1A-9B.

In one embodiment, the cartridge 500 preferably includes a first channel 510 that extends to the distal end 506 of the elongated body 502, and a second channel 512 that also extends to the distal end 506 of the elongated body 502. The first and second channels 510, 512 preferably define separate and distinct pathways through the cartridge 500. In one embodiment, the first and second channels 510, 512 desirably extend along respective axes that are parallel with one another. In one embodiment, the first and second channels have different cross-sectional areas. In one embodiment, the first channel 510 may be wider than high, and the second channel 512 may also be wider than high.

In one embodiment, the cartridge 500 preferably includes a major surface 514 that extends to the distal end 506 of the elongated body 502. In one embodiment, the cartridge 500 preferably includes a laterally extending slot 516 that extends from the major surface 514 to a first end (e.g., an upper end) of the first channel 510 for providing access to the first channel 510. In one embodiment, the laterally extending slot 516 has a length that matches the length of the first channel 510. In one embodiment, prior to commencement of a braiding procedure, when a suture is being loaded into the cartridge 500, a distal section of the suture may be passed through the laterally extending slot 516 for positioning the distal section of the suture within the first channel 510.

In one embodiment, the cartridge 500 preferably includes an elongated slot 518 that substantially matches the length of the second channel 512. In one embodiment, the elongated slot 518 extends to the distal end 506 of the elongated body 502 for interconnecting the first and second channels 510, 512 adjacent the distal end 506 of the elongated body 502.

In one embodiment, the proximal end 504 of the elongated body 502 desirably includes an end effector opening 520 that is preferably adjacent the proximal end of the second channel 512 and that is adapted to receive an end effector located at a proximal end of a suture (e.g., a barbed suture). In one embodiment, the end effector of the suture is adapted to be pulled distally (i.e., in the distal direction DIR1) through the second channel 512 (FIG. 25D) while a distal section of the suture is pulled through the first channel 510 (FIG. 25D) of the cartridge 500. In one embodiment, an interconnecting segment of the suture that is distal to the end effector preferably interconnects the end effector with the proximal end of the suture core. In one embodiment, the interconnecting segment preferably passes through the elongated slot 518 of the cartridge 500 as the suture is pulled distally in the direction DIR1 through the first and second channels 510, 512 (FIGS. 25A and 25B) of the cartridge 500.

Figure 25A:
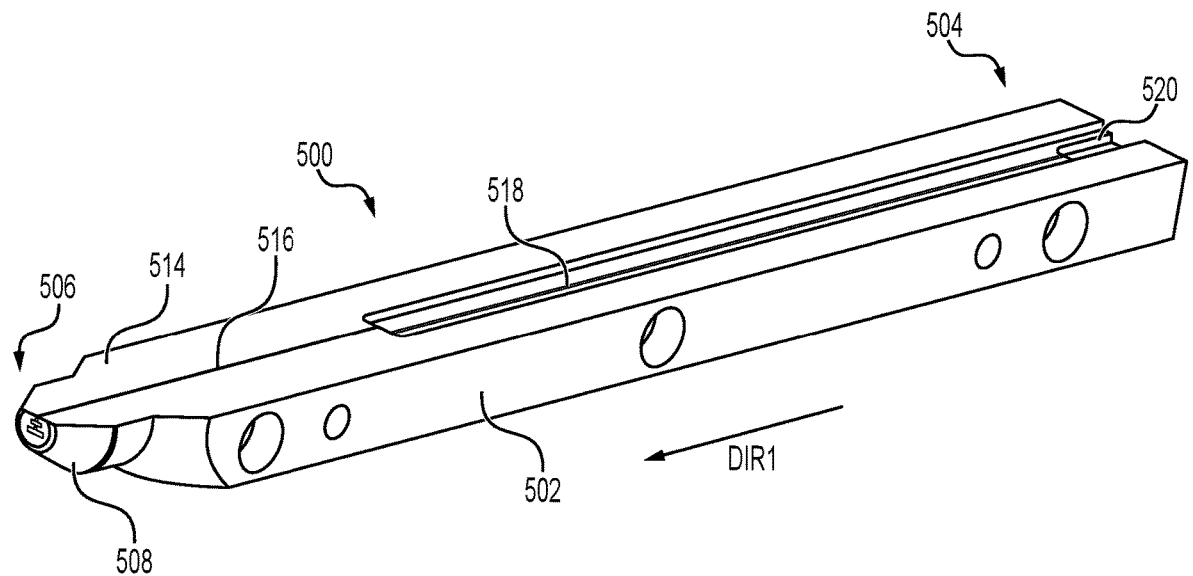
FIG. 25A is a perspective view of a cartridge for a barbed suture, the cartridge including an elongated body having a rounded distal end, in accordance with one embodiment of the present patent application.
Figure 25B:
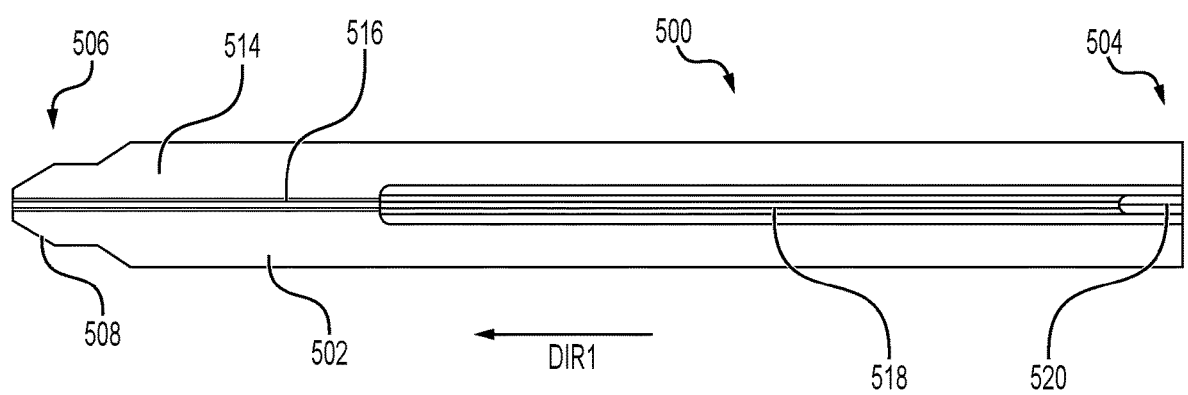
FIG. 25B is a top plan view of the cartridge shown in FIG. 25A.
Figure 25C:
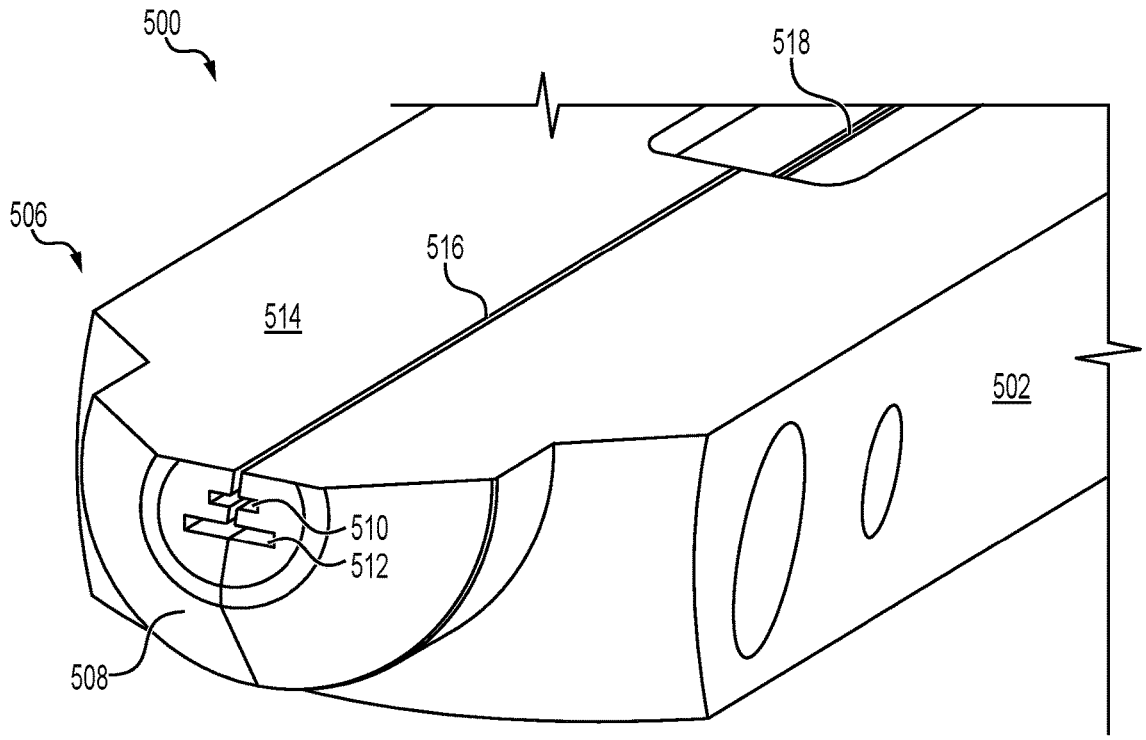
FIG. 25C is a magnified view of the distal end of the cartridge shown in FIGS. 25A and 25B.
Figure 25D:
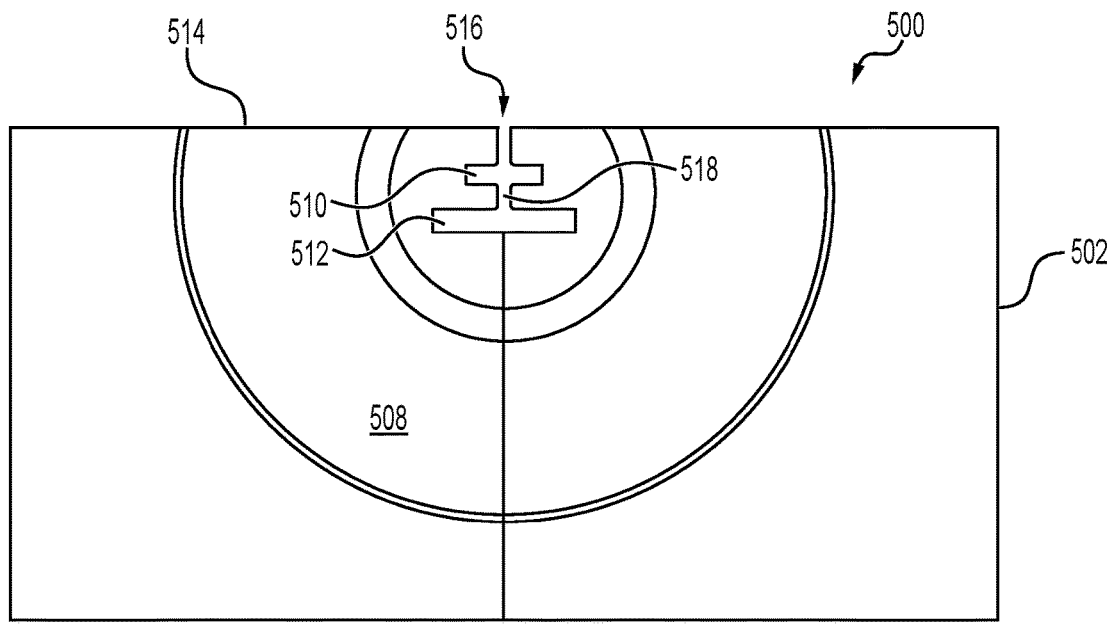
FIG. 25D is a distal end view of the cartridge shown in FIGS. 25A-25C.

Referring to FIGS. 25C and 25D, in one embodiment, the cartridge 500 preferably includes the first channel 510 that extends to the distal end 506 of the elongated body 502, and the second channel 512 that also extends to the distal end 506 of the elongated body 502. In one embodiment, the first and second channels 510, 512 preferably extend along respective axes that are parallel to one another. In one embodiment, the first and second channels 510, 512 define separate and distinct paths through the elongated body of the cartridge 500.

In one embodiment, the elongated body 502 preferably includes the major surface 514 that extends laterally across the width of the elongated body and that extends to the distal end of the elongated body. In one embodiment, the laterally extending slot 516 desirably extends from the major surface 514 to the first channel 510 of the cartridge 500 for enabling the distal end of a suture to be inserted into the first channel 510 prior to placing the cartridge 500 into a braiding machine. In one embodiment, where the first and second channels 510, 512 overlap one another along the length of the first channel 510, the elongated slot 518 preferably extends from the first channel 510 to the second channel 512, which enables the interconnecting segment of the suture to pass through the elongated slot to the distal end of the elongated body of the cartridge.

In one embodiment, the first and second channels 510, 512 preferably have respective cross-sectional areas that are different. In one embodiment, as a braider pulls a distal end of a barbed suture in a distal direction through the first channel 510, the outer dimensions of the barbs of the barbed suture preferably create a slight frictional engagement with the inner surfaces of the first channel for generating a slight drag on the barbed suture. In one embodiment, as an end effector at a proximal end of the barbed suture is pulled in the distal direction through the second channel 512, the outer dimensions of the end effector preferably create a slight frictional engagement with the inner surfaces of the second channel for generating a slight drag on the end effector.

Figure 26:
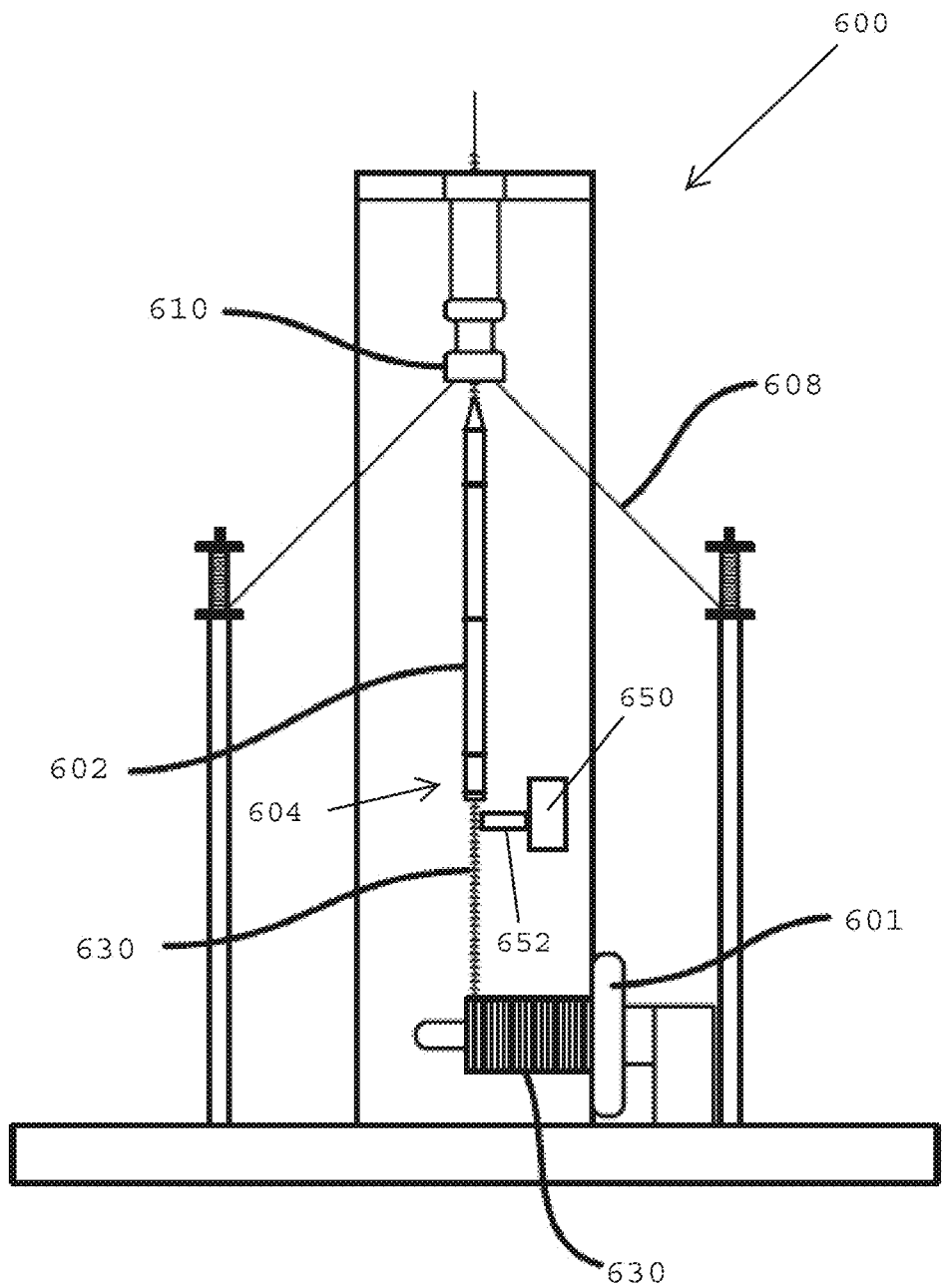
FIG. 26 illustrates an automated braiding machine having a rotatable spool with a continuous length of barbed suture inserts wound onto the spool and an end effector deflector assembly, in accordance with one embodiment of the present patent application.

Referring to FIG. 26, in one embodiment, an automated braiding system 600 preferably includes a rotatable spool 601 having a continuous length of barbed suture inserts 630 wound onto the spool 601, whereby each barbed suture insert has an elongated core having a proximal end and a distal end, outwardly projecting barbs and an end effector connected with the proximal end of the elongated core, such as the barbed suture shown and described above in FIGS. 10A-10C. In one embodiment, the barbed suture inserts 630 form a continuous length of material that may be unrolled from the spool 601 as it is fed into the braiding filament assembly to make a series of braided barbed sutures that may be separated from one another into distinct units of barbed sutures.

In one embodiment, the automated braiding system 600 preferably includes an elongated body 602 through which the barbed suture inserts 630 are continuously fed in the direction DIR2. The automated braiding system 600 preferably includes filaments 608 that are braided around the barbed suture inserts 630 at a braider eyelet 610.

In one embodiment, the elongated body 602 has one or more of the structural features of the cartridge embodiments shown and described above in FIGS. 1A-9B, 23A-23D, 24A-24D, and 25A-25D.

In one embodiment, the elongated body 602 preferably has first and second channels, an elongated slot that interconnects the first and second channels, and an end effector opening for positioning an end effector within the second channel, as described above in the embodiments of FIGS. 1A-9B, 23A-23D, 24A-24D, and 25A-25D. The first channel of the elongated body 602 preferably has a cross-sectional area that is configured to closely conform to the cross-sectional shape of the barbed section of the barbed suture insert, and the second channel of the elongated body 602 preferably has a cross-sectional area that is configured to closely conform to the cross-sectional shape of the end effector that is connected with the proximal end of elongated core of the barbed suture insert, thereby generating drag as the barbed suture insert is pulled in the direction DIR2 through the elongated body 602 for being fed into the braider eyelet 610. The first and second channels preferably enable the continuous barbed suture inserts to move axially relative to the elongated body 602, but prevents the barbed suture inserts from rotating or twisting about its longitudinal axis relative to the elongated body 602.

In one embodiment, as each barbed suture insert 630 is pulled in the direction DIR2 toward the braider eyelet 610, the elongated body 602 is preferably locked in position so that it does not rotate around its longitudinal axis, which, in turn, will prevent the barbed suture inserts 630 from rotating as they are pulled through the elongated body 602 and introduced into the braider eyelet 610 of the braider filament assembly.

In one embodiment, the elongated body 602 may be selectively rotated about its longitudinal axis to counteract any undesirable twisting of the barbed suture inserts 630 as they are fed into the automated braider.

Figure 27A:
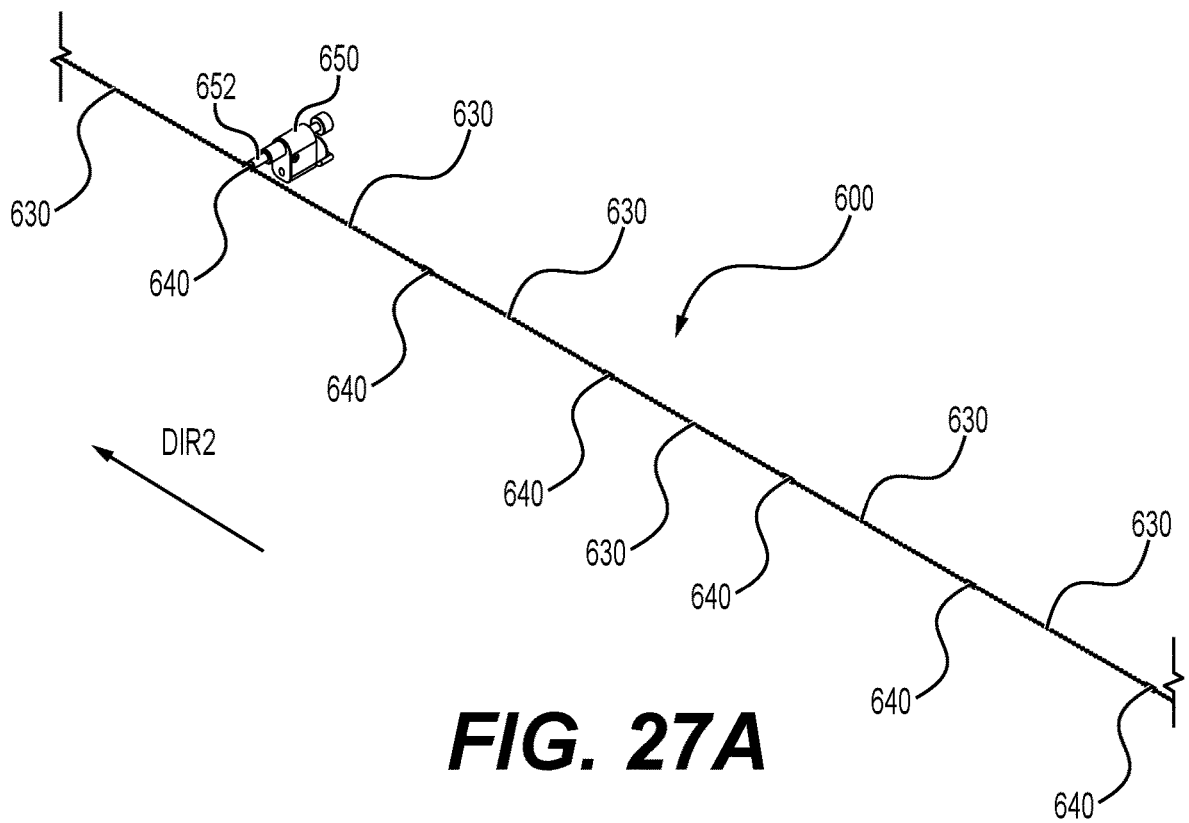
FIG. 27A shows the end effector deflector assembly and the continuous length of barbed suture inserts of FIG. 26.
Figure 27B:
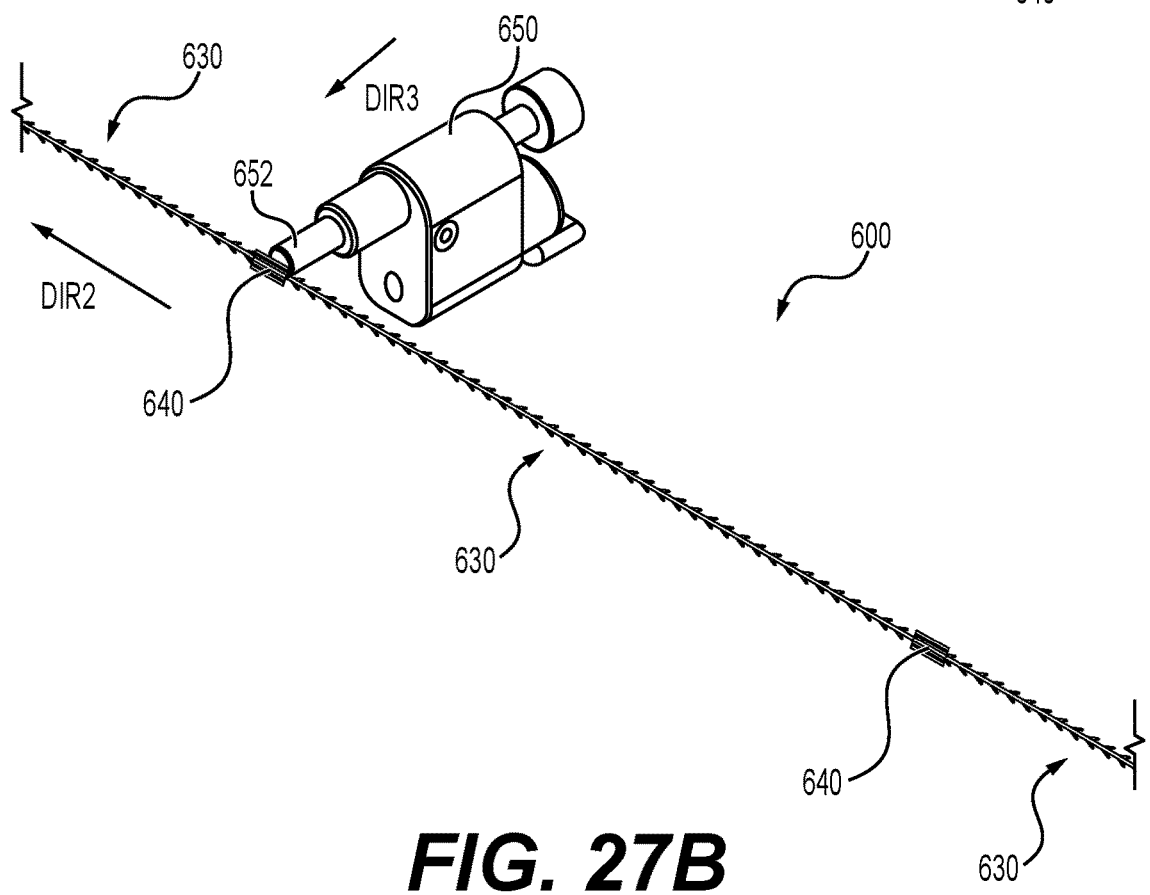
FIG. 27B is a magnified view of the end effector deflector assembly and the continuous length of barbed suture inserts of FIG. 27A.

Referring to FIGS. 26 and 27A-27B, in one embodiment, the automated braiding system 600 preferably includes an end effector deflector assembly 650 that is configured to selectively engage the barbed suture inserts 630 as the continuous length of barbed suture inserts are pulled into the automated braiding system 600 in the direction DIR2. In one embodiment, the end effector deflector assembly 650 preferably includes a deflecting finger 652 that may be selectively extended in the direction DIR3, which may be perpendicular to the direction DIR2, for deflecting the end effectors 640 of the barbed suture inserts 630 into the end effector opening and the second channel of the elongated body 602. A sensor, such as an optical sensor, may be utilized for automatically extending and retracting the deflecting finger 652. In embodiment, each time one of the end effectors approaches the proximal end 604 of the elongated body 602, the deflecting finger 652 is automatically extended for pushing the end effector into the end effector opening for being aligned with the second channel of the elongated body 602. As a result, the barbed section of the barbed suture insert will be pulled through the first channel of the elongated body 602 as the end effector 640 is pulled through the second channel of the elongated body 302.

Figure 28C:
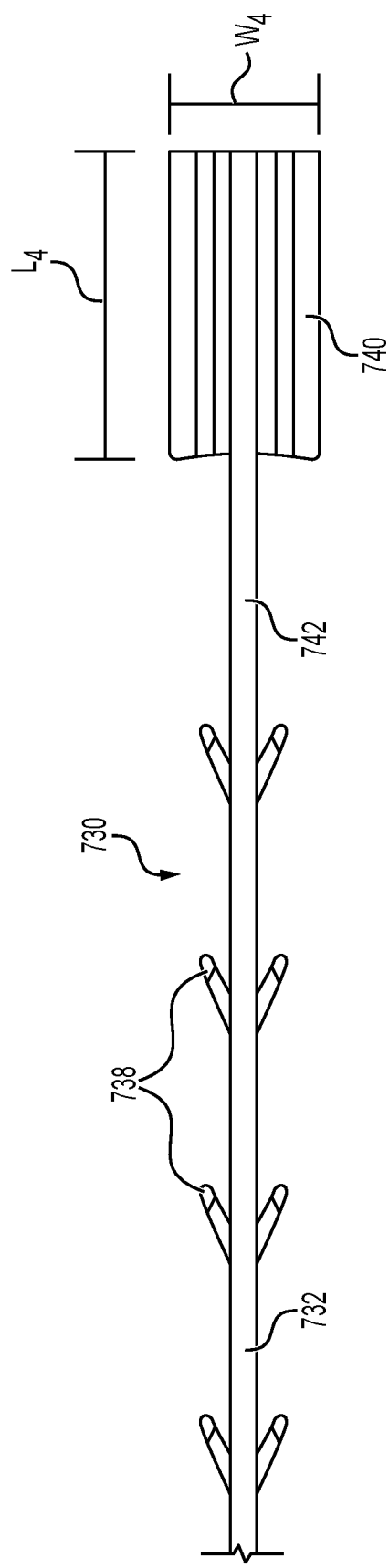
FIG. 28C is a magnified view of a distal end of the barbed suture shown in FIGS. 28A and 28B.

Referring to FIGS. 28A-28C, in one embodiment, a barbed suture 730 is preferably adapted to be loaded into one of the cartridges shown and described in FIGS. 1A-9B, 23A-23D, 24A-24D, and 25A-25D or the elongated body 602 shown and described in FIG. 26. In one embodiment, the barbed suture 730 preferably includes an elongated core 732 having a proximal end 734 and a distal end 736. In one embodiment, the barbed suture 730 preferably includes a plurality of barbs 738 that project outwardly from opposite sides of the elongated core 732. In one embodiment, the distal end 736 of the elongated core 732 may be devoid of barbs. The barbed suture 730 preferably includes an end effector 740 that is connected with the proximal end 734 of the elongated core 732. In one embodiment, the barbed suture 730 preferably includes an interconnecting segment 742 that is located between the end effector 740 and the barbs 738. In one embodiment, the barbed suture 730 preferably includes a proximal barbed section 743 that is distal to the interconnecting segment 742 and a distal barbed section 745 that is distal to the proximal barbed section 743. In one embodiment, a midway point of the barbed suture, which is about halfway along the length of the elongated core 732, may divide the proximal barbed section 743 from the distal barbed section 745.

Figure 28D:
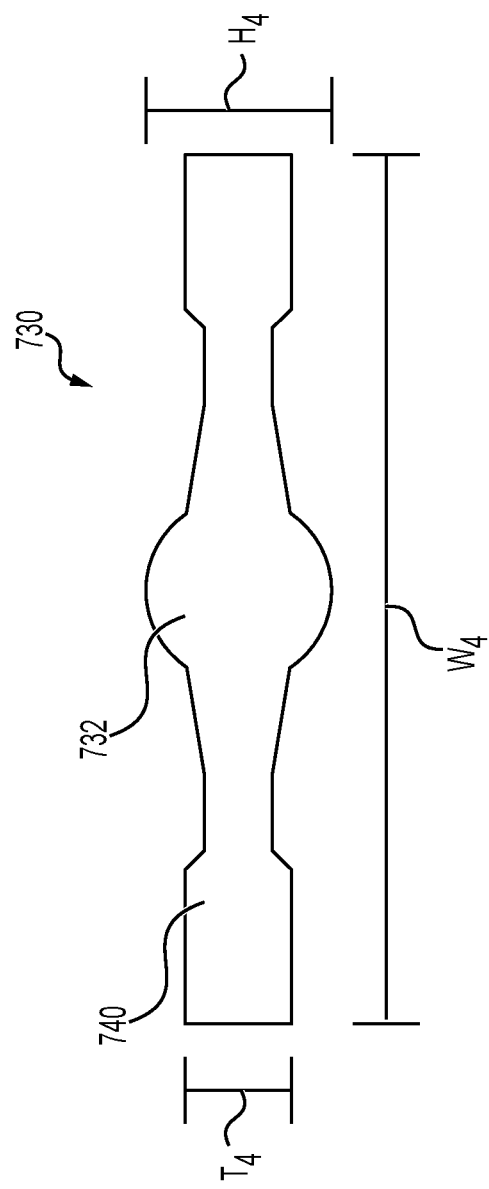
FIG. 28D is a distal end view of a distal end of the barbed suture shown in FIGS. 28A-28C.
Figure 29B:
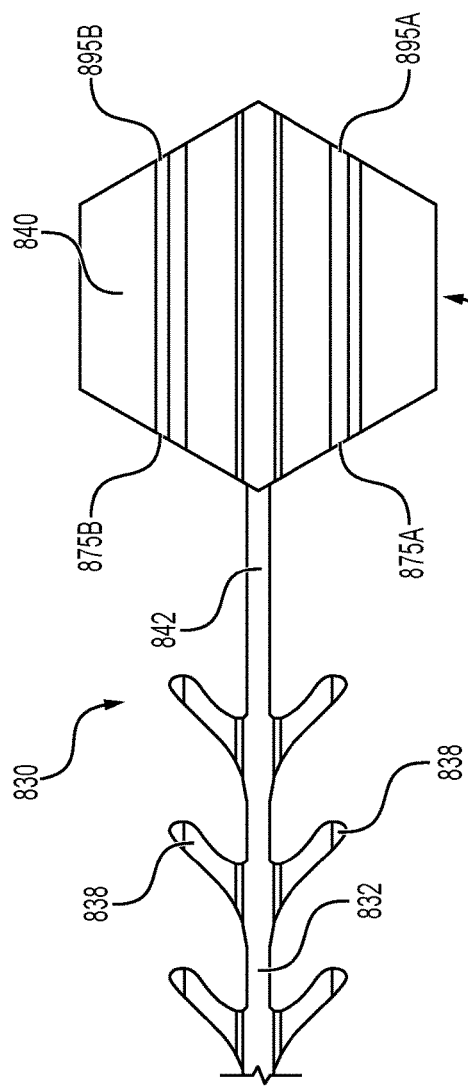
FIG. 29B is a top view of the barbed suture and the end effector shown in FIG. 29A.
Figure 29C:
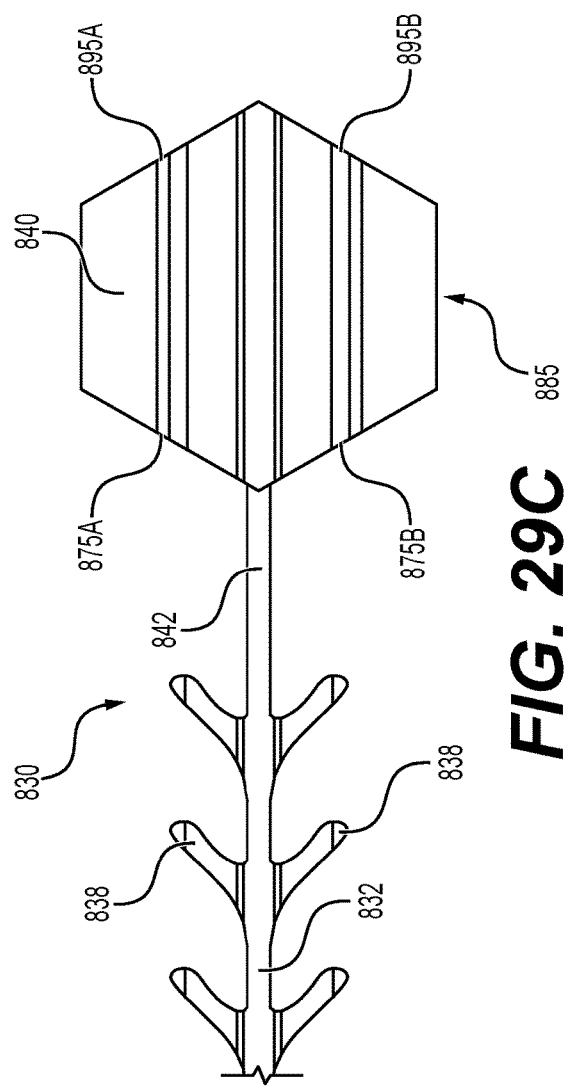
FIG. 29C is a bottom view of the barbed suture and the end effector shown in FIGS. 29A and 29B.
Figure 29D:
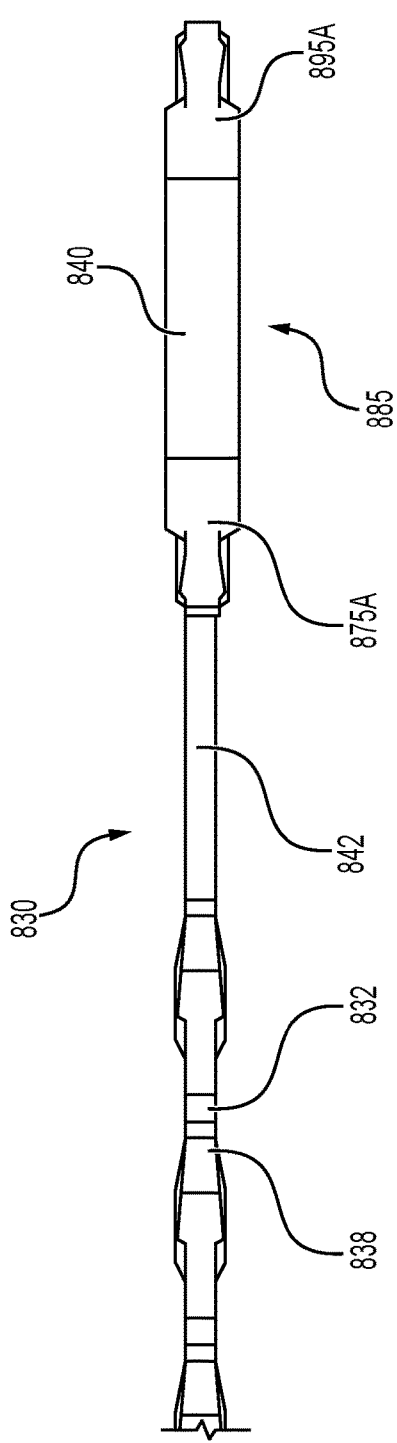
FIG. 29D is a left side view of the barbed suture and the end effector shown in FIGS. 29A-29C.
Figure 29E:
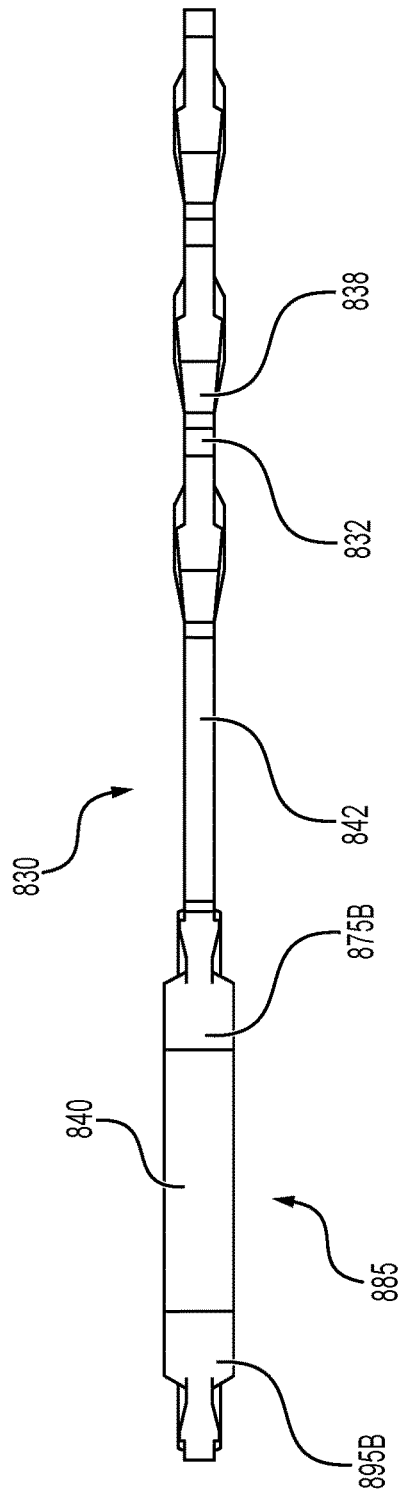
FIG. 29E is a right side view of the barbed suture and the end effector shown in FIGS. 29A-29D.
Figure 29F:
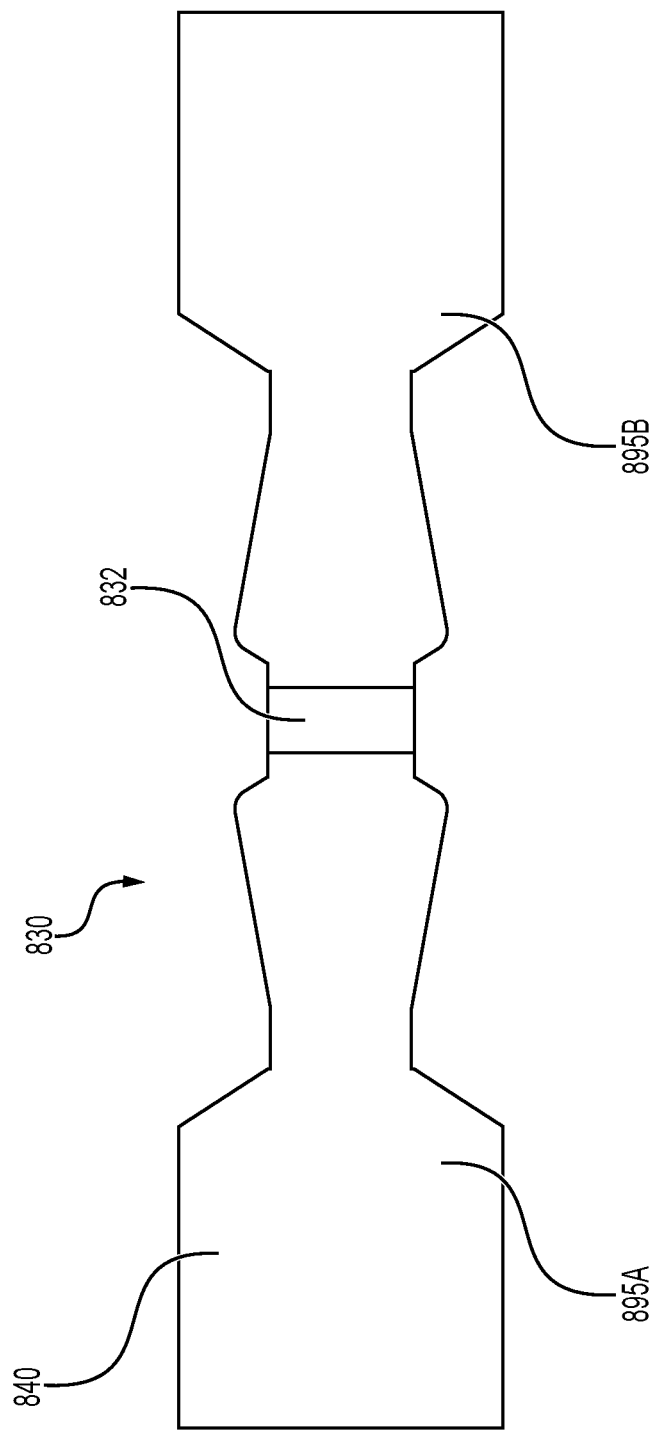
FIG. 29F is a proximal end view of the end effector shown in FIG. 29B.

Referring to FIGS. 28C and 28D, in one embodiment, the end effector 740 may include a stopper having a square or rectangular shape with a length $L_4$, a width $W_4$, and a thickness $T_4$. Referring to FIG. 28D, in one embodiment, the elongated core 732 has a height $H_4$ that is greater than the thickness $T_4$ of the end effector 740.

Referring to FIGS. 29A-29F, in one embodiment, a barbed suture 830 preferably includes an elongated core 832 and barbs 838 that project outwardly from the elongated core. The barbed suture 830 preferably includes an end effector 840 that is connected with the proximal end of the elongated core 832. In one embodiment, the barbed suture 830 preferably includes an interconnecting segment 842 that is located between the end effector 840 and the barbs 838. In one embodiment, the end effector 840 may have transition surfaces that facilitate a smooth transition of the braided filaments from the smaller width of the elongated core 832 to the larger width of the end effector 840. In one embodiment, the end effector 840 has a generally diamond-like shape with leading sloping surfaces 875A, 875B that transition outwardly to a wider central section 885, and trailing sloping surfaces 895A, 895B that transition back to the smaller width of the non-barbed, leader of the elongated core of the next barbed suture. The angles of the respective leading sloping surfaces 875A, 875B and trailing sloping surfaces 895A, 895B preferably complement that of the braid point (e.g., the braiding eye) where the filaments converge for maintaining the end effector 840 in the center of the braiding zone and allowing for balanced coverage of the filaments over the end effector.

Figure 30:
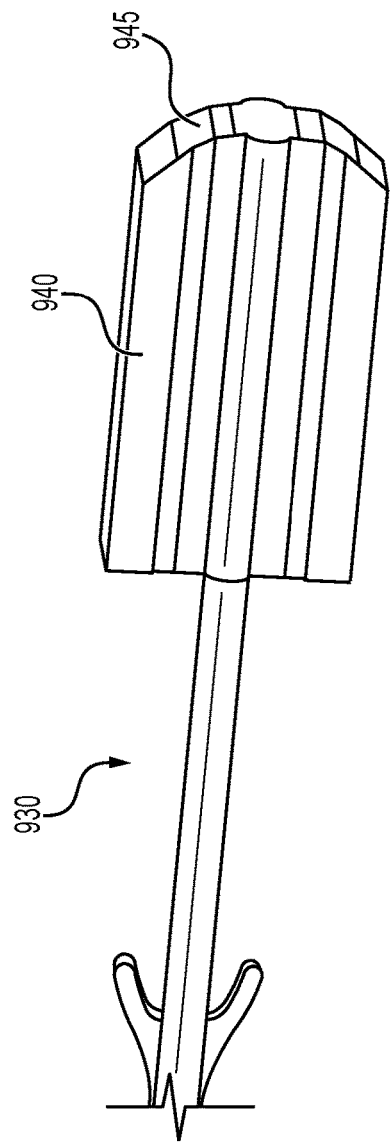
FIG. 30 is a perspective view of a barbed suture having an elongated core and an end effector secured to a proximal end of the elongated core, in accordance with one preferred embodiment of the present patent application.
Figure 31:
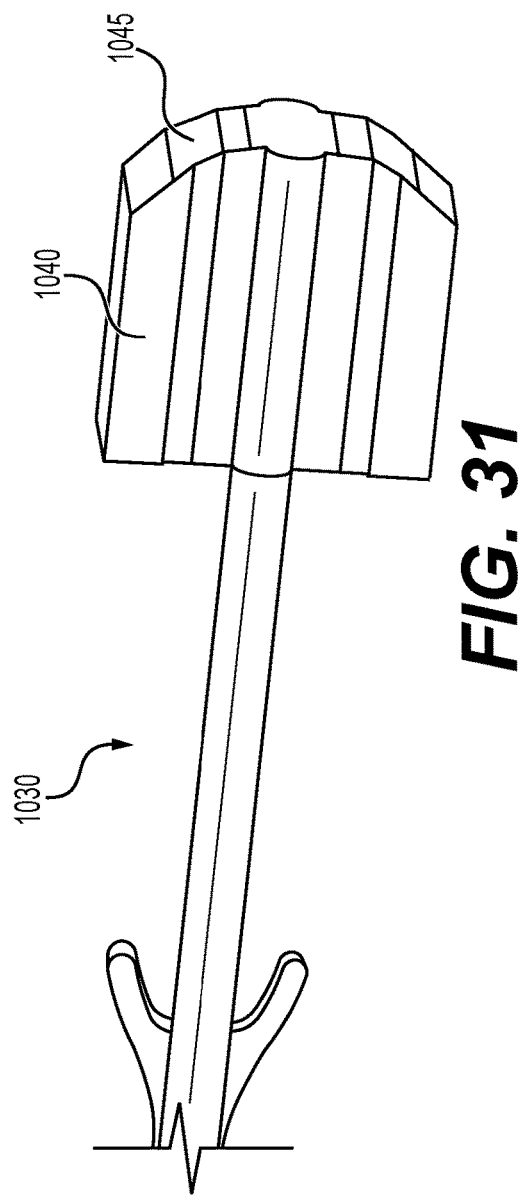
FIG. 31 is a perspective view of a barbed suture having an elongated core and an end effector secured to a proximal end of the elongated core, in accordance with one preferred embodiment of the present patent application.

Referring to FIG. 30, in one embodiment, a barbed suture 930 has an end effector 940 having a rectangular shape with a proximal end 945 that defines a convexly curved surface. Referring to FIG. 31, in one embodiment, a barbed suture 1030 has an end effector 1040 having a square shape with a proximal end 1045 that defines a convexly curved surface.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A device for guiding a suture into a braider comprising:
   a body having a proximal end, a distal end, and an axis that extends from the proximal end to the distal end;
   a first channel extending along the axis of said body and having a first distal opening at the distal end of said body, wherein said first channel has a first cross-sectional area;
   a second channel extending along the axis of said body and having a second distal opening at the distal end of said body, wherein said second channel has a second cross-sectional area that is larger than the first cross-sectional area of said first channel; and
   a slot extending along the axis of said body and having a distal slot opening at the distal end of said body, wherein said slot interconnects said first and second channels.

2. The device as claimed in claim 1, wherein said body is an elongated body, and wherein said axis is a longitudinal axis that extends from the proximal end to the distal end of said elongated body.

3. The device as claimed in claim 2, further comprising:
   said first channel extending along the longitudinal axis of said elongated body, wherein said first channel has a width and a height defining said first cross-sectional area of said first channel; and
   said second channel extending along the longitudinal axis of said elongated body, wherein said second channel has a width and a height defining said second cross-sectional area of said second channel.

4. The device as claimed in claim 1, wherein said first and second channels are parallel to one another.

5. The device as claimed in claim 1, wherein said first and second channels are spaced from one another.

6. The device as claimed in claim 1, wherein said slot has a first end in communication with said first channel and a second end in communication with said second channel.

7. The device as claimed in claim 3, wherein the width of said second channel is different than the width of said first channel.

8. The device as claimed in claim 3, wherein the height of said second channel is different than the height of said first channel.

9. The device as claimed in claim 1, wherein the second channel is longer than the first channel.

10. The device as claimed in claim 2, wherein a proximal section of said elongated body has a first outer dimension, and wherein the distal end of said elongated body comprises a head having a second outer dimension that is larger than the first outer dimension of the proximal section of said elongated body.

11. The device as claimed in claim 10, wherein said first channel, said second channel and said slot extend through said head to the distal end of said elongated body for defining said first distal opening, said second distal opening, and the distal slot opening, respectively.

12. The device as claimed in claim 2, further comprising:
said elongated body having a major surface that extends to the distal end of said elongated body and that overlies said first channel; and
a lateral elongated slot that extends from said major surface to said first channel for providing lateral access to said first channel of said elongated body.

13. The device as claimed in claim 2, further comprising:
a barbed suture including an elongated core having a proximal end and a distal end, a barbed section including barbs extending outwardly from said elongated core, and an end effector secured to the proximal end of said elongated core, wherein said elongated core includes an interconnecting segment that is distal to said end effector and proximal to said barbed section; and
said barbed suture being loaded into said elongated body with said barbed section of said barbed suture disposed within said first channel, said end effector of said barbed suture disposed within said second channel, and said interconnecting segment of said barbed suture extending through said slot.

14. The device as claimed in claim 13, wherein said barbed section of said barbed suture defines a first cross-sectional dimension and said end effector of said barbed suture defines a second cross-sectional dimension that is larger than the first cross-sectional dimension of said barbed section of said barbed suture.

15. The device as claimed in claim 14, wherein the first cross-sectional dimension of said barbed section of said barbed suture substantially matches said first cross-sectional area of said first channel and said second cross-sectional dimension of said end effector substantially matches said second cross-sectional area of said second channel.

16. A device for guiding a barbed suture into a braider comprising:
an elongated body having a proximal end, a distal end, and a longitudinal axis that extends from the proximal end to the distal end of said elongated body;
a first channel extending along the longitudinal axis of said elongated body and having a first distal opening at the distal end of said elongated body, wherein said first channel has a first cross-sectional area;
a second channel extending along the longitudinal axis of said elongated body and having a second distal opening at the distal end of said elongated body, wherein said second channel has a second cross-sectional area that is different than the first cross-sectional area of said first channel;
an elongated slot extending along the longitudinal axis of said elongated body that interconnects said first and second channels; and
a barbed suture loaded into said elongated body, said barbed suture including an elongated core having a proximal end, a distal end, a barbed section including barbs extending outwardly from said elongated core, an end effector secured to the proximal end of said elongated core, and an interconnecting segment of said elongated core that is distal to said end effector and proximal to said barbed section, wherein said barbed section of said barbed suture is disposed within said first channel, said end effector of said barbed suture is disposed within said second channel, and said interconnecting segment of said barbed suture extends through said elongated slot.

17. The device as claimed in claim 16, wherein said first and second channels are parallel to one another and are spaced from one another for defining two separate paths through said elongated body of said device.

18. The device as claimed in claim 16, further comprising:
said elongated body having a major surface that extends to the distal end of said elongated body and that overlies said first channel; and
a laterally extending slot that extends from said major surface to said first channel for providing lateral access to said first channel of said elongated body.

19. A method of making a braided barbed suture, comprising:
guiding a barbed suture into a braider using a guide device, the barbed suture including an elongated core having a proximal end, a distal end, a barbed section including barbs extending outwardly from the elongated core, an end effector secured to the proximal end of the elongated core, and an interconnecting segment of the elongated core that is distal to the end effector and proximal to the barbed section, the device comprising:
an elongated body extending along a longitudinal axis from a proximal end to a distal end thereof;
a first channel extending along the longitudinal axis of the elongated body and having a first distal opening at the distal end of the elongated body, wherein the first channel has a first cross-sectional area;
a second channel extending along the longitudinal axis of the elongated body and having a second distal opening at the distal end of the elongated body, wherein the second channel has a second cross-sectional area different than the first cross-sectional area; and
an elongated slot extending along the longitudinal axis of the elongated body that interconnects the first and second channels;
loading the barbed suture into the elongated body so that the barbed section of the barbed suture is disposed within the first channel, the end effector of the barbed suture is disposed within the second channel and the interconnecting segment of the barbed suture extends through the elongated slot with a distal-most tip of the elongated core extending distally beyond the distal end of the elongated body;

aligning the distal end of the elongated body with a braiding zone of a braider for braiding around the distal-most tip of the barbed suture that extends distally beyond the distal end of the elongated body; and maintaining the distal end of the elongated body of the device in alignment with the braiding zone of the braider until the barbed suture is fully drawn into the braider.

20. The method as claimed in claim 19, wherein the aligning step comprises disposing said elongated body in a guide tube so that said distal end of said elongated body projects beyond a distal end of said guide tube, and wherein the method further comprises:

after said barbed suture is fully drawn into said braider, retracting said guide tube and said elongated body disposed in said guide tube away from the braiding zone of said braider.

* * * * *